(12) United States Patent
Miller-Tait et al.

(10) Patent No.: US 12,740,825 B2
(45) **Date of Patent: *Sep. 22, 2026**

(54) SYSTEMS AND METHODS FOR TREATING TISSUE WITH PULSED FIELD ABLATION

(71) Applicant: KARDIUM INC., Burnaby (CA)

(72) Inventors: Shane Fredrick Miller-Tait, North Vancouver (CA); Gerald Floyd Cummings, Port Moody (CA)

(73) Assignee: KARDIUM INC., Burnaby (CA)

( * ) Notice: Subject to any disclaimer, the term of this patent is extended or adjusted under 35 U.S.C. 154(b) by 137 days.

This patent is subject to a terminal disclaimer.

(21) Appl. No.: 18/782,688

(22) Filed: Jul. 24, 2024

(65) Prior Publication Data

US 2024/0374300 A1 Nov. 14, 2024

Related U.S. Application Data

(63) Continuation of application No. 17/399,381, filed on Aug. 11, 2021, now Pat. No. 12,076,071.
(Continued)

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1492* (2013.01); *A61B 2018/00178* (2013.01);
(Continued)

(58) Field of Classification Search
CPC ............ A61B 18/1206; A61B 18/1492; A61B 2018/0016; A61B 2018/00178;
(Continued)

(56) References Cited

U.S. PATENT DOCUMENTS 5,697,377 A 12/1997 Wittkampf
5,865,787 A 2/1999 Shapland
(Continued)

FOREIGN PATENT DOCUMENTS

AU 2012220523 A1 10/2012
AU 2015201643 A1 4/2015
(Continued)

OTHER PUBLICATIONS

Office Action issued in copending U.S. Appl. No. 17/521,107 mailed May 5, 2025.
(Continued)

*Primary Examiner* — Daniel W Fowler
(74) *Attorney, Agent, or Firm* — ROSSI, KIMMS & McDOWELL LLP

(57) ABSTRACT

Pulsed field ablation systems are disclosed, some of which may include an output pulse generation circuit and a high voltage pulse generation circuit electrically connected to the output pulse generation circuit. The high voltage pulse generation circuit may be configured to deliver a high voltage pulse set to the output pulse generation circuit. The output pulse generation circuit may be configured to generate an output pulse set at least in response to the high voltage pulse set. The output pulse set may be deliverable to a set of selectable electrodes and may be configured to cause pulsed field ablation of tissue. Each pulse in the output pulse set may have a rise time that is shorter than a rise time of at least one high voltage pulse in the high voltage pulse set.

22 Claims, 17 Drawing Sheets

Related U.S. Application Data

(60) Provisional application No. 63/065,714, filed on Aug. 14, 2020.

(51) Int. Cl.
*A61B 18/00* (2006.01)
*A61B 18/08* (2006.01)

(52) U.S. Cl.
CPC ............... *A61B 2018/00351* (2013.01); *A61B 2018/00577* (2013.01); *A61B 2018/00642* (2013.01); *A61B 2018/00708* (2013.01); *A61B 2018/0072* (2013.01); *A61B 2018/00767* (2013.01); *A61B 2018/087* (2013.01); *A61B 2018/126* (2013.01); *A61B 2018/1286* (2013.01)

(58) Field of Classification Search
CPC ........... A61B 2018/00267; A61B 2018/00351; A61B 2018/00357; A61B 2018/00375; A61B 2018/00577; A61B 2018/00642; A61B 2018/00708; A61B 2018/0072; A61B 2018/00761; A61B 2018/00767; A61B 2018/00797; A61B 2018/00839; A61B 2018/087; A61B 2018/124; A61B 2018/126; A61B 2018/1286
See application file for complete search history.

(56) References Cited

U.S. PATENT DOCUMENTS 6,171,305 B1 1/2001 Sherman
6,387,671 B1 5/2002 Rubinsky
7,001,383 B2 2/2006 Keidar
8,401,645 B2 3/2013 Rosenberg et al.
8,454,589 B2 6/2013 Deno et al.
8,906,011 B2 12/2014 Gelbart
9,198,592 B2 12/2015 Reinders et al.
9,351,790 B2 5/2016 Zemel
9,439,713 B2 9/2016 Reinders
9,452,016 B2 9/2016 Moisa et al.
9,655,670 B2 5/2017 Larson
9,764,145 B2 9/2017 Callas
9,788,885 B2 10/2017 Long
10,080,602 B2 9/2018 Wittkampf
10,905,492 B2 2/2021 Neal, II
11,033,329 B2 6/2021 Stewart et al.
11,272,979 B2 3/2022 Garcia et al.
2001/0000791 A1 5/2001 Suorsa et al.
2007/0265526 A1 11/2007 Govari
2009/0198231 A1* 8/2009 Esser .................... A61N 1/327 606/41
2009/0281541 A1 11/2009 Ibrahim et al.
2011/0066032 A1 3/2011 Vitek et al.
2011/0106221 A1 5/2011 Neal
2011/0144641 A1 6/2011 Dimalanta, Jr. et al.
2011/0245756 A1 10/2011 Arora et al.
2013/0197425 A1 8/2013 Golberg et al.
2013/0345779 A1 12/2013 Maor et al.
2014/0039489 A1* 2/2014 Davalos ............ A61B 18/1206 606/41
2014/0081262 A1 3/2014 Koblish et al.
2014/0207133 A1 7/2014 Model et al.
2015/0073401 A1 3/2015 Kreindel
2015/0126922 A1 5/2015 Willis
2015/0265335 A1 9/2015 Bakos et al.
2015/0289923 A1 10/2015 Davalos et al.
2016/0058493 A1 3/2016 Neal, II et al.
2016/0100879 A1 4/2016 Long
2016/0113707 A1 4/2016 Sahakian et al.
2016/0317844 A1 11/2016 Lupotti
2016/0338761 A1 11/2016 Chornenky et al.
2016/0374710 A1 12/2016 Sinelnikov et al.
2017/0065343 A1 3/2017 Mickelsen
2017/0105793 A1 4/2017 Cao et al.
2017/0120080 A1 5/2017 Phillips et al.
2017/0156792 A1 6/2017 Ziv-Ari et al.
2017/0224402 A1 8/2017 Borsic
2017/0224414 A1 8/2017 Weinkam et al.
2017/0319851 A1 11/2017 Athos et al.
2018/0036065 A1 2/2018 Yates et al.
2018/0318003 A1 11/2018 Killu et al.
2019/0060632 A1 2/2019 Asirvatham
2019/0069950 A1 3/2019 Viswanathan et al.
2019/0143106 A1 5/2019 Dewitt et al.
2019/0216525 A1 7/2019 Stewart
2019/0216538 A1 7/2019 Wittkampf
2019/0232048 A1 8/2019 Latouche
2019/0282294 A1 9/2019 Davalos
2019/0328445 A1 10/2019 Sano et al.
2019/0328446 A1 10/2019 Callas et al.
2020/0005373 A1 1/2020 McNall et al.
2020/0046423 A1 2/2020 Viswanathan et al.
2020/0046432 A1 2/2020 Garcia et al.
2020/0069367 A1 3/2020 Sinnott
2020/0138506 A1 5/2020 Fraasch et al.
2020/0171303 A1 6/2020 Sano et al.
2020/0179046 A1 6/2020 Wittkampf et al.
2020/0261150 A1 8/2020 Lee et al.
2020/0289185 A1 9/2020 Forsyth et al.
2020/0289188 A1 9/2020 Forsyth et al.
2020/0315684 A1 10/2020 Swanson
2020/0323576 A1 10/2020 Neal et al.
2020/0323588 A1 10/2020 Moss et al.
2020/0390497 A1 12/2020 Zemlin
2021/0015549 A1 1/2021 Haghighi-Mood et al.
2021/0023362 A1 1/2021 Lorenzo et al.
2021/0030470 A1 2/2021 Pearson et al.
2021/0106374 A1* 4/2021 Forsyth ................ A61B 5/4836
2021/0177503 A1 6/2021 Altmann et al.
2021/0282847 A1 9/2021 Viswanathan et al.
2021/0315639 A1 10/2021 Manucherhabadi et al.
2022/0104875 A1 4/2022 Gleiman et al.
2022/0133403 A1 5/2022 Olson et al.
2022/0151688 A1 5/2022 Garcia et al.
2022/0161027 A1 5/2022 Aycock et al.
2022/0183752 A1 6/2022 Werneth et al.
2022/0192741 A1 6/2022 Reinders et al.
2022/0249151 A1 8/2022 Forrest et al.
2023/0026265 A1 1/2023 Shuros et al.
2023/0054079 A1 2/2023 Lakshmi
2023/0057137 A1 2/2023 Reinders et al.
2023/0149073 A1 5/2023 Forrest et al.
2023/0301595 A1 9/2023 Rogers et al.
2023/0310061 A1 10/2023 Stewart et al.
2023/0346468 A1 11/2023 Reinders et al.
2024/0238030 A1 7/2024 Duong et al.

FOREIGN PATENT DOCUMENTS

CA 2981867 A1 10/2016
CN 105055015 A 11/2015
CN 106264723 A 1/2017
CN 106388929 A 2/2017
CN 106591118 A 4/2017
CN 106877729 A 6/2017
CN 206355132 U 7/2017
CN 206548596 U 10/2017
CN 206992984 U 2/2018
CN 108113748 A 6/2018
CN 109124760 A 1/2019
CN 109593753 A 4/2019
CN 109875678 A 6/2019
CN 110123437 A 8/2019
CN 209360881 U 9/2019
CN 209392090 U 9/2019
CN 209464086 U 10/2019
CN 110693605 A 1/2020
CN 110693606 A 1/2020
CN 110840552 A 2/2020
CN 110946642 A 4/2020
CN 111388084 A 7/2020
CN 111437513 A 7/2020

(56) References Cited

FOREIGN PATENT DOCUMENTS

CN 111529050 A 8/2020
CN 111658134 A 9/2020
CN 211512038 U 9/2020
CN 111728693 A 10/2020
CN 111839719 A 10/2020
CN 111904590 A 11/2020
CN 112022338 A 12/2020
CN 112039178 A 12/2020
CN 212326561 U 1/2021
CN 212346713 U 1/2021
CN 112336448 A 2/2021
CN 212788678 U 3/2021
CN 112618002 A 4/2021
CN 112694974 A 4/2021
CN 112618010 B 5/2021
CN 112842516 A 5/2021
CN 112022331 A 6/2021
CN 112869871 A 6/2021
CN 112869872 A 6/2021
CN 112914717 A 6/2021
CN 112932648 A 6/2021
CN 112932652 A 6/2021
CN 113017819 A 6/2021
CN 113081239 A 7/2021
CN 113100916 A 7/2021
CN 113100917 A 7/2021
CN 113100918 A 7/2021
CN 113143444 A 7/2021
CN 113143447 A 7/2021
CN 113229928 A 8/2021
CN 113229930 A 8/2021
CN 113262039 A 8/2021
CN 113349920 A 9/2021
CN 113476136 A 10/2021
CN 113545841 A 10/2021
CN 113558744 A 10/2021
CN 113598935 A 11/2021
CN 113633370 A 11/2021
CN 113648052 A 11/2021
CN 113662652 A 11/2021
CN 113729918 A 12/2021
CN 113749759 A 12/2021
CN 113768616 A 12/2021
CN 113796949 A 12/2021
CN 113813038 A 12/2021
CN 215018825 U 12/2021
CN 215018838 U 12/2021
CN 215130007 U 12/2021
CN 113904662 A 1/2022
CN 113907867 A 1/2022
CN 113907869 A 1/2022
CN 113965187 A 1/2022
CN 113967065 A 1/2022
CN 215458587 U 1/2022
CN 215458590 U 1/2022
CN 215528977 U 1/2022
CN 113995504 A 2/2022
CN 114010309 A 2/2022
CN 114027966 A 2/2022
CN 114041873 A 2/2022
CN 114052886 A 2/2022
CN 114081614 A 2/2022
CN 215688380 U 2/2022
CN 215739390 U 2/2022
CN 215874916 U 2/2022
CN 114145841 A 3/2022
CN 114191071 A 3/2022
CN 216021346 U 3/2022
CN 216060719 U 3/2022
CN 114259291 A 4/2022
CN 114271931 A 4/2022
CN 114305659 A 4/2022
CN 114343828 A 4/2022
CN 114343834 A 4/2022
CN 114362725 A 4/2022
CN 114366280 A 4/2022
CN 114366286 A 4/2022
CN 114376723 A 4/2022
CN 114404018 A 4/2022
CN 216167811 U 4/2022
CN 216257368 U 4/2022
CN 216257375 U 4/2022
CN 216317946 U 4/2022
CN 114469308 A 5/2022
CN 114469310 A 5/2022
CN 114469327 A 5/2022
CN 216417310 U 5/2022
CN 216455269 U 5/2022
CN 216570184 U 5/2022
CN 114587562 A 6/2022
CN 114601551 A 6/2022
CN 114601556 A 6/2022
CN 216675890 U 6/2022
CN 114711958 A 7/2022
CN 216876573 U 7/2022
CN 216962609 U 7/2022
CN 217014194 U 7/2022
CN 114848131 A 8/2022
CN 114852947 A 8/2022
CN 114869446 A 8/2022
CN 114869447 A 8/2022
CN 114869453 A 8/2022
CN 114869455 A 8/2022
CN 114903584 A 8/2022
CN 114903585 A 8/2022
CN 114948174 A 8/2022
CN 217186412 U 8/2022
CN 217286034 U 8/2022
CN 114983557 A 9/2022
CN 115005961 A 9/2022
CN 115040230 A 9/2022
CN 115040233 A 9/2022
CN 115089289 A 9/2022
CN 115120337 A 9/2022
CN 217338817 U 9/2022
CN 115153820 A 10/2022
CN 115177357 A 10/2022
CN 115177359 A 10/2022
CN 115192182 A 10/2022
CN 217660104 U 10/2022
CN 115252111 A 11/2022
CN 115281822 A 11/2022
CN 115300094 A 11/2022
CN 115317118 A 11/2022
CN 115363735 A 11/2022
CN 115381544 A 11/2022
CN 217886186 U 11/2022
CN 217907965 U 11/2022
CN 115414112 A 12/2022
CN 115420911 A 12/2022
CN 115444542 A 12/2022
CN 217987696 U 12/2022
CN 115568938 A 1/2023
CN 115607260 A 1/2023
CN 115622539 A 1/2023
CN 115645030 A 1/2023
CN 115670640 A 2/2023
CN 218474635 U 2/2023
CN 218500798 U 2/2023
CN 115733467 A 3/2023
CN 218606802 U 3/2023
CN 115969502 A 4/2023
CN 115969503 A 4/2023
CN 115969507 A 4/2023
CN 116026625 A 4/2023
CN 116058954 A 5/2023
CN 116158833 A 5/2023
CN 116158838 A 5/2023
CN 219048802 U 5/2023
CN 116218666 A 6/2023
CN 219271099 U 6/2023
CN 219271105 U 6/2023
CN 116407253 A 7/2023
CN 116458993 A 7/2023

(56) References Cited

FOREIGN PATENT DOCUMENTS

| | | | |
|---|---|---|---|
| CN | 219354137 | U | 7/2023 |
| CN | 219422945 | U | 7/2023 |
| CN | 116509533 | A | 8/2023 |
| CN | 116549093 | A | 8/2023 |
| CN | 116616885 | A | 8/2023 |
| CN | 116629075 | A | 8/2023 |
| CN | 116672064 | A | 9/2023 |
| CN | 116672073 | A | 9/2023 |
| CN | 116687551 | A | 9/2023 |
| CN | 116687567 | A | 9/2023 |
| CN | 116784972 | A | 9/2023 |
| CN | 116898561 | A | 10/2023 |
| CN | 116919568 | A | 10/2023 |
| CN | 116919574 | A | 10/2023 |
| CN | 116965919 | A | 10/2023 |
| CN | 117084777 | A | 11/2023 |
| CN | 117159128 | A | 12/2023 |
| CN | 117204939 | A | 12/2023 |
| CN | 117503318 | A | 2/2024 |
| CN | 117598774 | A | 2/2024 |
| CN | 117838282 | A | 4/2024 |
| CN | 117838283 | A | 4/2024 |
| CN | 117838292 | A | 4/2024 |
| CN | 117883178 | A | 4/2024 |
| CN | 117883179 | A | 4/2024 |
| CN | 117958948 | A | 5/2024 |
| CN | 117958954 | A | 5/2024 |
| CN | 118044876 | A | 5/2024 |
| CN | 118078411 | A | 5/2024 |
| CN | 118078412 | A | 5/2024 |
| CN | 118141300 | A | 6/2024 |
| CN | 118141499 | A | 6/2024 |
| CN | 221106018 | U | 6/2024 |
| CN | 118319468 | A | 7/2024 |
| CN | 118319473 | A | 7/2024 |
| CN | 118476854 | A | 8/2024 |
| CN | 118542728 | A | 8/2024 |
| CN | 118576308 | A | 9/2024 |
| CN | 118750150 | A | 10/2024 |
| CN | 118787437 | A | 10/2024 |
| EP | 0735842 | B1 | 3/1999 |
| EP | 2425871 | A2 | 3/2012 |
| EP | 2762195 | A2 | 8/2014 |
| EP | 3248561 | A1 | 11/2017 |
| EP | 3395277 | A1 | 10/2018 |
| EP | 3116408 | B1 | 12/2018 |
| EP | 3456278 | A2 | 3/2019 |
| EP | 3470109 | A1 | 4/2019 |
| EP | 3482679 | A1 | 5/2019 |
| EP | 2736434 | B1 | 2/2020 |
| EP | 3769710 | A1 | 1/2021 |
| EP | 3777743 | A1 | 2/2021 |
| EP | 3834758 | A1 | 6/2021 |
| EP | 3841997 | A1 | 6/2021 |
| EP | 3841999 | A1 | 6/2021 |
| EP | 3881760 | A1 | 9/2021 |
| EP | 3888550 | A1 | 10/2021 |
| EP | 3892220 | A1 | 10/2021 |
| EP | 3900659 | A1 | 10/2021 |
| EP | 3919014 | A1 | 12/2021 |
| EP | 3919015 | A1 | 12/2021 |
| EP | 3932349 | A1 | 1/2022 |
| EP | 3936068 | A1 | 1/2022 |
| EP | 3939529 | A1 | 1/2022 |
| EP | 3944829 | A1 | 2/2022 |
| EP | 3944830 | A1 | 2/2022 |
| EP | 3944831 | A1 | 2/2022 |
| EP | 3960105 | A1 | 3/2022 |
| EP | 3964153 | A1 | 3/2022 |
| EP | 3973906 | A1 | 3/2022 |
| EP | 3973907 | A1 | 3/2022 |
| EP | 3991680 | A2 | 5/2022 |
| EP | 4018950 | A1 | 6/2022 |
| EP | 4032489 | A1 | 7/2022 |
| EP | 4039210 | A1 | 8/2022 |
| EP | 4056134 | A1 | 9/2022 |
| EP | 4074272 | A1 | 10/2022 |
| EP | 4079244 | A1 | 10/2022 |
| EP | 4091564 | A1 | 11/2022 |
| EP | 4115831 | A1 | 1/2023 |
| EP | 4115832 | A1 | 1/2023 |
| EP | 4115833 | A1 | 1/2023 |
| EP | 4134030 | A1 | 2/2023 |
| EP | 4134031 | A2 | 2/2023 |
| EP | 4137078 | A1 | 2/2023 |
| EP | 4147659 | A1 | 3/2023 |
| EP | 4151168 | A2 | 3/2023 |
| EP | 4154834 | A1 | 3/2023 |
| EP | 4166106 | A1 | 4/2023 |
| EP | 4173581 | A1 | 5/2023 |
| EP | 4197467 | A1 | 6/2023 |
| EP | 4197468 | A1 | 6/2023 |
| EP | 4201351 | A1 | 6/2023 |
| EP | 4201352 | A1 | 6/2023 |
| EP | 4201356 | A2 | 6/2023 |
| EP | 4212120 | A1 | 7/2023 |
| EP | 4215138 | A1 | 7/2023 |
| EP | 4215139 | A1 | 7/2023 |
| EP | 4215140 | A1 | 7/2023 |
| EP | 4215141 | A2 | 7/2023 |
| EP | 4215142 | A1 | 7/2023 |
| EP | 4215143 | A1 | 7/2023 |
| EP | 4215144 | A1 | 7/2023 |
| EP | 4215145 | A1 | 7/2023 |
| EP | 4248894 | A2 | 9/2023 |
| EP | 4272676 | A1 | 11/2023 |
| EP | 4279002 | A1 | 11/2023 |
| EP | 4282364 | A1 | 11/2023 |
| EP | 4292547 | A1 | 12/2023 |
| EP | 4295797 | A1 | 12/2023 |
| EP | 4349291 | A1 | 4/2024 |
| EP | 4360574 | A1 | 5/2024 |
| EP | 4374809 | A1 | 5/2024 |
| EP | 4382059 | A1 | 6/2024 |
| EP | 4393423 | A1 | 7/2024 |
| EP | 4397263 | A1 | 7/2024 |
| EP | 4467091 | A1 | 11/2024 |
| EP | 4527914 | A1 | 3/2025 |
| GB | 2488603 | A | 9/2012 |
| JP | H1057321 | A | 3/1998 |
| JP | 2015211843 | A | 11/2015 |
| KR | 1020190027342 | A | 3/2019 |
| KR | 102311513 | B1 | 10/2021 |
| KR | 102343921 | B1 | 12/2021 |
| KR | 102346167 | B1 | 1/2022 |
| KR | 1020220049299 | A | 4/2022 |
| KR | 1020220093918 | A | 7/2022 |
| KR | 1020220167182 | A | 12/2022 |
| KR | 1020230002011 | A | 1/2023 |
| KR | 1020230003688 | A | 1/2023 |
| KR | 102532123 | B1 | 5/2023 |
| WO | 0023143 | A1 | 4/2000 |
| WO | 0023563 | A1 | 4/2000 |
| WO | 0107583 | A1 | 2/2001 |
| WO | 03092521 | A1 | 11/2003 |
| WO | 2005065284 | A2 | 7/2005 |
| WO | 2007001753 | A2 | 1/2007 |
| WO | 2007144004 | A1 | 12/2007 |
| WO | 2008048620 | A2 | 4/2008 |
| WO | 2008048632 | A1 | 4/2008 |
| WO | 2008062378 | A2 | 5/2008 |
| WO | 2008070413 | A2 | 6/2008 |
| WO | 2008070521 | A2 | 6/2008 |
| WO | 2008101086 | A2 | 8/2008 |
| WO | 2008101091 | A2 | 8/2008 |
| WO | 2009121009 | A2 | 10/2009 |
| WO | 2009134876 | A1 | 11/2009 |
| WO | 2009137800 | A2 | 11/2009 |
| WO | 2009155526 | A2 | 12/2009 |
| WO | 2010008834 | A2 | 1/2010 |
| WO | 2010014480 | A1 | 2/2010 |
| WO | 2010068795 | A2 | 6/2010 |
| WO | 2010080974 | A1 | 7/2010 |
| WO | 2010093692 | A2 | 8/2010 |

(56) References Cited

FOREIGN PATENT DOCUMENTS

| | | | |
|---|---|---|---|
| WO | 2010117806 | A1 | 10/2010 |
| WO | 2010120866 | A2 | 10/2010 |
| WO | 2010138919 | A2 | 12/2010 |
| WO | 2010151277 | A1 | 12/2010 |
| WO | 2011022674 | A2 | 2/2011 |
| WO | 2011028937 | A1 | 3/2011 |
| WO | 2011047387 | A2 | 4/2011 |
| WO | 2011081996 | A2 | 7/2011 |
| WO | 2011103096 | A2 | 8/2011 |
| WO | 2011103133 | A2 | 8/2011 |
| WO | 2011135294 | A1 | 11/2011 |
| WO | 2011161474 | A1 | 12/2011 |
| WO | 2012013243 | A1 | 2/2012 |
| WO | 2012051433 | A2 | 4/2012 |
| WO | 2012071526 | A2 | 5/2012 |
| WO | 2012082688 | A1 | 6/2012 |
| WO | 2012100184 | A2 | 7/2012 |
| WO | 2012100185 | A2 | 7/2012 |
| WO | 2012118660 | A2 | 9/2012 |
| WO | 2013019378 | A1 | 2/2013 |
| WO | 2013059913 | A1 | 5/2013 |
| WO | 2014022221 | A1 | 2/2014 |
| WO | 2014025394 | A1 | 2/2014 |
| WO | 2014028195 | A2 | 2/2014 |
| WO | 2014039320 | A1 | 3/2014 |
| WO | 2014195933 | A1 | 12/2014 |
| WO | 2015021113 | A1 | 2/2015 |
| WO | 2015073885 | A1 | 5/2015 |
| WO | 2015076864 | A1 | 5/2015 |
| WO | 2015103530 | A1 | 7/2015 |
| WO | 2015103574 | A1 | 7/2015 |
| WO | 2015171921 | A2 | 11/2015 |
| WO | 2015175570 | A1 | 11/2015 |
| WO | 2015175944 | A1 | 11/2015 |
| WO | 2015192018 | A1 | 12/2015 |
| WO | 2015192027 | A1 | 12/2015 |
| WO | 2016060983 | A1 | 4/2016 |
| WO | 2016073476 | A1 | 5/2016 |
| WO | 2016141096 | A1 | 9/2016 |
| WO | 2016149575 | A1 | 9/2016 |
| WO | 2016154371 | A1 | 9/2016 |
| WO | 2016161113 | A1 | 10/2016 |
| WO | 2016164930 | A1 | 10/2016 |
| WO | 2016178697 | A1 | 11/2016 |
| WO | 2016180934 | A1 | 11/2016 |
| WO | 2016201264 | A1 | 12/2016 |
| WO | 2016210437 | A1 | 12/2016 |
| WO | 2017024123 | A1 | 2/2017 |
| WO | 2017031372 | A1 | 2/2017 |
| WO | 2017116796 | A1 | 7/2017 |
| WO | 2017117582 | A1 | 7/2017 |
| WO | 2017200954 | A1 | 11/2017 |
| WO | 2017212257 | A1 | 12/2017 |
| WO | 2018010659 | A1 | 1/2018 |
| WO | 2018023132 | A1 | 2/2018 |
| WO | 2018050025 | A1 | 3/2018 |
| WO | 2018067999 | A1 | 4/2018 |
| WO | 2018075946 | A1 | 4/2018 |
| WO | 2018093261 | A1 | 5/2018 |
| WO | 2018102376 | A1 | 6/2018 |
| WO | 2018140473 | A1 | 8/2018 |
| WO | 2018140593 | A1 | 8/2018 |
| WO | 2018148053 | A1 | 8/2018 |
| WO | 2018160655 | A1 | 9/2018 |
| WO | 2018191113 | A1 | 10/2018 |
| WO | 2018191149 | A1 | 10/2018 |
| WO | 2018195650 | A1 | 11/2018 |
| WO | 2018200800 | A1 | 11/2018 |
| WO | 2018208795 | A1 | 11/2018 |
| WO | 2018224404 | A1 | 12/2018 |
| WO | 2019022816 | A1 | 1/2019 |
| WO | 2019027589 | A1 | 2/2019 |
| WO | 2019036549 | A1 | 2/2019 |
| WO | 2019055512 | A1 | 3/2019 |
| WO | 2019057665 | A1 | 3/2019 |
| WO | 2019075459 | A1 | 4/2019 |
| WO | 2019083727 | A1 | 5/2019 |
| WO | 2019083982 | A1 | 5/2019 |
| WO | 2019084381 | A1 | 5/2019 |
| WO | 2019084442 | A1 | 5/2019 |
| WO | 2019118436 | A1 | 6/2019 |
| WO | 2019121328 | A1 | 6/2019 |
| WO | 2019133608 | A1 | 7/2019 |
| WO | 2019135884 | A1 | 7/2019 |
| WO | 2019139878 | A1 | 7/2019 |
| WO | 2019143956 | A1 | 7/2019 |
| WO | 2019147619 | A1 | 8/2019 |
| WO | 2019152986 | A1 | 8/2019 |
| WO | 2019157359 | A1 | 8/2019 |
| WO | 2019164650 | A1 | 8/2019 |
| WO | 2019173309 | A1 | 9/2019 |
| WO | 2019185331 | A1 | 10/2019 |
| WO | 2019212827 | A1 | 11/2019 |
| WO | 2019217300 | A1 | 11/2019 |
| WO | 2019217317 | A1 | 11/2019 |
| WO | 2019217433 | A1 | 11/2019 |
| WO | 2019226222 | A1 | 11/2019 |
| WO | 2019226640 | A1 | 11/2019 |
| WO | 2019234133 | A1 | 12/2019 |
| WO | 2020014264 | A1 | 1/2020 |
| WO | 2020051241 | A1 | 3/2020 |
| WO | 2020057155 | A1 | 3/2020 |
| WO | 2020061192 | A1 | 3/2020 |
| WO | 2020061359 | A1 | 3/2020 |
| WO | 2020086588 | A1 | 4/2020 |
| WO | 2020086677 | A1 | 4/2020 |
| WO | 2020097276 | A1 | 5/2020 |
| WO | 2020114878 | A1 | 6/2020 |
| WO | 2020140440 | A1 | 7/2020 |
| WO | 2020190688 | A1 | 9/2020 |
| WO | 2020190691 | A1 | 9/2020 |
| WO | 2020190693 | A1 | 9/2020 |
| WO | 2020198165 | A1 | 10/2020 |
| WO | 2020206328 | A1 | 10/2020 |
| WO | 2020221485 | A1 | 11/2020 |
| WO | 2020236558 | A1 | 11/2020 |
| WO | 2020243389 | A1 | 12/2020 |
| WO | 2020257207 | A1 | 12/2020 |
| WO | 2021009648 | A1 | 1/2021 |
| WO | 2021018217 | A1 | 2/2021 |
| WO | 2021022673 | A1 | 2/2021 |
| WO | 2021030256 | A1 | 2/2021 |
| WO | 2021043779 | A1 | 3/2021 |
| WO | 2021044310 | A1 | 3/2021 |
| WO | 2021055604 | A1 | 3/2021 |
| WO | 2021102230 | A1 | 5/2021 |
| WO | 2021102297 | A1 | 5/2021 |
| WO | 2021108292 | A1 | 6/2021 |
| WO | 2021108312 | A1 | 6/2021 |
| WO | 2021111193 | A1 | 6/2021 |
| WO | 2021111194 | A1 | 6/2021 |
| WO | 2021111361 | A1 | 6/2021 |
| WO | 2021113463 | A1 | 6/2021 |
| WO | 2021116773 | A1 | 6/2021 |
| WO | 2021116774 | A1 | 6/2021 |
| WO | 2021119173 | A1 | 6/2021 |
| WO | 2021127558 | A1 | 6/2021 |
| WO | WO2021116775 | A1 | 6/2021 |
| WO | 2021130542 | A1 | 7/2021 |
| WO | 2021136976 | A1 | 7/2021 |
| WO | 2021136996 | A1 | 7/2021 |
| WO | 2021142368 | A1 | 7/2021 |
| WO | 2021144317 | A1 | 7/2021 |
| WO | 2021144318 | A1 | 7/2021 |
| WO | 2021150629 | A1 | 7/2021 |
| WO | 2021173215 | A1 | 9/2021 |
| WO | 2021181231 | A2 | 9/2021 |
| WO | 2021187154 | A1 | 9/2021 |
| WO | 2021195311 | A1 | 9/2021 |
| WO | 2021206975 | A1 | 10/2021 |
| WO | 2021216515 | A1 | 10/2021 |
| WO | 2021216750 | A1 | 10/2021 |
| WO | 2021236341 | A1 | 11/2021 |
| WO | 2021242541 | A1 | 12/2021 |

(56) References Cited

FOREIGN PATENT DOCUMENTS

WO 2021247500 A1 12/2021
WO 2021247738 A1 12/2021
WO 2021250538 A1 12/2021
WO 2021257397 A1 12/2021
WO 2021263007 A1 12/2021
WO 2022007490 A1 1/2022
WO 2022016081 A1 1/2022
WO 2022020478 A1 1/2022
WO 2022020580 A1 1/2022
WO 2022020591 A1 1/2022
WO 2022020592 A1 1/2022
WO 2022028337 A1 2/2022
WO 2022046534 A1 3/2022
WO 2022047187 A1 3/2022
WO 2022047333 A1 3/2022
WO 2022055961 A2 3/2022
WO 2022058830 A1 3/2022
WO 2022060425 A1 3/2022
WO 2022072384 A1 4/2022
WO 2022072385 A2 4/2022
WO 2022075866 A1 4/2022
WO 2022079235 A1 4/2022
WO 2022134713 A1 6/2022
WO 2022136464 A1 6/2022
WO 2022136918 A1 6/2022
WO 2022159595 A1 7/2022
WO 2022159665 A1 7/2022
WO 2022164750 A1 8/2022
WO 2022173875 A1 8/2022
WO 2022173939 A1 8/2022
WO 2022176202 A1 8/2022
WO 2022176203 A1 8/2022
WO 2022182939 A1 9/2022
WO 2022185246 A1 9/2022
WO 2022187096 A1 9/2022
WO 2022192459 A1 9/2022
WO 2022192522 A1 9/2022
WO 2022197994 A1 9/2022
WO 2022212064 A1 10/2022
WO 2022214870 A1 10/2022
WO 2022232802 A1 11/2022
WO 2022240718 A1 11/2022
WO 2022245409 A1 11/2022
WO 2022245793 A1 11/2022
WO 2022246011 A1 11/2022
WO 2022251163 A1 12/2022
WO 2022251249 A1 12/2022
WO 2022251429 A1 12/2022
WO 2022251447 A1 12/2022
WO 2022256218 A1 12/2022
WO 2022260723 A1 12/2022
WO 2022264147 A2 12/2022
WO 2022266043 A1 12/2022
WO 2023277488 A1 1/2023
WO 2023278577 A1 1/2023
WO 2023009548 A1 2/2023
WO 2023009569 A1 2/2023
WO 2023009586 A1 2/2023
WO 2023018741 A1 2/2023
WO 2023034319 A1 3/2023
WO 2023042196 A1 3/2023
WO 2023059507 A1 4/2023
WO 2023059509 A1 4/2023
WO 2023073564 A1 5/2023
WO 2023086778 A1 5/2023
WO 2023086865 A1 5/2023
WO 2023096859 A1 6/2023
WO 2023122100 A2 6/2023
WO 2023137042 A1 7/2023
WO 2023147319 A1 8/2023
WO 2023150215 A1 8/2023
WO 2023154186 A1 8/2023
WO 2023161492 A1 8/2023
WO 2023161796 A1 8/2023
WO 2023164644 A2 8/2023
WO 2023167747 A2 9/2023
WO 2023172773 A1 9/2023
WO 2023192054 A1 10/2023
WO 2023192056 A1 10/2023
WO 2023192863 A1 10/2023
WO 2023196773 A1 10/2023
WO 2023205577 A1 10/2023
WO 2023211915 A1 11/2023
WO 2023212185 A1 11/2023
WO 2023235150 A1 12/2023
WO 2023239966 A1 12/2023
WO 2023244854 A1 12/2023
WO 2023249987 A1 12/2023
WO 2023250356 A1 12/2023
WO 2024013601 A1 1/2024
WO 2024047215 A1 3/2024
WO 2024059795 A1 3/2024
WO 2024064601 A1 3/2024
WO 2024069495 A1 4/2024
WO 2024073615 A1 4/2024
WO 2024073765 A2 4/2024
WO 2024075034 A1 4/2024
WO 2024081749 A2 4/2024
WO 2024092173 A1 5/2024
WO 2024107387 A1 5/2024
WO 2024118327 A1 6/2024
WO 2024118748 A2 6/2024
WO 2024121740 A1 6/2024
WO 2024127133 A1 6/2024
WO 2024129292 A1 6/2024
WO 2024129293 A1 6/2024
WO 2024153994 A1 7/2024
WO 2024154068 A1 7/2024
WO 2024155619 A1 7/2024
WO 2024160553 A1 8/2024
WO 2024170972 A1 8/2024
WO 2024177757 A1 8/2024

OTHER PUBLICATIONS

Partial European Search Report issued in European Appln. No. 22190754.6 mailed Jan. 13, 2023.
Office Action issued in U.S. Appl. No. 17/521,107, mailed Nov. 10, 2025.
Extended European Search Report issued in European Appln. No. 22190754.6 mailed May 8, 2023.
Amendment filed in U.S. Appl. No. 17/885,990 on Jan. 7, 2026.
Amendment filed in U.S. Appl. No. 17/521,107 on Feb. 9, 2026.
Supplemental Amendment filed in U.S. Appl. No. 17/521,107 on Mar. 12, 2026.
Non-Final Office Action issued in U.S. Appl. No. 18/308,000 mailed Mar. 17, 2026.
Response to Non-Final Office Action filed in U.S. Appl. No. 17/521,107 on Jul. 31, 2025.
Office Action issued in U.S. Appl. No. 17/885,990 mailed Oct. 8, 2025.
Office Action issued in copending U.S. Appl. No. 17/399,381, mailed Jan. 18, 2024.
Amendment filed in copending U.S. Appl. No. 17/399,381 on Apr. 3, 2024.
Notice of Allowance issued in copending U.S. Appl. No. 17/399,381, mailed May 2, 2024.
Kottkamp et al. "Global multielectrode contact mapping plus ablation with a single catheter: Preclinical and preliminary experience in humans with atrial fibrillation." Journal of Cardiovascular Electrophysiology. 2017:1-10.
Mounsey. "A novel multielectrode combined mapping and ablation basket catheter: A future player in the atrial fibrillation ablation space?" Journal of Cardiovascular Electrophysiology. 2017:1-2.

* cited by examiner

SYSTEMS AND METHODS FOR TREATING TISSUE WITH PULSED FIELD ABLATION

CROSS-REFERENCE TO RELATED APPLICATIONS

This application is a continuation of U.S. application Ser. No. 17/399,381, filed Aug. 11, 2021, which claims the benefit of U.S. Provisional Application No. 63/065,714, filed Aug. 14, 2020, wherein the entire disclosure of each of these applications is hereby incorporated herein by reference.

TECHNICAL FIELD

Aspects of this disclosure generally are related to systems and methods for treating tissue using pulsed field ablation.

BACKGROUND

Cardiac surgery was initially undertaken using highly invasive open procedures. A sternotomy, which is a type of incision in the center of the chest that separates the sternum was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left or right atria to block various paths taken by the spurious electrical signals. Such lesions were originally created using incisions, but are now typically created by ablating the tissue with various techniques including radio-frequency (RF) energy, microwave energy, laser energy, and cryogenic techniques. Although RF ablation techniques are commonly employed in cardiac applications, possible complications may arise from the thermal energy that is delivered. For example, this thermal energy may cause direct damage to the target cardiac tissue including tissue charring and steam pops, thermal coagulation of blood which may lead to strokes, and damage to various anatomical structures proximate the heart such as the phrenic nerve or esophagus.

Recently, pulsed field ablation ("PFA") techniques have been investigated in various tissue ablation procedures. PFA is considered by some to be generally nonthermal in nature. In PFA, high voltage pulses with sub-second pulse durations are applied to target tissue. In some cases, the high voltage pulses rupture cell membranes by forming pores which allow leakage of cell contents, eventually resulting in cell death. When the PFA process is such that the formed pores are 'permanent' in nature, the PFA process is referred to as irreversible electroporation by some. In some cases, PFA shows a specificity for certain tissues. For example, it has been shown that tissue such as myocardium is highly susceptible to necrosis under the effects of PFA, while collateral structures such as the esophagus and phrenic nerve seem to be relatively resistant to injury.

Further, because PFA requires delivery of high voltage pulses in rapid succession, semiconductor switches typically are desirable to produce such pulses, since they can be operated at high speed. However, the present inventors recognized that semiconductor switches can be subject to failure, resulting in a short circuit through a failed switch, and thereby providing a potentially dangerous direct connection between the patient and a high voltage power source. Further still, the present inventors recognized that semiconductor switches have significant parasitic elements. For example, capacitance from input to output of a particular semiconductor switch may be approximately 100 pF. Since PFA pulses are generally of very short duration (e.g., <10 μs), they generally also have very short rise and fall times, and, since high voltages (e.g., 0.5 kV-3 kV) are involved, the voltage slew rate is very large. With the addition of the significant parasitic capacitances in semiconductor switches, significant current can flow through the switches that are nominally in the open (e.g., OFF) state.

The present inventors have recognized that these circumstances have been obstacles to developing semiconductor-based PFA systems. Further, the present inventors recognized that PFA systems can more effectively and expeditiously treat patients when such systems have many PFA electrodes, which allow for greater precision and area of treatment due to the large number of electrodes. However, the present inventors recognized that the above-discussed circumstances are exacerbated if extrapolated to multi-electrode PFA systems. For example, the present inventors considered that, with a PFA voltage of 2 kV, a pulse rise time of 0.5 μs, and an individual semiconductor parasitic capacitance of 100 pF, the current that may flow through each semiconductor switch that is nominally in the open (e.g., OFF) state is 0.4 A. In this example, the present inventors considered that, if 100 such semiconductor switches are present in a multi-electrode PFA system, the total undesired current that could flow through the electrodes and consequently the patient is 40 A, which may produce undesired physiological effects. Additionally, the present inventors recognized that this current 'loss' reduces the efficiency of the system.

In this regard, there is a need for PFA systems with improved safety, efficiency, and/or effectiveness.

SUMMARY

At least the above-discussed need is addressed and technical solutions are achieved in the art by various embodiments of the present invention. In some embodiments, a pulsed field ablation system may be summarized as including an output pulse generation circuit, and a high voltage pulse generation circuit electrically connected to the output pulse generation circuit and configured to deliver a high voltage pulse set to the output pulse generation circuit. According to some embodiments, the output pulse generation circuit may be configured to generate an output pulse set at least in response to the high voltage pulse set, the output pulse set deliverable to a set of selectable electrodes and configured to cause pulsed field ablation of tissue. According to various embodiments, each pulse in the output pulse set may have a rise time that is shorter than a rise time of at least one high voltage pulse in the high voltage pulse set.

According to some embodiments, the output pulse generation circuit may include a first capacitor and a second capacitor, the high voltage pulse generation circuit electrically connected to the first capacitor and the second capacitor to deliver the high voltage pulse set to the first capacitor and the second capacitor. According to some embodiments, the pulsed field ablation system may include a controller system communicatively connected to a circuit that includes the high voltage pulse generation circuit and the output pulse generation circuit. According to various embodiments, the output pulse generation circuit may include a first capacitor and a second capacitor, and the controller system is configured to cause the high voltage pulse generation circuit to deliver a first subset of the high voltage pulse set to the output pulse generation circuit to charge the first capacitor and the second capacitor. According to some embodiments, the first subset of the high voltage pulse set is less than all of the high voltage pulse set. In some embodiments, the controller system may be configured to cause the high voltage pulse generation circuit to deliver a second subset of the high voltage pulse set to the output pulse generation circuit to increase a voltage across a portion of the output pulse generation circuit to a magnitude greater than a magnitude of the first subset of the high voltage pulse set. According to various embodiments, the second subset of the high voltage pulse set is less than all of the high voltage pulse set, and the second subset of the high voltage pulse set is mutually exclusive with the first subset of the high voltage pulse set.

According to various embodiments, the output pulse generation circuit may include a first capacitor and a second capacitor, the high voltage pulse generation circuit electrically connected to the first capacitor and the second capacitor to deliver at least a first high voltage pulse in the high voltage pulse set to the first capacitor and the second capacitor. In some embodiments, the high voltage pulse set may include at least the first high voltage pulse and a second high voltage pulse. In some embodiments, the first high voltage pulse may have a polarity that is opposite to a polarity of the second high voltage pulse. In some embodiments, the high voltage pulse generation circuit may be electrically connected to the first capacitor and the second capacitor to deliver the second high voltage pulse to the first capacitor and the second capacitor. In some embodiments, each output pulse of the output pulse set is an output voltage pulse, and the controller system may be configured to cause the output pulse generation circuit to deliver each output voltage pulse of the output pulse set with a magnitude that is greater than each of a magnitude of the first high voltage pulse and a magnitude of the second high voltage pulse. In some embodiments, the controller system may be configured to cause the output pulse generation circuit to at least partially discharge the first capacitor and the second capacitor during at least part of the delivery of the second high voltage pulse to the first capacitor and the second capacitor. In some embodiments, the controller system may be configured to cause the high voltage pulse generation circuit to deliver the second high voltage pulse to the first capacitor and the second capacitor after the first high voltage pulse has been delivered to the first capacitor and the second capacitor.

In some embodiments, the pulsed field ablation system may include a controller system communicatively connected to a circuit including the high voltage pulse generation circuit and the output pulse generation circuit. In some embodiments, the controller system may be configured to cause the high voltage pulse generation circuit to deliver at least the first high voltage pulse to the output pulse generation circuit to charge the first capacitor and the second capacitor. In some embodiments, the controller system may be configured to cause, during at least part of the delivery of at least the second high voltage pulse to the output pulse generation circuit, a voltage across a portion of the output pulse generation circuit to increase to a magnitude greater than a magnitude of the first high voltage pulse. In some embodiments, the portion of the output pulse generation circuit may be an output bus electrically connected to the set of selectable electrodes. In some embodiments, the controller system may be configured to cause the voltage across the portion of the output pulse generation circuit to increase to the magnitude greater than the magnitude of the first high voltage pulse after causing each of the first capacitor and the second capacitor to be charged in response to delivery of at least the first high voltage pulse by the high voltage pulse generation circuit to the output pulse generation circuit. In some embodiments, each output pulse of the output pulse set is an output voltage pulse, and the controller system may be configured to cause, during the delivery of at least part of the second high voltage pulse, the output pulse generation circuit to deliver each output voltage pulse of the output pulse set with a magnitude that is greater than a magnitude of the first high voltage pulse. In some embodiments, each output pulse of the output pulse set is an output voltage pulse, and the controller system may be configured to cause, after the voltage across the portion of the output pulse generation circuit is increased to the magnitude greater than the magnitude of the first high voltage pulse, the output pulse generation circuit to deliver each output voltage pulse of the output pulse set with a magnitude that is greater than the magnitude of the first high voltage pulse.

According to some embodiments, the at least one high voltage pulse in the high voltage pulse set may include the second high voltage pulse, such that each pulse in the output pulse set has a rise time that is shorter than a rise time of at least the second high voltage pulse in the high voltage pulse set.

According to various embodiments, the output pulse generation circuit may include a first capacitor and a second capacitor, the high voltage pulse generation circuit electrically connected to the first capacitor and the second capacitor to deliver at least a first high voltage pulse in the high voltage pulse set to the first capacitor and the second capacitor. In some embodiments, the high voltage pulse set may include at least the first high voltage pulse and a second high voltage pulse. According to some embodiments, energy is stored in each of the first capacitor and the second capacitor in response to the delivery of the first high voltage pulse to the first capacitor and the second capacitor, and each output pulse of the output pulse set includes a portion of the energy stored in each of the first capacitor and the second capacitor. In some embodiments, each of the first capacitor and the second capacitor is a Class-Y capacitor. In some embodiments, each of the first capacitor and the second capacitor is either a Class-Y1 capacitor or a Class-Y2 capacitor.

According to various embodiments, the output pulse generation circuit may include a first capacitor and a second capacitor, the high voltage pulse generation circuit electrically connected to the first capacitor and the second capacitor to deliver at least a first high voltage pulse in the high voltage pulse set to the first capacitor and the second capacitor. According to some embodiments, the pulsed field ablation system may include a controller system communicatively connected to a circuit that includes the high voltage pulse generation circuit and the output pulse generation circuit. In some embodiments, the high voltage pulse generation circuit may include a first group of switches electrically connected to the first capacitor and the second capacitor, and a second group of switches electrically connected to the first capacitor and the second capacitor. In some embodiments, the high voltage pulse set may include at least a first high voltage pulse and a second high voltage pulse. In some embodiments, the controller system may be configured to cause (a) each switch in the first group of switches to be in a respective NON-OPEN state with each switch in the second group of switches in a respective OPEN state during a delivery of the first high voltage pulse to the output pulse generation circuit. In some embodiments, the controller system may be configured to cause (b) each switch in the second group of switches to be in a respective NON-OPEN state with each switch in the first group of switches in a respective OPEN state during a delivery of the second high voltage pulse to the output pulse generation circuit. According to various embodiments, each respective OPEN state for each switch in the first group of switches and for each switch in the second group of switches is configured to prevent flow of electric current through the respective switch. According to various embodiments, each respective NON-OPEN state for each switch in the first group of switches and for each switch in the second group of switches is configured to allow a respective level of electric current to be deliverable through the respective switch, the respective level of electric current deliverable through the respective switch in the respective NON-OPEN state greater than any electric current deliverable through the respective switch in the respective OPEN state.

According to various embodiments, the high voltage pulse generation circuit may include a high voltage supply. In some embodiments, to generate the first high voltage pulse, the controller system may be configured to cause (c) each switch in the first group of switches to switch between the respective OPEN state and the respective NON-OPEN state, with each switch in the second group of switches in the respective OPEN state. In some embodiments, to generate the second high voltage pulse, the controller system may be configured to cause (d) each switch in the second group of switches to switch between the respective OPEN state and the respective NON-OPEN state, with each switch in the first group of switches in the respective OPEN state. According to some embodiments, the controller system may be configured to cause (b) after causing (a), and the at least one high voltage pulse in the high voltage set includes the second high voltage pulse, such that each pulse in the output pulse set has a rise time that is shorter than a rise time of at least the second high voltage pulse in the high voltage pulse set. According to some embodiments, the controller system may be configured to cause both the first capacitor and the second capacitor to concurrently at least partially discharge, and the controller system may be configured to cause (a) and (b) prior to the concurrent discharge of both the first capacitor and the second capacitor.

According to some embodiments, the pulsed field ablation system may include an electric current control circuit electrically connected to at least one switch in the first group of switches to control electric current deliverable through the first group of switches to control the rise time of the first high voltage pulse. In some embodiments, the electric current control circuit electrically connected to at least one switch in the first group of switches is a closed-loop electric current control circuit. In some embodiments, the pulsed field ablation system may include an electric current control circuit electrically connected to at least one switch in the second group of switches to control electric current deliverable through the second group of switches to control the rise time of the second high voltage pulse. In some embodiments, the electric current control circuit electrically connected to at least one switch in the second group of switches is a closed-loop electric current control circuit.

According to various embodiments, the respective NON-OPEN state for a first switch in the first group of switches or the second group of switches is a FIRST NON-OPEN state associated with the first switch. In some embodiments, the controller system may be configured to cause at least the first switch to switch between the respective OPEN state associated with the first switch and the FIRST NON-OPEN state associated with the first switch with each switch in the other of the first group of switches and the second group of switches to which the first switch does not belong in the OPEN state. In some embodiments, the controller system may be configured to cause electric current deliverable through the first switch to be controlled. In some embodiments, the FIRST NON-OPEN state associated with the first switch is configured to control the electric current deliverable through the first switch to a first level to control the rise time of the at least one high voltage pulse of the set of high voltage pulses. In some embodiments, the first switch may be configurable to switch between the respective OPEN state associated with the first switch and a SECOND NON-OPEN state associated with the first switch, the SECOND NON-OPEN state associated with the first switch configured to control electric current deliverable through the first switch to a second level greater than the first level. In some embodiments, the SECOND NON-OPEN state associated with the first switch may be a CLOSED state of the first switch, the CLOSED state configured to allow maximum or substantially maximum electric current to be deliverable through the first switch. In some embodiments, the controller system may be configured to cause the first switch to switch between the FIRST NON-OPEN state and the SECOND NON-OPEN state after causing (a) and (b). In some embodiments, the controller system may be configured to cause the output pulse generation circuit to discharge the first capacitor and the second capacitor with the first switch in the SECOND NON-OPEN state. In some embodiments, the controller system may be configured to cause the output pulse generation circuit to generate the output pulse set with the first switch in the SECOND NON-OPEN state.

According to some embodiments, the first switch may be a semiconductor switch including a transistor. In some embodiments, the transistor may be a bipolar junction transistor.

In some embodiments, the transistor may be an insulated-gate bipolar transistor. In some embodiments, the transistor may be a field effect transistor. In some embodiments, the transistor may be a MOSFET.

According to some embodiments, the controller system may be configured to cause, with each switch in the other of the first group of switches and the second group of switches to which the first switch does not belong in the respective OPEN state, at least a second switch in the first group of switches or the second group of switches to which the first switch belongs to switch between the respective OPEN state and a SECOND NON-OPEN state associated with the second switch, the SECOND NON-OPEN state associated with the second switch configured to control electric current deliverable though the second switch to a second level, the second level greater than the first level.

According to some embodiments, the first group of switches may be electrically connected in series, at least when the controller system causes (a). In some embodiments, the second group of switches may be electrically connected in series, at least when the controller system causes (b). In some embodiments, the first group of switches and the second group of switches may be arranged in a full bridge configuration.

According to various embodiments, the output pulse generation circuit may include a plurality of output switch sets electrically connected to the first capacitor and the second capacitor to receive energy therefrom, the plurality of output switch sets electrically connected to the set of selectable electrodes. In some embodiments, the controller system may be configured to cause (a) to increase voltage across the first capacitor and the second capacitor to a first magnitude. In some embodiments, the controller system may be configured to cause (b) to increase voltage across at least a first output switch set of the plurality of output switch sets to a second magnitude greater than the first magnitude. In some embodiments, the at least one high voltage pulse in the high voltage pulse set may include the second high voltage pulse, such that each pulse in the output pulse set has a rise time that is shorter than a rise time of at least the second high voltage pulse in the high voltage pulse set. In some embodiments, the controller system may be configured to cause the output pulse generation circuit to generate the pulses in the output pulse set by switching each output switch of at least one output switch of selected output switch sets of the plurality of output switch sets between an OPEN state associated with the output switch configured to prevent flow of electric current therethrough, and a CLOSED state associated with the output switch configured to allow maximum or substantially maximum electric current to be deliverable therethrough. In some embodiments, each output switch of the plurality of output switch sets may be a semiconductor switch. In some embodiments, at least some of the switches in each output switch set of the plurality of output switch sets may be arranged in a half bridge configuration.

According to some embodiments, the pulsed field ablation system may include a controller system communicatively connected to a circuit that includes the high voltage pulse generation circuit and the output pulse generation circuit. In some embodiments, the high voltage pulse generation circuit may include a transformer and at least a first switch electrically connected to the primary of the transformer. In some embodiments, the output pulse generation circuit may be electrically connected to the secondary of the transformer. According to some embodiments, the first switch may be operable to switch between (e) an OPEN state configured to provide a first voltage across the first switch, and (f) a NON-OPEN state configured to provide a second voltage across the first switch, the second voltage across the first switch in the NON-OPEN state less than the first voltage across the first switch in the OPEN state. According to some embodiments, the controller system may be configured to cause the first switch to switch between the OPEN state and the NON-OPEN state to cause voltage across the first switch to be controlled to a particular level to control the rise time of the at least one high voltage pulse of the high voltage pulse set. In some embodiments, the first switch may be a semiconductor switch including a transistor. In some embodiments, the pulsed field ablation system may include a voltage control circuit electrically connected to the first switch to control voltage across the first switch to control the rise time of the at least one high voltage pulse of the high voltage pulse set. In some embodiments, the voltage control circuit may be a closed-loop voltage control circuit.

Various other pulsed field ablation systems may include combinations and subcombinations of those described above.

According to some embodiments, a pulsed field ablation system may be summarized as including a high voltage supply, a controller system, and a circuit communicatively connected to the controller system, the circuit electrically connected to the high voltage supply to receive input voltage therefrom. According to some embodiments, the circuit may include a first plurality of capacitors electrically connected to the high voltage supply via a plurality of switches. According to some embodiments, the circuit may include at least a first output switch set electrically connecting the first plurality of the capacitors to a plurality of selectable pulsed field ablation electrodes. According to various embodiments, the controller system may be configured to cause (i) switching of at least some of the plurality of switches to produce a first switch configuration in which the first plurality of capacitors is in a first series circuit configured to charge the first plurality of capacitors. According to various embodiments, the controller system may be configured to cause (ii) switching, subsequent (i), of at least some of the plurality of switches to produce a second switch configuration in which the first plurality of capacitors is in a second series circuit configured to apply an output voltage across at least the first output switch set, the output voltage greater than the input voltage, the second series circuit different than the first series circuit. According to various embodiments, the controller system may be configured to cause (iii) switching of at least one output switch of the output switches of at least the first output switch set to generate a plurality of output pulse sets at least from energy stored at least in the first plurality of capacitors, each output pulse set in the plurality of output pulse sets configured to cause pulsed field ablation.

In some embodiments, electric current through the first plurality of capacitors in the second series circuit may be in an opposite direction to electric current through the first plurality of capacitors in the first series circuit.

According to some embodiments, in the first switch configuration, each switch in a first switch set of the plurality of switches may be in a respective NON-OPEN state configured to allow a respective level of electric current to be deliverable through the switch in the first switch set, and in the second switch configuration, each switch in the first switch set may be in a respective OPEN state configured to prevent flow of electric current through the switch in the first switch set, the respective level of electric current deliverable through the switch in the first switch set in the respective NON-OPEN state greater than any electric current deliverable through the switch in the first switch set in the respective OPEN state. In some embodiments, in the first switch configuration, each switch in a second switch set of the plurality of switches may be in a respective OPEN state configured to prevent flow of electric current through the switch in the second switch set, and in the second switch configuration, each switch in the second switch set may be in a respective NON-OPEN state configured to allow a respective level of electric current to be deliverable through the switch in the second switch set, the respective level of electric current deliverable through the switch in the second switch set in the respective NON-OPEN state greater than any electric current deliverable through the switch in the second switch set in the respective OPEN state.

In various embodiments, at least a first switch in the first switch set may be a semiconductor switch, and the pulsed field ablation system may include an electric current control circuit electrically connected to the first switch and configured to control electric current through the first switch.

In some embodiments, at least a first switch in the first switch set may be a semiconductor switch including a transistor. In some embodiments, the transistor may be a bipolar junction transistor. In some embodiments, the transistor may be an insulated-gate bipolar transistor. In some embodiments, the transistor may be a field effect transistor. In some embodiments, the transistor may be a MOSFET. In some embodiments, the plurality of switches is arranged in a full bridge configuration.

According to various embodiments, the circuit may include one or more second capacitors, the plurality of switches electrically connecting the one or more second capacitors to the first plurality of capacitors to charge the first plurality of capacitors with charge stored in the one or more second capacitors. In some embodiments, voltage across each capacitor of the first plurality of capacitors may increase, and concurrently, voltage across each capacitor of the one or more second capacitors may decrease in response to the controller system causing (i).

According to various embodiments, the controller system may be configured to repeat (i) and (ii) with each successive output pulse set of the plurality of output pulse sets that is generated. In some embodiments, voltage across each capacitor of the first plurality of capacitors may increase, and concurrently, voltage across each capacitor of the one or more second capacitors may decrease in response to each occurrence of the controller system causing (i). In some embodiments, voltage across the first plurality of capacitors may incrementally increase, and concurrently, voltage across the one or more second capacitors may incrementally decrease with each successive output pulse set of the plurality of output pulse sets that is generated. In some embodiments, a sum of (iv) the voltage across each capacitor of the first plurality of capacitors and (v) the voltage across each capacitor of the one or more second capacitors may remain constant or substantially or nominally constant in various embodiments with each successive output pulse set of the plurality of output pulse sets that is generated.

According to various embodiments, the circuit may include a plurality of sensing circuits, each sensing circuit of the plurality of sensing circuits electrically connected to a respective capacitor of the first plurality of capacitors. In some embodiments, the controller system may be configured to determine, based at least on a signal set provided by a particular sensing circuit of the plurality of sensing circuits, a capacitance of the respective capacitor of the first plurality of capacitors. In some embodiments, the signal set provided by the particular sensing circuit of the plurality of sensing circuits may include a signal provided by a voltage sensing portion of the particular sensing circuit. In some embodiments, the circuit may include an electric current sensing circuit configured to sense electric current through each capacitor of the first plurality of capacitors. In some embodiments, the controller system may be configured to determine, based at least on a signal set provided by the electric current sensing circuit, the capacitance of each respective capacitor of the first plurality of capacitors. In some embodiments, the particular sensing circuit may include a plurality of redundant sensing circuits, and the controller system may be configured to determine multiple capacitance values for each respective capacitor of the first plurality of capacitors, each capacitance value of the multiple capacitance values determined based at least on a signal set provided by a respective one of the redundant sensing circuits of the particular sensing circuit. In some embodiments, the controller system may be configured to individually determine the capacitance of each respective capacitor of the first plurality of capacitors, each capacitance determined based at least on a signal set provided by the respective sensing circuit of the plurality of sensing circuits.

Various other pulsed field ablation systems may include combinations and subcombinations of those described above.

According to various embodiments, a pulsed field ablation system may be summarized as including a high voltage supply, a controller system, and a circuit communicatively connected to the controller system, the circuit electrically connected to the high voltage supply to receive input voltage therefrom. According to some embodiments, the circuit may include a first plurality of capacitors electrically connected to the high voltage supply via a plurality of switches. According to various embodiments, the circuit may include at least a first output switch set electrically connecting the first plurality of the capacitors to a plurality of selectable pulsed field ablation electrodes. According to various embodiments, the controller system may be configured to cause (i) switching of at least some of the plurality of switches to produce a first switch configuration in which the first plurality of capacitors is in a first series circuit.

According to various embodiments, the controller system may be configured to cause (ii) switching, subsequent (i), of at least some of the plurality of switches to produce a second switch configuration in which the first plurality of capacitors is in a second series circuit, wherein the second series circuit is configured to cause electric current through the first plurality of capacitors to be in an opposite direction than electric current through the first plurality of capacitors in the first series circuit. According to various embodiments, the controller system may be configured to cause (iii) switching of at least one output switch of at least the first output switch set to generate a plurality of output pulse sets at least from energy stored at least in the first plurality of capacitors, each output pulse set of the plurality of output pulse sets configured to cause pulsed field ablation.

Various embodiments of the present invention may include systems, devices, or machines that are or include combinations or subsets of any one or more of the systems, devices, or machines and associated features thereof summarized above or otherwise described herein.

Further, all or part of any one or more of the systems, devices, or machines summarized above or otherwise described herein or combinations or subcombinations thereof may implement or execute all or part of any one or more of the processes or methods described herein or combinations or subcombinations thereof.

For example, in some embodiments, a method may, according to some embodiments, be summarized as including delivering a high voltage pulse set from a high voltage pulse generation circuit to an output pulse generation circuit, and generating an output pulse set from the output pulse generation circuit at least in response to the high voltage pulse set. According to various embodiments, the output pulse set is delivered to a set of selected electrodes configured to cause pulsed field ablation of tissue, each pulse in the output pulse set having a rise time that is shorter than a rise time of at least one high voltage pulse in the high voltage pulse set.

For another example, in some embodiments, a method may be summarized as including receiving, from a high voltage supply, an input voltage, the input voltage received at least at a circuit comprising a first plurality of capacitors and comprising at least a first output switch set electrically connecting the first plurality of capacitors to a plurality of selectable pulsed field ablation electrodes, the first plurality of capacitors electrically connected to the high voltage supply via a plurality of switches. In some embodiments, the method may include switching of at least some of the plurality of switches to produce a first switch configuration in which the first plurality of capacitors is in a first series circuit to charge the first plurality of capacitors. In some embodiments, the method includes switching, subsequent to the switching to produce the first switch configuration, of at least some of the plurality of switches to produce a second switch configuration in which the first plurality of capacitors is in a second series circuit to apply an output voltage across at least the first output switch set, the output voltage greater than the input voltage, and the second series circuit different than the first series circuit. In some embodiments, the method may include switching of at least one output switch of at least the first output switch set to generate a plurality of output pulse sets at least from energy stored at least in the first plurality of capacitors, each output pulse set in the plurality of output pulse sets configured to cause pulsed field ablation.

For another example, in some embodiments, a method may be summarized as including receiving, from a high voltage supply, an input voltage, the input voltage received at least at a circuit including a first plurality of capacitors and including at least a first output switch set electrically connecting the first plurality of capacitors to a plurality of selectable pulsed field ablation electrodes, the first plurality of capacitors electrically connected to the high voltage supply via a plurality of switches. According to various embodiments, the method may include causing switching of at least some of the plurality of switches to produce a first switch configuration in which the first plurality of capacitors is in a first series circuit. According to various embodiments, the method may include causing switching, subsequent to the switching to produce the first switch configuration, of at least some of the plurality of switches to produce a second switch configuration in which the first plurality of capacitors is in a second series circuit. In some embodiments, electric current through the first plurality of capacitors in the second series circuit may be in an opposite direction to electric current through the first plurality of capacitors in the first series circuit. According to various embodiments, the method may include causing switching of at least one output switch of at least the first output switch set to generate a plurality of output pulse sets at least from energy stored at least in the first plurality of capacitors, each output pulse set in the plurality of output pulse sets configured to cause pulsed field ablation.

It should be noted that various embodiments of the present invention include variations of the methods or processes summarized above or otherwise described herein (including the figures) and, accordingly, are not limited to the actions described or shown in the figures or their ordering, and not all actions shown or described are required according to various embodiments. According to various embodiments, such methods may include more or fewer actions and different orderings of actions. Any of the features of all or part of any one or more of the methods or processes summarized above or otherwise described herein (including the figures) may be combined with any of the other features of all or part of any one or more of the methods or processes summarized above or otherwise described herein or shown in the figures.

In addition, a computer program product may be provided that comprises program code portions for performing some or all of any one or more of the methods or processes and associated features thereof described herein, when the computer program product is executed by a computer or other computing device or device system. Such a computer program product may be stored on one or more computer-readable storage mediums, also referred to as one or more computer-readable data storage mediums.

For example, in some embodiments, one or more computer-readable mediums are provided, the one or more computer-readable mediums storing a program executable by a controller system communicatively connected to a circuit including a high voltage pulse generation circuit and an output pulse generation circuit electrically connected to the high voltage pulse generation circuit. According to various embodiments, the program may include delivering instructions configured to cause a delivery of a high voltage pulse set from the high voltage pulse generation circuit to the output pulse generation circuit, and generating instructions configured to cause generation of an output pulse set from the output pulse generation circuit at least in response to the high voltage pulse set, the output pulse set deliverable to a set of selectable electrodes and configured to cause pulsed field ablation of tissue, each pulse in the output pulse set having a rise time that is shorter than a rise time of at least one high voltage pulse in the high voltage pulse set. According to some embodiments, the one or more computer-readable mediums are one or more non-transitory computer-readable mediums.

For another example, in some embodiments, one or more computer-readable mediums are provided, the one or more computer-readable mediums storing a program executable by a controller system communicatively connected to a circuit electrically connected to a high voltage supply to receive input voltage therefrom. According to various embodiments, the circuit may include a first plurality of capacitors electrically connected to the high voltage supply via a plurality of switches and may include at least a first output switch set electrically connecting the first plurality of the capacitors to a plurality of selectable pulsed field ablation electrodes. According to various embodiments, the program may include first switching instructions configured to cause switching of at least some of the plurality of switches to produce a first switch configuration in which the first plurality of capacitors is in a first series circuit configured to charge the first plurality of capacitors. According to various embodiments, the program may include second switching instructions configured to cause switching, subsequent to execution of the first switching instructions, of at least some of the plurality of switches to produce a second switch configuration in which the first plurality of capacitors is in a second series circuit configured to apply an output voltage across at least the first output switch set, the output voltage greater than the input voltage, and the second series circuit different than the first series circuit. According to various embodiments, the program may include third switching instructions configured to cause switching of at least one output switch of at least the first output switch set to generate a plurality of output pulse sets at least from energy stored at least in the first plurality of capacitors, each output pulse set in the plurality of output pulse sets configured to cause pulsed field ablation. In some embodiments, the one or more computer-readable mediums may be one or more non-transitory computer-readable mediums.

For another example, in some embodiments, one or more computer-readable mediums are provided, the one or more computer-readable mediums storing a program executable by a controller system communicatively connected to a circuit electrically connected to a high voltage supply to receive input voltage therefrom. In some embodiments, the circuit may include a first plurality of capacitors electrically connected to the high voltage supply via a plurality of switches. In some embodiments, the circuit may include at least a first output switch set electrically connecting the first plurality of the capacitors to a plurality of selectable pulsed field ablation electrodes. According to various embodiments, the program may include first switching instructions configured to cause switching of at least some of the plurality of switches to produce a first switch configuration in which the first plurality of capacitors is in a first series circuit. According to various embodiments, the program may include second switching instructions configured to cause switching, subsequent to execution of the first switching instructions, of at least some of the plurality of switches to produce a second switch configuration in which the first plurality of capacitors is in a second series circuit. In some embodiments, the second series circuit may be configured to cause electric current through the first plurality of capacitors to be in an opposite direction than electric current through the first plurality of capacitors in the first series circuit. According to various embodiments, the program may include third switching instructions configured to cause switching of at least one output switch of at least the first output switch set to generate a plurality of output pulse sets at least from energy stored at least in the first plurality of capacitors, each output pulse set in the plurality of output pulse sets configured to cause pulsed field ablation. In some embodiments, the one or more computer-readable mediums may be one or more non-transitory computer-readable mediums.

In some embodiments, each of any of one or more of the computer-readable (data storage) medium systems (also referred to as processor-accessible memory device systems) described herein is a non-transitory computer-readable (or processor-accessible) data storage medium system (or memory device system) including or consisting of one or more non-transitory computer-readable (or processor-accessible) storage mediums (or memory devices) storing the respective program(s) which may configure a data processing device system to execute some or all of any of one or more of the methods or processes described herein.

Further, any of all or part of one or more of the methods or processes and associated features thereof discussed herein may be implemented or executed on or by all or part of a device system, apparatus, or machine, such as all or a part of any of one or more of the systems, apparatuses, or machines described herein or a combination or subcombination thereof.

BRIEF DESCRIPTION OF THE DRAWINGS

It is to be understood that the attached drawings are for purposes of illustrating aspects of various embodiments and may include elements that are not to scale.

DETAILED DESCRIPTION

Figure 1:
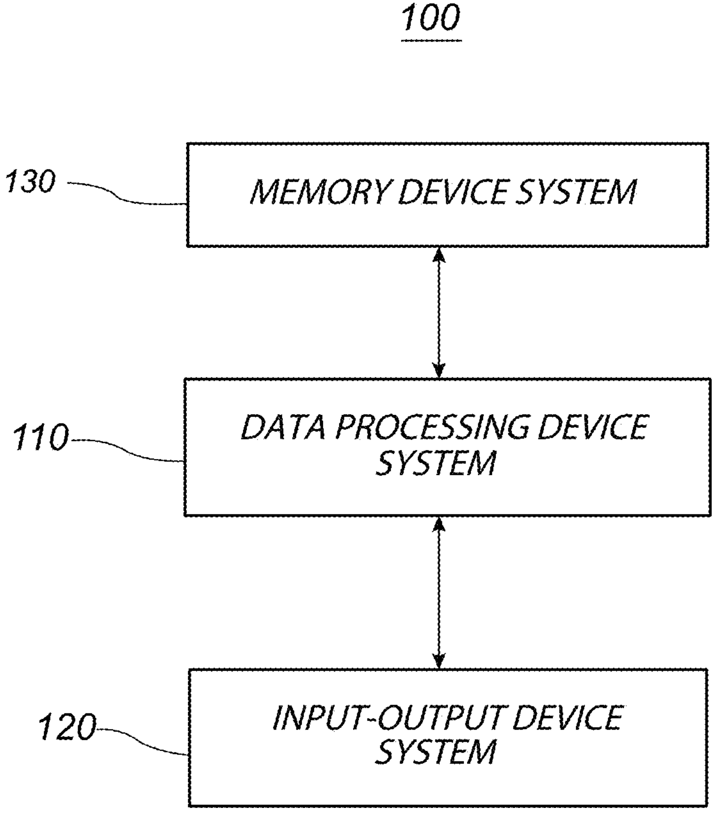
FIG. 1 includes a schematic representation of a pulsed field ablation system or a controller system thereof according to various example embodiments, the pulsed field ablation system including a data processing device system, an input-output device system, and a memory device system.

At least some embodiments of the present invention improve upon safety, efficiency, and effectiveness of pulsed field ablation ("PFA") systems, and, particularly, in some embodiments, PFA systems that employ many PFA electrodes or transducers. In some embodiments, rise time of one or more intermediate high voltage pulses is controlled (e.g., relatively increased) to relatively reduce the pulse(s) slew rate(s), such that one or more PFA output pulses generated in response to the one or more intermediate high voltage pulses have a shorter rise time than that of the one or more intermediate high voltage pulses. Such an output pulse generation configuration, among other benefits, limits the effects of parasitic capacitances present in switches (e.g., semiconductor switches) that produce the output pulses. In some embodiments, various capacitor configurations are provided in a PFA output pulse generation circuit in order to, among other benefits, reduce risk that a patient is directly connected to direct current. Such configurations, among other benefits, also can at least limit the effects of parasitic capacitances present in implicated semiconductor switches. In some embodiments, at least some of these and other capacitor configurations are configured to increase voltage of output PFA pulses, thereby allowing an electrically connected high voltage supply to the respective capacitor configuration to operate at a lower voltage, which may increase safety and efficiency of operation, among other benefits. Some embodiments of the present invention also provide one or more capacitor configurations configured to provide voltage droop prevention or reduction to support the high frequency of voltage pulses utilized in PFA systems, where such high frequency of voltage pulses can limit the time available to charge capacitors such that droop prevention configurations may be particularly suitable in some contexts. Some embodiments of the present invention provide capacitor sensing circuits with an electrical disconnect operable, in the event that a capacitor state is not in an acceptable range, to further reduce the risk of potential harm to a patient, among other benefits. It should be noted that the invention is not limited to these or any other examples provided herein, which are referred to for purposes of illustration only.

In this regard, in the descriptions herein, certain specific details are set forth in order to provide a thorough understanding of various embodiments of the invention. However, one skilled in the art will understand that the invention may be practiced at a more general level without one or more of these details. In other instances, well-known structures have not been shown or described in detail to avoid unnecessarily obscuring descriptions of various embodiments of the invention.

Any reference throughout this specification to "one embodiment", "an embodiment", "an example embodiment", "an illustrated embodiment", "a particular embodiment", and the like means that a particular feature, structure or characteristic described in connection with the embodiment is included in at least one embodiment. Thus, any appearance of the phrase "in one embodiment", "in an embodiment", "in an example embodiment", "in this illustrated embodiment", "in this particular embodiment", or the like in this specification is not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects. In some embodiments, the word "subset" is intended to mean a set having the same or fewer elements of those present in the subset's parent or superset. In other embodiments, the word "subset" is intended to mean a set having fewer elements of those present in the subset's parent or superset. In this regard, when the word "subset" is used, some embodiments of the present invention utilize the meaning that "subset" has the same or fewer elements of those present in the subset's parent or superset, and other embodiments of the present invention utilize the meaning that "subset" has fewer elements of those present in the subset's parent or superset.

Further, the phrase "at least" is or may be used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase, 'based at least on A' includes A as well as the possibility of one or more other additional elements besides A. In the same manner, the phrase, 'based on A' includes A, as well as the possibility of one or more other additional elements besides A. However, the phrase, 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase, 'configured only to A' means a configuration to perform only A.

The word "device", the word "machine", the word "system", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified according to various embodiments that a device or machine or device system resides entirely within a same housing to exclude embodiments where the respective device, machine, system, or device system resides across different housings. The word "device" may equivalently be referred to as a "device system" in some embodiments.

Further, the phrase "in response to" may be used in this disclosure. For example, this phrase may be used in the following context, where an event A occurs in response to the occurrence of an event B. In this regard, such phrase includes, for example, that at least the occurrence of the event B causes or triggers the event A.

The phrase "pulsed field ablation" ("PFA") as used in this disclosure refers to an ablation method which employs high voltage pulse delivery in a unipolar or bipolar fashion in proximity to target tissue. Each high voltage pulse can be a monophasic pulse including a single polarity, or a biphasic pulse including a first component having a first particular polarity and a second component having a second particular polarity opposite the first polarity. In some embodiments, the second component of the biphasic pulse follows immediately after the first component of the biphasic pulse. In some embodiments, the first and second components of the biphasic pulse are temporally separated by a relatively small time interval. The electric field applied by the high voltage pulses physiologically changes the tissue cells to which the energy is applied (e.g., puncturing of the cell membrane to form various pores therein). If a lower field strength is established, the formed pores may close in time and cause the cells to maintain viability (e.g., a process sometimes referred to as reversible electroporation). If the field strength that is established is greater, then permanent, and sometimes larger, pores form in the tissue cells, the pores allowing leakage of cell contents, eventually resulting in cell death (e.g., a process sometimes referred to as irreversible electroporation). Even though high voltage and high current amplitudes are employed with PFA, the number of active pulsed field electrodes may be limited or controlled, which, along with the very short pulse durations of PFA pulses, may prevent the production of excessive Joule heating.

The word "fluid" as used in this disclosure should be understood to include any fluid that can be contained within a bodily cavity or can flow into or out of, or both into and out of a bodily cavity via one or more bodily openings positioned in fluid communication with the bodily cavity. In the case of cardiac applications, fluid such as blood will flow into and out of various intra-cardiac cavities (e.g., a left atrium or a right atrium).

The words "bodily opening" as used in this disclosure should be understood to include a naturally occurring bodily opening or channel or lumen; a bodily opening or channel or lumen formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath) may be present in various embodiments. These elements may provide a passageway through a bodily opening for various devices employed in various embodiments.

The words "bodily cavity" as used in this disclosure should be understood to mean a cavity in a body. The bodily cavity may be a cavity or chamber provided in a bodily organ (e.g., an intra-cardiac cavity of a heart).

The word "tissue" as used in some embodiments in this disclosure should be understood to include any surface-forming tissue that is used to form a surface of a body or a surface within a bodily cavity, a surface of an anatomical feature or a surface of a feature associated with a bodily opening positioned in fluid communication with the bodily cavity. The tissue can include part, or all, of a tissue wall or membrane that defines a surface of the bodily cavity. In this regard, the tissue can form an interior surface of the cavity that surrounds a fluid within the cavity. In the case of cardiac applications, tissue can include tissue used to form an interior surface of an intra-cardiac cavity such as a left atrium or a right atrium. In some embodiments, the word tissue can refer to a tissue having fluidic properties (e.g., blood) and may be referred to as fluidic tissue.

The term "transducer" as used in this disclosure should be interpreted broadly as any device capable of distinguishing between fluid and tissue, sensing temperature, creating heat, ablating tissue, sensing, sampling or measuring electrical activity of a tissue surface (e.g., sensing, sampling or measuring intra-cardiac electrograms, or sensing, sampling or measuring intra-cardiac voltage data), stimulating tissue, or any combination thereof. A transducer can convert input energy of one form into output energy of another form. Without limitation, a transducer can include an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed. In this regard, although transducers, electrodes, or both transducers and electrodes are referenced with respect to various embodiments, it is understood that other transducers or transducer elements may be employed in other embodiments. It is understood that a reference to a particular transducer in various embodiments may also imply a reference to an electrode, as an electrode may be part of the transducer as shown, e.g., with FIG. 4 discussed below.

The term "activation" as used in this disclosure should be interpreted broadly as making active a particular function as related to various transducers disclosed in this disclosure. Particular functions may include, but are not limited to, tissue ablation (e.g., PFA), sensing, sampling or measuring electrophysiological activity (e.g., sensing, sampling or measuring intra-cardiac electrogram information or sensing, sampling or measuring intra-cardiac voltage data), sensing, sampling or measuring temperature and sensing, sampling or measuring electrical characteristics (e.g., tissue impedance or tissue conductivity). For example, in some embodiments, activation of a tissue ablation function of a particular transducer is initiated by causing energy sufficient for tissue ablation from an energy source device system to be delivered to the particular transducer. Also in this example, the activation can last for a duration of time concluding when the ablation function is no longer active, such as when energy sufficient for the tissue ablation is no longer provided to the particular transducer. In some contexts, however, the word "activation" can merely refer to the initiation of the activating of a particular function, as opposed to referring to both the initiation of the activating of the particular function and the subsequent duration in which the particular function is active. In these contexts, the phrase or a phrase similar to "activation initiation" may be used.

In the following description, some embodiments of the present invention may be implemented at least in part by a data processing device system or a controller system configured by a software program. Such a program may equivalently be implemented as multiple programs, and some or all of such software program(s) may be equivalently constructed in hardware.

The term "program" in this disclosure should be interpreted as a set of instructions or modules that can be executed by one or more components in a system, such as a controller system or a data processing device system, in order to cause the system to perform one or more operations. The set of instructions or modules can be stored by any kind of memory device, such as those described subsequently with respect to the memory device system 130 or 330 shown in FIGS. 1 and 3, respectively. In addition, this disclosure sometimes describes that the instructions or modules of a program are configured to cause the performance of a function. The phrase "configured to" in this context is intended to include at least (a) instructions or modules that are presently in a form executable by one or more data processing devices to cause performance of the function (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the function (e.g., in the case where the instructions or modules are encrypted in a non-executable manner, but through performance of a decryption process, would be translated into a form ready for execution). The word "module" can be defined as a set of instructions. In some instances, this disclosure describes that the instructions or modules of a program perform a function. Such descriptions should be deemed to be equivalent to describing that the instructions or modules are configured to cause the performance of the function.

Each of the phrases "derived from" or "derivation of" or "derivation thereof" or the like may be used herein to mean to come from at least some part of a source, be created from at least some part of a source, or be developed as a result of a process in which at least some part of a source forms an input. For example, a data set derived from some particular portion of data may include at least some part of the particular portion of data, or may be created from at least part of the particular portion of data, or may be developed in response to a data manipulation process in which at least part of the particular portion of data forms an input. In some embodiments, a data set may be derived from a subset of the particular portion of data. In some embodiments, the particular portion of data is analyzed to identify a particular subset of the particular portion of data, and a data set is derived from the subset. In various ones of these embodiments, the subset may include some, but not all, of the particular portion of data. In some embodiments, changes in least one part of a particular portion of data may result in changes in a data set derived at least in part from the particular portion of data.

In this regard, each of the phrases "derived from" or "derivation of" or "derivation thereof" or the like may be used herein merely to emphasize the possibility that such data or information may be modified or subject to one or more operations. For example, if a device generates first data for display, the process of converting the generated first data into a format capable of being displayed may alter the first data. This altered form of the first data may be considered a derivative or derivation of the first data. For instance, the first data may be a one-dimensional array of numbers, but the display of the first data may be a color-coded bar chart representing the numbers in the array. For another example, if the above-mentioned first data is transmitted over a network, the process of converting the first data into a format acceptable for network transmission or understanding by a receiving device may alter the first data. As before, this altered form of the first data may be considered a derivative or derivation of the first data. For yet another example, generated first data may undergo a mathematical operation, a scaling, or a combining with other data to generate other data that may be considered derived from the first data. In this regard, it can be seen that data is commonly changing in form or being combined with other data throughout its movement through one or more data processing device systems, and any reference to information or data herein is intended to include these and like changes, regardless of whether or not the phrase "derived from" or "derivation of" or "derivation thereof" or the like is used in reference to the information or data. As indicated above, usage of the phrase "derived from" or "derivation of" or "derivation thereof" or the like merely emphasizes the possibility of such changes. Accordingly, the addition of or deletion of the phrase "derived from" or "derivation of" or "derivation thereof" or the like should have no impact on the interpretation of the respective data or information. For example, the above-discussed color-coded bar chart may be considered a derivative of the respective first data or may be considered the respective first data itself.

In some embodiments, the term "adjacent", the term "proximate", and the like refer at least to a sufficient closeness between the objects or events defined as adjacent, proximate, or the like, to allow the objects or events to interact in a designated way. For example, in the case of physical objects, if object A performs an action on an adjacent or proximate object B, objects A and B would have at least a sufficient closeness to allow object A to perform the action on object B. In this regard, some actions may require contact between the associated objects, such that if object A performs such an action on an adjacent or proximate object B, objects A and B would be in contact, for example, in some instances or embodiments where object A needs to be in contact with object B to successfully perform the action. In some embodiments, the term "adjacent", the term "proximate", and the like additionally or alternatively refer to objects or events that do not have another substantially similar object or event between them. For example, object or event A and object or event B could be considered adjacent or proximate (e.g., physically or temporally) if they are immediately next to each other (with no other object or event between them) or are not immediately next to each other but no other object or event that is substantially similar to object or event A, object or event B, or both objects or events A and B, depending on the embodiment, is between them. In some embodiments, the term "adjacent", the term "proximate", and the like additionally or alternatively refer to at least a sufficient closeness between the objects or events defined as adjacent, proximate, and the like, the sufficient closeness being within a range that does not place any one or more of the objects or events into a different or dissimilar region or time period, or does not change an intended function of any one or more of the objects or events or of an encompassing object or event that includes a set of the objects or events. Different embodiments of the present invention adopt different ones or combinations of the above definitions. Of course, however, the term "adjacent", the term "proximate", and the like are not limited to any of the above example definitions, according to some embodiments. In addition, the term "adjacent" and the term "proximate" do not have the same definition, according to some embodiments. Further still, example methods are described herein with respect to FIGS. 10-12. Such figures include blocks associated with actions, computer-executable instructions, or both, according to various embodiments. It should be noted that the respective instructions associated with any such blocks herein need not be separate instructions and may be combined with other instructions to form a combined instruction set. The same set of instructions may be associated with more than one block. In this regard, the block arrangement shown in each of the method figures herein is not limited to an actual structure of any program or set of instructions or required ordering of method tasks, and such method figures, according to some embodiments, merely illustrate the tasks that instructions are configured to perform, for example upon execution by a data processing device system in conjunction with interactions with one or more other devices or device systems.

FIG. 1 schematically illustrates a portion of a pulsed field ablation ("PFA") system or controller system thereof 100 that may be employed to at least select, control, activate, or monitor a function or activation of a number of PFA transducers or electrodes, according to some embodiments. The system 100 includes a data processing device system 110, an input-output device system 120, and a processor-accessible memory device system 130. The processor-accessible memory device system 130 and the input-output device system 120 are communicatively connected to the data processing device system 110. According to some embodiments, various components such as data processing device system 110, input-output device system 120, and processor-accessible memory device system 130 form at least part of a controller system (e.g., controller system 324 shown in FIG. 3).

Figure 10:
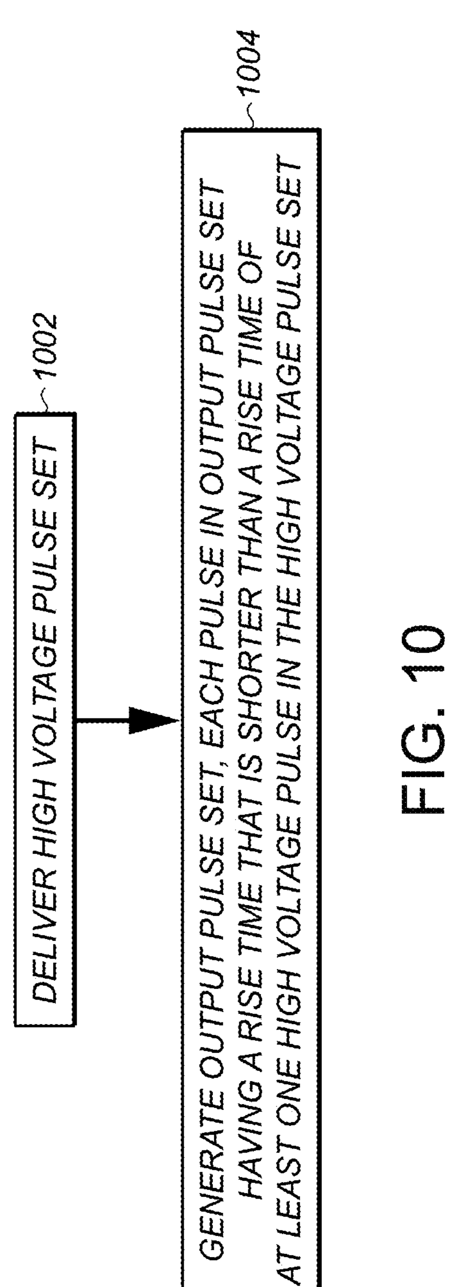
FIGS. 10, 11, and 12 each illustrate methods of performing pulsed field ablation, according to some embodiments.
Figure 11:
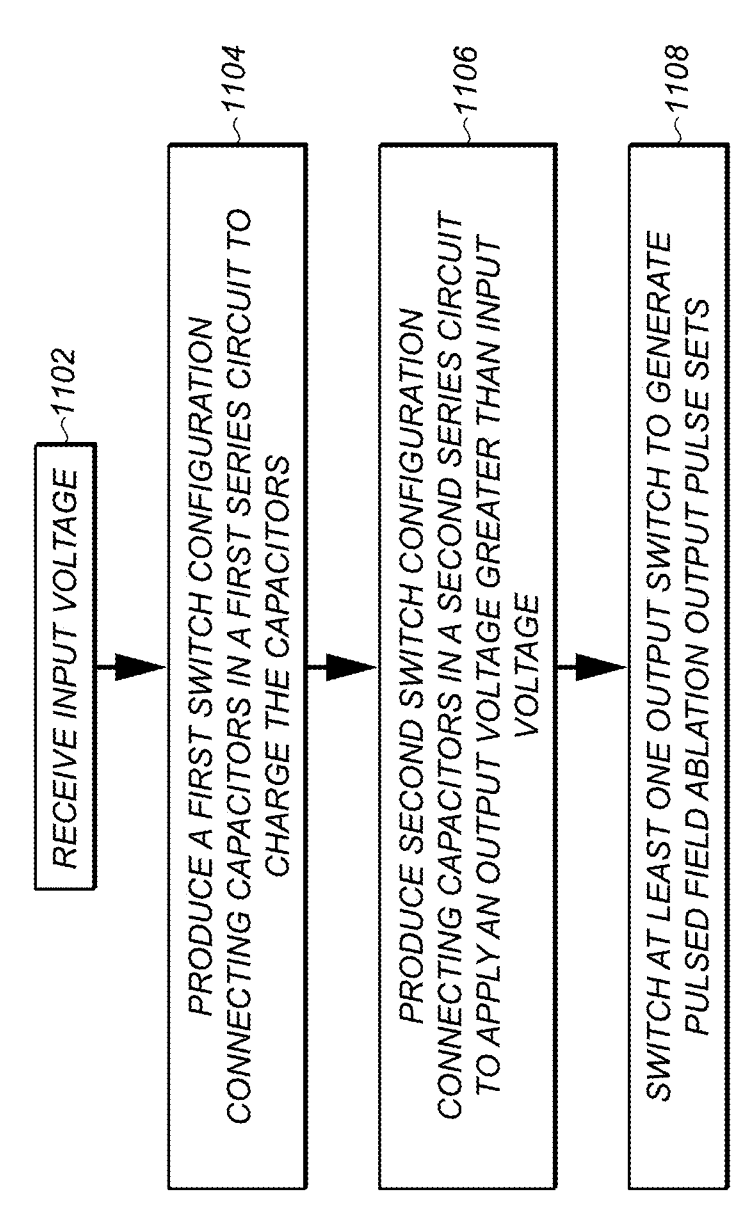
Figure 12:
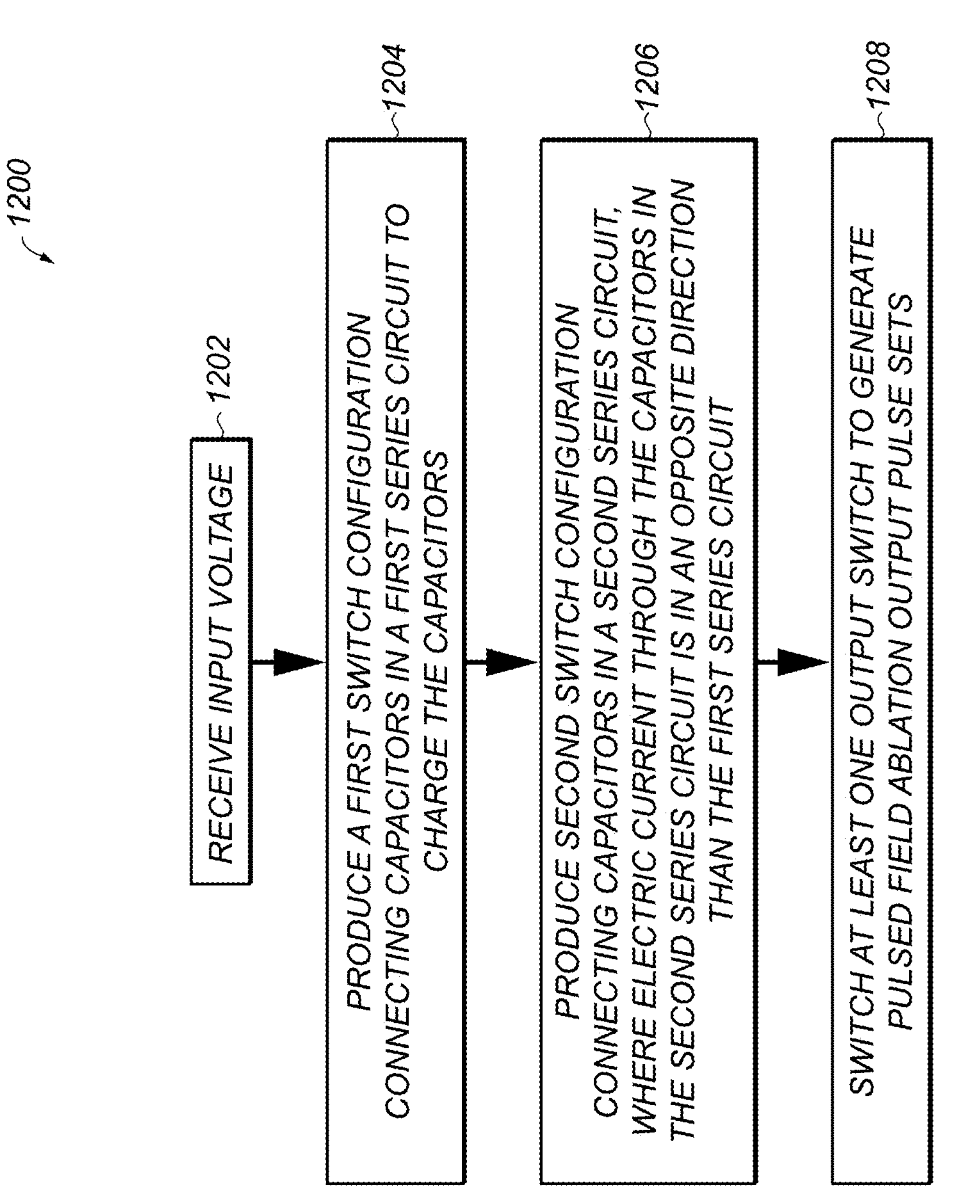

The data processing device system 110 includes one or more data processing devices that implement or execute, in conjunction with other devices, such as those in the system 100, various methods and functions described herein, including those described with respect to methods exemplified in FIGS. 10-12. Each of the phrases "data processing device", "data processor", "processor", and "computer" is intended to include any data or information processing device, such as a central processing unit (CPU), a control circuit, a desktop computer, a laptop computer, a mainframe computer, a tablet computer, a personal digital assistant, a cellular phone, and any other device for processing data, managing data, or handling data, whether implemented with electrical, magnetic, optical, or biological components, or otherwise.

The memory device system 130 includes one or more processor-accessible memory devices configured to store one or more program and information, including the program(s) and information needed to execute the methods or functions described herein, including those described with respect to method FIGS. 10-12. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single data processing device.

Each of the phrases "processor-accessible memory" and "processor-accessible memory device" and the like is intended to include any processor-accessible data storage device or medium, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include or be a processor-accessible (or computer-readable) data storage medium. In some embodiments, each of the phrases "processor-accessible memory" and "processor-accessible memory device" is intended to include or be a non-transitory processor-accessible (or computer-readable) data storage medium. In some embodiments, the processor-accessible memory device system 130 may be considered to include or be a non-transitory processor-accessible (or computer-readable) data storage medium system. And, in some embodiments, the memory device system 130 may be considered to include or be a non-transitory processor-accessible (or computer-readable) storage medium system or data storage medium system including or consisting of one or more non-transitory processor-accessible (or computer-readable) storage or data storage mediums.

The phrase "communicatively connected" is intended to include any type of connection, whether wired or wireless, between devices, data processors, or programs between which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 can be implemented by a single application-specific integrated circuit (ASIC) in some embodiments.

The input-output device system 120 may include a mouse, a keyboard, a touch screen, another computer, or any device or combination of devices from which a desired selection, desired information, instructions, or any other data is input to the data processing device system 110. The input-output device system 120 may include a user-activatable control system that is responsive to a user action. The user-activatable control system may include at least one control element that may be activated or deactivated on the basis of a particular user action. The input-output device system 120 may include any suitable interface for receiving information, instructions or any data from other devices and systems described in various ones of the embodiments. In this regard, the input-output device system 120 may include various ones of other systems described in various embodiments. For example, the input-output device system 120 may include at least a portion of a transducer-based device system. The phrase "transducer-based device system" is intended to include one or more physical systems that include various transducers. The phrase "transducer-based device" is intended to include one or more physical devices that include various transducers. A PFA device system that includes one or more transducers may be considered a transducer-based device, according to some embodiments.

The input-output device system 120 also may include an image generating device system, a display device system, a speaker device system, a computer, a processor-accessible memory device system, a network-interface card or network-interface circuitry, or any device or combination of devices to which information, instructions, or any other data is output by the data processing device system 110. In this regard, the input-output device system 120 may include various other devices or systems described in various embodiments. The input-output device system 120 may include any suitable interface for outputting information, instructions, or data to other devices and systems described in various ones of the embodiments. If the input-output device system 120 includes a processor-accessible memory device, such memory device may, or may not, form part or all of the memory device system 130. The input-output device system 120 may include any suitable interface for outputting information, instructions, or data to other devices and systems described in various ones of the embodiments. In this regard, the input-output device system 120 may include various other devices or systems described in various embodiments.

Figure 2:
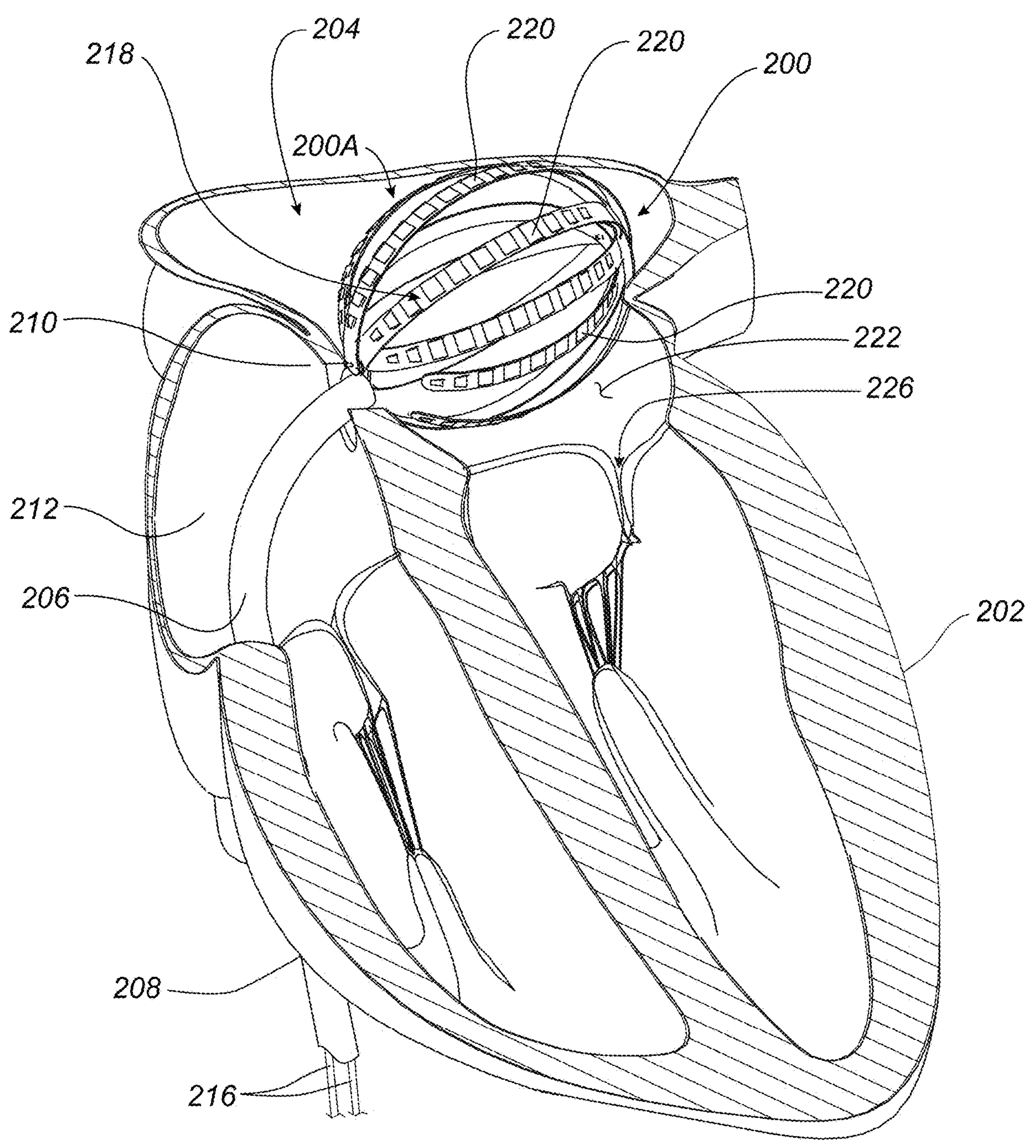
FIG. 2 includes a cutaway diagram of a heart showing a structure of a pulsed field ablation device percutaneously placed in a left atrium of a heart, according to various example embodiments.

According to some embodiments of the present invention, the system 100 includes some or all of the system 200 shown in FIG. 2, or vice versa. In some embodiments, the system 100 includes some or all of the system 300 in FIGS. 3, or vice versa. In this regard, the system 200, the system 300, or each of the system 200 and the system 300 may be a particular implementation of the system 100, according to some embodiments. Each of at least part of one or more of the system 400A in FIG. 4 and the circuits in FIGS. 5A-5E, 7, 8, and 9 may be part of the system 100, the system 200, or the system 300, according to various embodiments. Various embodiments of transducer-based devices are described herein. Some of the described devices are PFA devices that are percutaneously or intravascularly deployed. Some of the described devices are movable between a delivery or unexpanded configuration (e.g., FIG. 3A discussed below) in which a portion of the device is sized for passage through a bodily opening leading to a bodily cavity, and an expanded or deployed configuration (e.g., FIG. 3B discussed below) in which the portion of the device has a size too large for passage through the bodily opening leading to the bodily cavity. An example of an expanded or deployed configuration is when the portion of the transducer-based device is in its intended-deployed-operational state inside the bodily cavity. Another example of the expanded or deployed configuration is when the portion of the transducer-based device is being changed from the delivery configuration to the intended-deployed-operational state to a point where the portion of the device now has a size too large for passage through the bodily opening leading to the bodily cavity.

In some example embodiments, the device includes transducers that sense characteristics (e.g., convective cooling, permittivity, force) that distinguish between fluid, such as a fluidic tissue (e.g., blood), and tissue forming an interior surface of the bodily cavity. Such sensed characteristics can allow a medical system to map the cavity, for example using positions of openings or ports into and out of the cavity to determine a position or orientation (e.g., pose), or both of the portion of the device in the bodily cavity. In some example embodiments, the described systems employ a navigation system or electro-anatomical mapping system including electromagnetic-based systems and electropotential-based systems to determine a positioning of a portion of a device in a bodily cavity. In some example embodiments, the described devices are capable of ablating tissue in a desired pattern within the bodily cavity using PFA techniques.

In some example embodiments, the devices are capable of sensing various cardiac functions (e.g., electrophysiological activity including intra-cardiac voltages). In some example embodiments, the devices are capable of providing stimulation (e.g., electrical stimulation) to tissue within the bodily cavity. Electrical stimulation may include pacing.

FIG. 2 is a representation of a PFA system 200 including a PFA device 200A useful in treating a bodily organ, for example, a heart 202, according to one example embodiment.

PFA device 200A can be percutaneously or intravascularly inserted into a portion of the heart 202, such as an intra-cardiac cavity like left atrium 204. In this example, the PFA device 200A is part of a catheter 206 inserted via the inferior vena cava 208 and penetrating through a bodily opening in transatrial septum 210 from right atrium 212. In other embodiments, other paths may be taken.

Catheter 206 includes an elongated flexible rod or shaft member appropriately sized to be delivered percutaneously or intravascularly. Various portions of catheter 206 may be steerable. Catheter 206 may include one or more lumens (not shown). The lumen(s) may carry one or more communications or power paths, or both. For example, the lumens(s) may carry one or more electrical conductors 216 (two shown in some embodiments). Electrical conductors 216 provide electrical connections to PFA system 200 that are accessible (e.g., by a controller system or data processing device system) externally from a patient in which the PFA device 200A is inserted.

PFA device 200A includes a frame or structure 218 which assumes an unexpanded configuration for delivery to left atrium 204. Structure 218 is expanded (e.g., shown in a deployed or expanded configuration in FIG. 2) upon delivery to left atrium 204 to position a plurality of transducers 220 (three called out in FIG. 2) proximate the interior surface formed by tissue 222 of left atrium 204. In some embodiments, at least some of the transducers 220 are used to sense a physical characteristic of a fluid (e.g., blood) or tissue 222, or both, that may be used to determine a position or orientation (e.g., pose), or both, of a portion of PFA system 200 within, or with respect to left atrium 204. For example, transducers 220 may be used to determine a location of pulmonary vein ostia (not shown) or a mitral valve 226, or both. In some embodiments, at least some of the transducers 220 may be used to selectively ablate portions of the tissue 222. In some embodiments, at least some of the transducers 220 may be used to selectively ablate portions of the tissue 222 using PFA. In some embodiments, some of the transducers 220 may be used to ablate a pattern around the bodily openings, ports or pulmonary vein ostia, for instance to reduce or eliminate the occurrence of atrial fibrillation. In some embodiments, at least some of the transducers 220 are used to ablate cardiac tissue, such as by PFA. In some embodiments, at least some of the transducers 220 are used to sense or sample intra-cardiac voltage data or sense or sample intra-cardiac electrogram data. In some embodiments, at least some of the transducers 220 are used to sense or sample intra-cardiac voltage data or sense or sample intra-cardiac electrogram data while at least some of the transducers 220 are concurrently ablating cardiac tissue. In some embodiments, at least one of the sensing or sampling transducers 220 is provided by at least one of the ablating transducers 220. In some embodiments, at least a first one of the transducers 220 senses or samples intra-cardiac voltage data or intra-cardiac electrogram data at a location at least proximate to a tissue location ablated by at least a second one of the transducers 220. In some embodiments, the first one of the transducers 220 is other than the second one of the transducers 220. In various embodiments, each of at least some of the transducers 220 includes an electrode. In various embodiments, each of at least some of the transducers 220 includes an electrode configured to deliver PFA pulses to tissue.

Figure 3A:
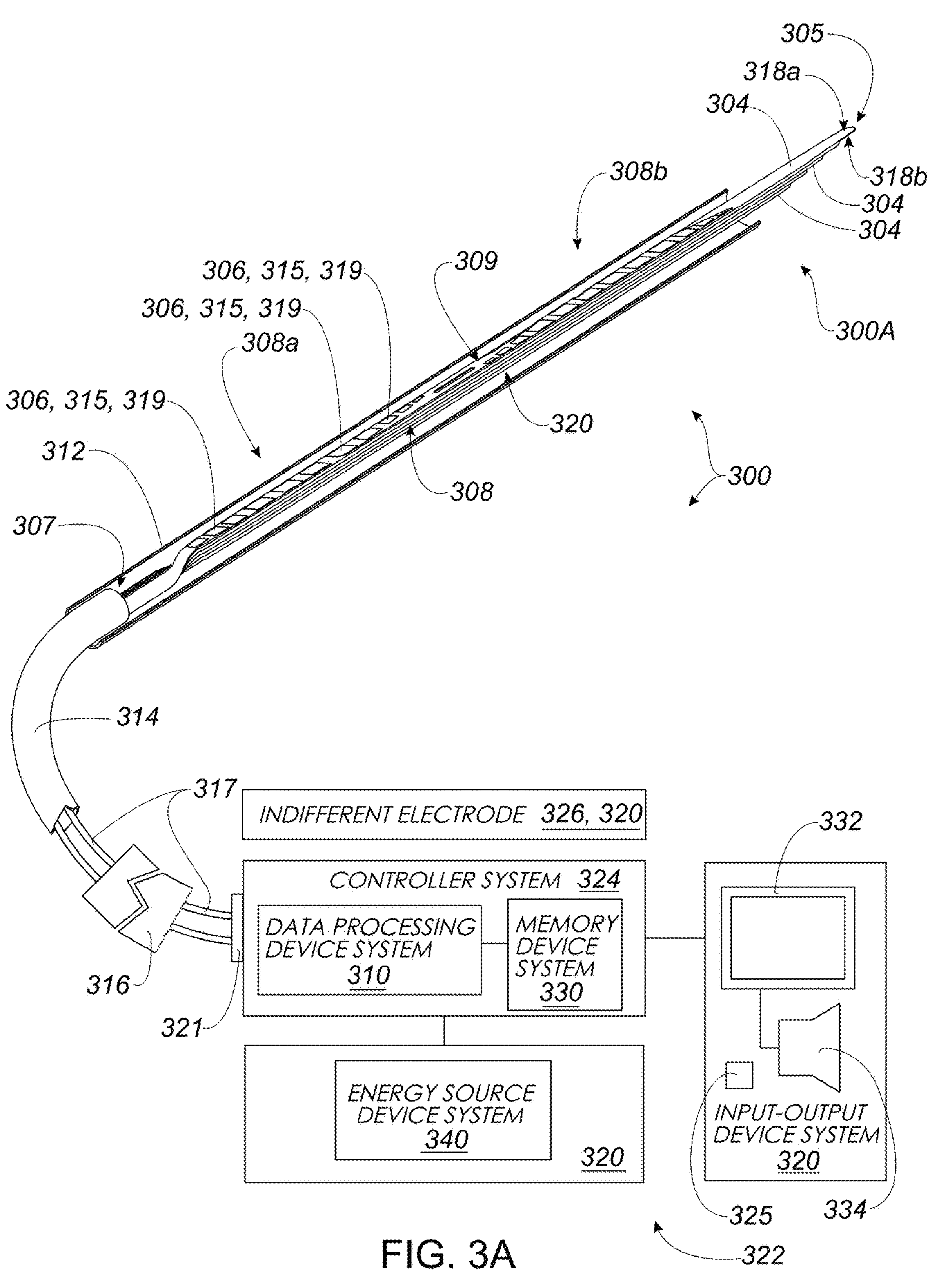
FIG. 3A includes a partially schematic representation of a pulsed field ablation system, according to various example embodiments, the pulsed field ablation system representing at least a particular implementation of the pulsed field ablation system of FIG. 1, and the pulsed field ablation system including a structure of a pulsed field ablation device shown in a delivery or unexpanded configuration, according to some embodiments.
Figure 3B:
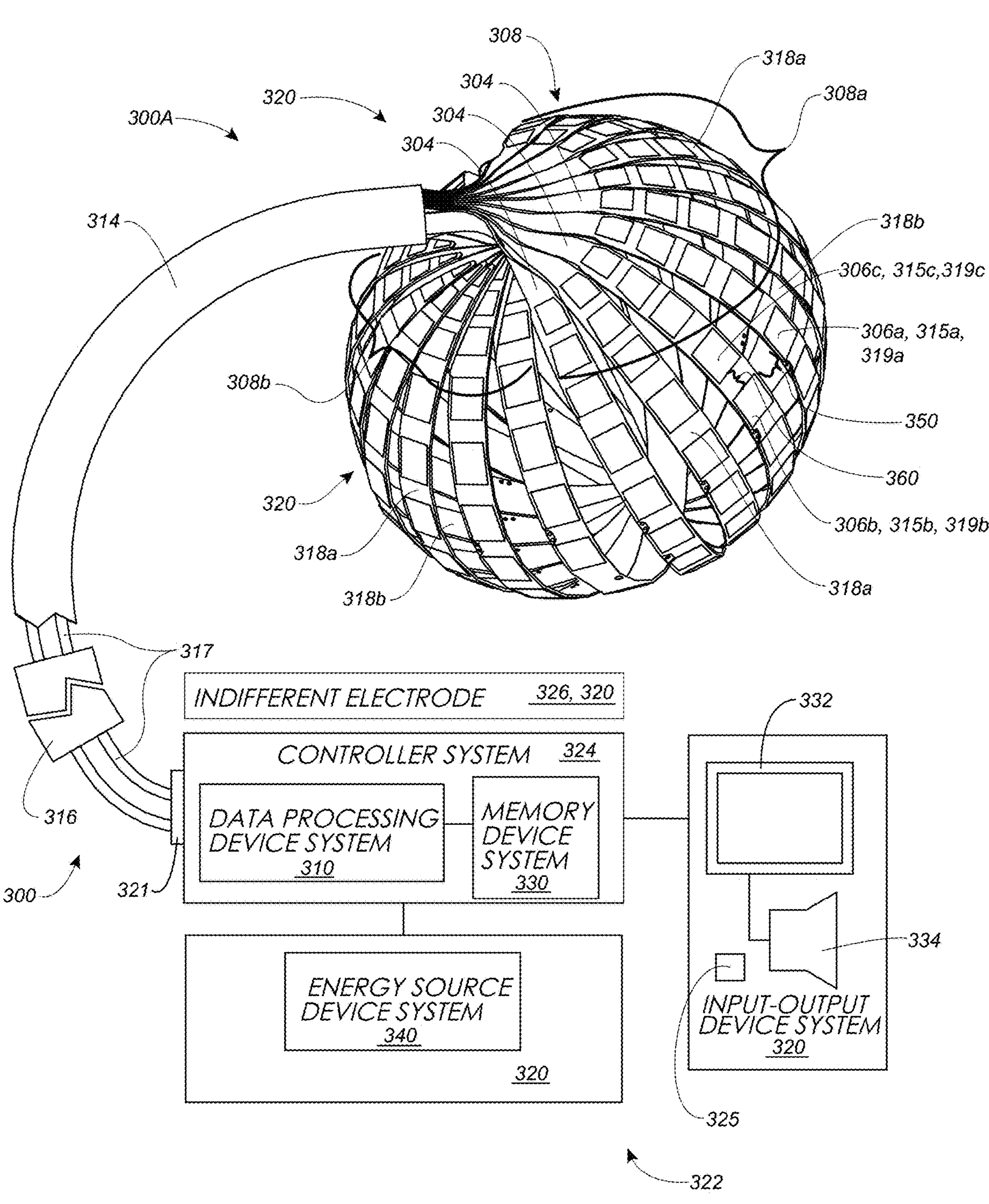
FIG. 3B includes a representation of the structure of the pulsed field ablation device of FIG. 3A in a deployed or expanded configuration, according to some embodiments.

FIGS. 3A and 3B (collectively, FIG. 3) include a PFA system 300 (e.g., a portion thereof shown schematically) that includes a PFA device 300A, according to one illustrated embodiment. Each of FIGS. 3A and 3B may represent one or more implementations of the medical device system 100 of FIG. 1, according to some embodiments. In this regard, the PFA system 300 in each of FIGS. 3A and 3B may be configured to deliver energy to each of one or more elements, such as a transducer or electrode. The PFA device 300A may include several hundreds of electrodes 315, but need not include that many. FIG. 3A illustrates the PFA device 300A in the delivery or unexpanded configuration, according to various example embodiments, and FIG. 3B illustrates the PFA device 300A in the deployed or expanded configuration, according to some embodiments.

In this regard, the PFA device 300A includes a plurality of elongate members 304 (three called out in each of FIGS. 3A and 3B) and a plurality of transducers 306 (three called out in FIG. 3A and three called out in FIG. 3B as 306*a*, 306*b* and 306*c*). In some embodiments, the transducers 306 have the configuration of the transducers 220 in FIG. 2. In some embodiments, the transducers 306 are formed as part of, or are located on, the elongate members 304. In some embodiments, the elongate members 304 are arranged as a frame or structure 308 that is selectively movable between an unexpanded or delivery configuration (e.g., as shown in FIG. 3A) and an expanded or deployed configuration (e.g., as shown in FIG. 3B) that may be used to position elongate members 304 or various one of the transducers 306 against a tissue surface within the bodily cavity or position the elongate members 304 in the vicinity of, or in contact with, the tissue surface.

In some embodiments, the structure 308 has a size in the unexpanded or delivery configuration suitable for percutaneous delivery through a bodily opening (e.g., via catheter sheath 312, not shown in FIG. 3B) to the bodily cavity. In some embodiments, structure 308 has a size in the expanded or deployed configuration too large for percutaneous delivery through a bodily opening (e.g., via catheter sheath 312) to the bodily cavity. The elongate members 304 may form part of a flexible circuit structure (e.g., also known as a flexible printed circuit board (PCB)). The elongate members 304 may include a plurality of different material layers, and each of the elongate members 304 may include a plurality of different material layers. The structure 308 may include a shape memory material, for instance Nitinol. The structure 308 may include a metallic material, for instance stainless steel, or non-metallic material, for instance polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (e.g., pose) or both of structure 308 in the bodily cavity, or the requirements for successful PFA of a desired pattern.

The plurality of transducers 306 are positionable within a bodily cavity, for example, by positioning of the structure 308. For instance, in some embodiments, the transducers 306 are able to be positioned in a bodily cavity by movement into, within, or into and within the bodily cavity, with or without a change in a configuration of the plurality of transducers 306 (e.g., a change in a configuration of the structure 308 causes a change in a configuration of the transducers 306 in some embodiments). In some embodiments, the plurality of transducers 306 is arrangeable to form a two- or three-dimensional distribution, grid, or array capable of mapping, ablating, or stimulating an inside surface of a bodily cavity or lumen without requiring mechanical scanning. As shown, for example, in FIG. 3A, the plurality of transducers 306 is arranged in a distribution receivable in a bodily cavity (not shown in FIG. 3A). As shown, for example, in FIG. 3A, the plurality of transducers 306 is arranged in a distribution suitable for delivery to a bodily cavity.

Figure 4:
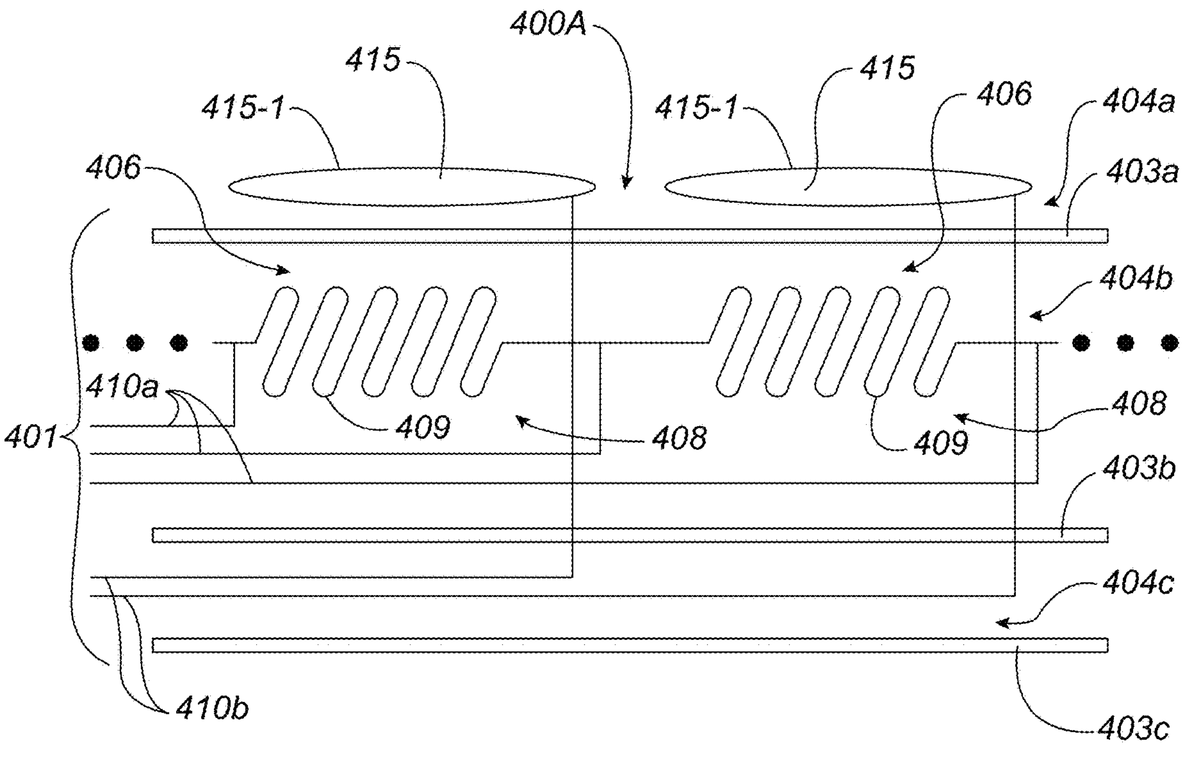
FIG. 4 includes a representation of a pulsed field ablation device that includes a flexible circuit structure, according to some embodiments.

FIG. 4 is a schematic side elevation view of at least a portion of a PFA device 400A that includes a flexible circuit structure 401 that is employed to provide a plurality of transducers 406 (two called out) according to an example embodiment. Such transducers may correspond to transducers 220 or 306, according to various embodiments. In some embodiments, the flexible circuit structure 401 may form part of a structure (e.g., structure 308) that is selectively movable between a delivery configuration sized for percutaneous delivery and expanded or deployed configurations sized too large for percutaneous delivery. In some embodiments, the flexible circuit structure 401 may be located on, or form at least part of, a structural component (e.g., elongate member 304) of a transducer-based device system.

The flexible circuit structure 401 can be formed by various techniques including flexible printed circuit techniques. In some embodiments, the flexible circuit structure 401 includes various layers including flexible layers 403*a*, 403*b* and 403*c* (e.g., collectively flexible layers 403). In some embodiments, each of flexible layers 403 includes an electrical insulator material (e.g., polyimide). One or more of the flexible layers 403 can include a different material than another of the flexible layers 403. In some embodiments, the flexible circuit structure 401 includes various electrically conductive layers 404*a*, 404*b* and 404*c* (collectively electrically conductive layers 404) that are interleaved with the flexible layers 403. In some embodiments, each of the electrically conductive layers 404 is patterned to form various electrically conductive elements. For example, electrically conductive layer 404*a* is patterned to form a respective electrode 415 of each of the transducers 406. In some embodiments, electrodes 415 correspond to electrodes 315. Electrodes 415 have respective electrode edges 415-1 that form a periphery of an electrically conductive surface associated with the respective electrode 415. It is noted that other electrodes employed in other embodiments may have electrode edges arranged to form different electrodes shapes.

Electrically conductive layer 404*b* is patterned, in some embodiments, to form respective temperature sensors 408 for each of the transducers 406 as well as various leads 410*a* arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404*c* is patterned to provide portions of various leads 410*b* arranged to provide an electrical communication path to electrodes 415. In some embodiments, leads 410*b* are arranged to pass though vias (not shown) in flexible layers 403*a* and 403*b* to connect with electrodes 415. Although FIG. 4 shows flexible layer 403*c* as being a bottom-most layer, some embodiments may include one or more additional layers underneath flexible layer 403*c*, such as one or more structural layers, such as a steel or composite layer. These one or more structural layers, in some embodiments, are part of the flexible circuit structure 401 and can be part of, e.g., elongate member 304. In some embodiments, the one or more structural layers may include at least one electrically conductive surface (e.g., a metallic surface) exposed to blood flow. In addition, although FIG. 4 shows only three flexible layers 403*a*-403*c* and only three electrically conductive layers 404*a*-404*c*, it should be noted that other numbers of flexible layers, other numbers of electrically conductive layers, or both, can be included.

In some embodiments, electrodes 415 are employed to selectively deliver PFA high voltage output pulses to various tissue structures within a bodily cavity (not shown in FIG. 4) (e.g., an intra-cardiac cavity or chamber). The PFA high voltage pulses delivered to the tissue structures may be sufficient for ablating portions of the tissue structures. The PFA high voltage pulses delivered to the tissue may be delivered to cause monopolar pulsed field tissue ablation, bipolar pulsed field tissue ablation, or blended monopolar-bipolar pulsed field tissue ablation by way of non-limiting example.

The energy that is delivered by each high voltage pulse may be dependent upon factors including the electrode location, size, shape, relationship with respect to another electrode (e.g., the distance between adjacent electrodes that deliver the PFA energy), the presence, or lack thereof of various material between the electrodes, the degree of electrode-to-tissue contact, and other factors. In some cases, a maximum ablation depth resulting from the delivery of high voltage pulses by a relatively smaller electrode is typically shallower than that of a relatively larger electrode.

In some embodiments, each electrode 415 is employed to sense or sample an electrical potential in the tissue proximate the electrode 415 at a same or different time than delivering high voltage output pulses for pulsed field tissue ablation. In some embodiments, each electrode 415 is employed to sense or sample intra-cardiac voltage data in the tissue proximate the electrode 415. In some embodiments, each electrode 415 is employed to sense or sample data in the tissue proximate the electrode 415 from which an electrogram (e.g., an intra-cardiac electrogram) may be derived. In some embodiments, each resistive member 409 is positioned adjacent a respective one of the electrodes 415. In some embodiments, each of the resistive members 409 is positioned in a stacked or layered array with a respective one of the electrodes 415 to form a respective one of the transducers 406. In some embodiments, the resistive members 409 are connected in series to allow electrical current to pass through all of the resistive members 409. In some embodiments, leads 410*a* are arranged to allow for a sampling of electrical voltage in between each resistive member 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow).

Referring again to FIGS. 3A and 3B, according to some embodiments, PFA device 300A communicates with, receives power from, or is controlled by a transducer-activation system 322, which may include a controller system 324 and an energy source device system 340. In some embodiments, the controller system 324 includes a data processing device system 310 and a memory device system 330 that stores data and instructions that are executable by the data processing device system 310 to process information received from other components of the PFA system 300 of FIGS. 3A and 3B or to control operation of components of the PFA system 300 of FIGS. 3A and 3B, for example, by activating various selected transducers 306 to perform PFA of tissue, sense tissue characteristics, etc. In this regard, the data processing device system 310 may correspond to at least part of the data processing device system 110 in FIG. 1, according to some embodiments, and the memory device system 330 may correspond to at least part of the memory device system 130 in FIG. 1, according to some embodiments. The energy source device system 340, in some embodiments, is part of an input-output device system 320, which may correspond to at least part of the input-output device system 120 in FIG. 1. The controller system 324 may be implemented by one or more controllers.

In some embodiments, the PFA device 300A is considered to be part of the input-output device system 320. The input-output device system 320 may also include a display device system 332, a speaker device system 334, or any other device such as those described above with respect to the input-output device system 120. Input-output device system 320 may include a sensing device system 325 configured to detect various characteristics including, but not limited to, at least one of tissue characteristics (e.g., electrical characteristics such as tissue impedance, tissue conductivity, tissue type, tissue thickness) and thermal characteristics such as temperature. In this regard, the sensing device system 325 may include one, some, or all of the transducers 306 (or 406 of FIG. 4), including the components of such transducers shown in FIG. 4, such as the electrodes 415 and temperature sensors 408.

In some embodiments, elongate members 304 may form a portion or an extension of control leads 317 that reside, at least in part, in an elongated cable 316 and, at least in part, in a flexible catheter body 314. The control leads terminate at a connector 321 or other interface with the transducer-activation system 322 and provide communication pathways between at least the transducers 306 and the controller 324. The control leads 317 may correspond to electrical conductors 216 in some embodiments.

Figure 5A:
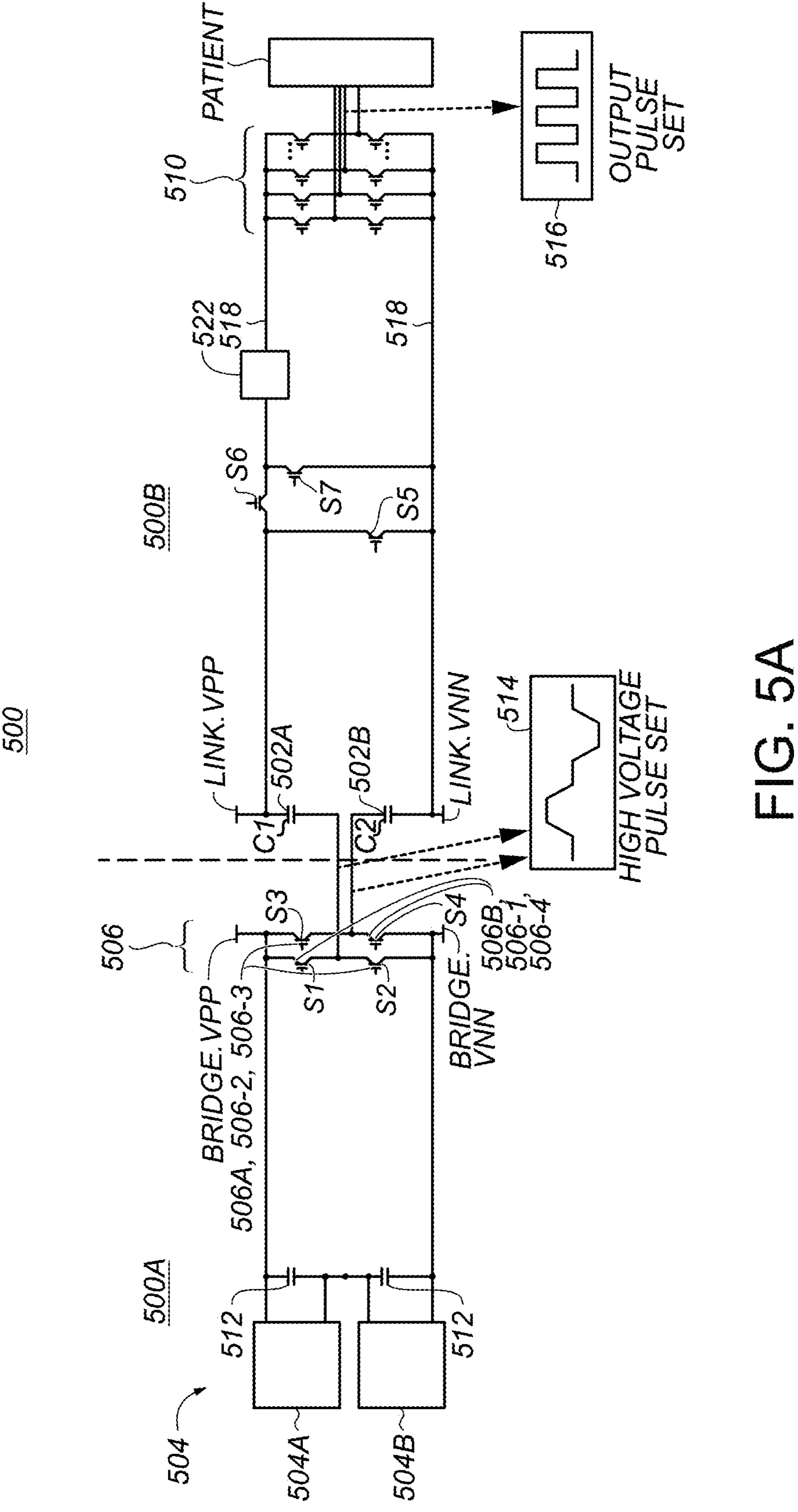
FIG. 5A includes a schematic representation of a circuit employed by a pulsed field ablation system, which may be the same as, or similar to, at least part of the pulsed field ablation system or controller thereof illustrated in FIG. 1, FIG. 2, or FIGS. 3A and 3B, according to some embodiments, where the circuit may include a high voltage pulse generation circuit and an output pulse generation circuit, according to some embodiments.

According to some embodiments, the energy source device system 340 includes a high voltage supply (e.g., 504, FIG. 5A). In this regard, although FIGS. 3A and 3B show a communicative connection between the energy source device system 340 and the controller system 324 (and its data processing device system 310), the energy source device system 340 may also be connected to the transducers 306 via a communicative connection that is independent of the communicative connection with the controller system 324 (and its data processing device system 310). For example, the energy source device system 340 may receive control signals via the communicative connection with the controller system 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through catheter body 314, elongated cable 316 or catheter sheath 312) that does not pass through the controller system 324. In this regard, the energy source device system 340 may provide results of its delivering energy to, receiving energy from, or both delivering energy to and receiving energy from one or more of the transducers 306 to the controller system 324 (and its data processing device system 310) via the communicative connection between the energy source device system 340 and the controller system 324. In some embodiments, some or all of the energy source device system 340 may be considered part of the controller system 324.

In any event, the number of energy source devices (e.g., high voltage supplies) in the energy source device system 340 may be fewer than the number of transducers in some embodiments. In some embodiments, the energy source device system 340 may, for example, be connected to various selected transducers 306 to selectively provide energy in the form of electrical current or power (e.g., RF energy), light, or low temperature fluid to the various selected transducers 306 to cause ablation of tissue. The energy source device system 340 may, for example, selectively provide energy in the form of electrical current to various selected transducers 306 and measure a temperature characteristic, an electrical characteristic, or both at a respective location at least proximate each of the various transducers 306. The energy source device system 340 may include various electrical current sources or electrical power sources as energy source devices. In some embodiments, an indifferent electrode 326 is provided to receive at least a portion of the energy transmitted by at least some of the transducers 306. Consequently, although not shown in various ones of FIGS. 3, the indifferent electrode 326 may be communicatively connected to the energy source device system 340 via one or more communication lines in some embodiments. In addition, although shown separately in various ones of FIGS. 3, indifferent electrode 326 may be considered part of the energy source device system 340 in some embodiments. In various embodiments, indifferent electrode 326 is positioned on an external surface (e.g., a skin-based surface) of a body that includes the bodily cavity into which at least transducers 306 are to be delivered.

It is understood that input-output device system 320 may include other systems. In some embodiments, input-output device system 320 may optionally include energy source device system 340, PFA device 300A, or both energy source device system 340 and PFA device 300A, by way of non-limiting example. Input-output device system 320 may include the memory device system 330 in some embodiments.

Structure 308 may be delivered and retrieved via a catheter member, for example, a catheter sheath 312. In some embodiments, the structure 308 provides expansion and contraction capabilities for a portion of a medical device (e.g., an arrangement, distribution or array of transducers 306). The transducers 306 may form part of, be positioned or located on, mounted or otherwise carried on the structure 308 and the structure may be configurable to be appropriately sized to slide within catheter sheath 312 in order to be deployed percutaneously or intravascularly. FIG. 3A shows one embodiment of such a structure, where the elongate members 304, in some embodiments, are stacked in the delivery or unexpanded configuration to facilitate fitting within the flexible catheter sheath 312. In some embodiments, each of the elongate members 304 includes a respective distal end 305 (only one called out in FIG. 3A), a respective proximal end 307 (only one called out in FIG. 3A) and an intermediate portion 309 (only one called out in FIG. 3A) positioned between the proximal end 307 and the distal end 305. Correspondingly, in some embodiments, structure 308 includes a proximal portion 308*a* and a distal portion 308*b*. In some embodiments, the proximal and the distal portions 308*a*, 308*b* include respective portions of elongate members 304. The respective intermediate portion 309 of each elongate member 304 may include a first or front surface 318*a* that is positionable to face an interior tissue surface within a bodily cavity and a second or back surface 318*b* opposite across a thickness of the intermediate portion 309 from the front surface 318*a*. In some embodiments, each elongate member 304 includes a twisted portion at a location proximate proximal end 307. The transducers 306 may be arranged in various distributions or arrangements in various embodiments. In some embodiments, various ones of the transducers 306 are spaced apart from one another in a spaced apart distribution as shown, for example in at least FIGS. 3A and 3B. In some embodiments, various regions of space are located between various pairs of the transducers 306. For example, in FIG. 3B the transducer-based device system 300 includes at least a first transducer 306*a*, a second transducer 306*b* and a third transducer 306*c* (all collectively referred to as transducers 306). In some embodiments, each of the first, the second, and the third transducers 306*a*, 306*b* and 306*c* are adjacent transducers in the spaced apart distribution. In some embodiments, the first and the second transducers 306*a*, 306*b* are located on different elongate members 304 while the second and the third transducers 306*b*, 306*c* are located on a same elongate member 304. In some embodiments, a first region of space 350 is between the first and the second transducers 306*a*, 306*b*. In some embodiments, the first region of space 350 is not associated with any physical portion of structure 308. In some embodiments, a second region of space 360 associated with a physical portion of device system 300 (e.g., a portion of an elongate member 304) is between the second and the third transducers 306*b*, 306*c*. In some embodiments, each of the first and the second regions of space 350, 360 do not include a transducer or electrode thereof of transducer-based device system 300. In some embodiments, each of the first and the second regions of space 350, 360 do not include any transducer or electrode.

It is noted that other embodiments need not employ a group of elongate members 304 as employed in the illustrated figures. For example, other embodiments may employ a structure including one or more surfaces, at least a portion of the one or more surfaces defining one or more openings in the structure. In these embodiments, a region of space not associated with any physical portion of the structure may extend over at least part of an opening of the one or more openings. In other example embodiments, other structures may be employed to support or carry transducers of a transducer-based device provided by various flexible circuit structures (e.g., by various embodiments associated with, e.g., at least FIG. 2 or 4. In some embodiments, an elongated catheter member may be used to distribute the flexible circuit structure based transducers in a linear or curvilinear array. Basket catheters or balloon catheters may be used to distribute the flexible circuit structure based transducers in a two-dimensional or three-dimensional array.

In various example embodiments, the energy transmission surface 319 of each electrode 315 is provided by an electrically conductive surface. In some embodiments, each of the electrodes 315 is located on various surfaces of an elongate member 304 (e.g., front surfaces 318*a* or back surfaces 318*b*). In some embodiments, various electrodes 315 are located on one, but not both of the respective front surface 318*a* and respective back surface 318*b* of each of various ones of the elongate members 304. For example, various electrodes 315 may be located only on the respective front surfaces 318*a* of each of the various ones of the elongate members 304. Three of the electrodes 315 are identified as electrodes 315*a*, 315*b* and 315*c* in FIG. 3B. Three of the energy transmission surfaces 319 are identified as 319*a*, 319*b* and 319*c* in FIG. 3B. In various embodiments, it is intended or designed to have the entirety of each of various ones of the energy transmission surfaces 319 be available or exposed (e.g., without some obstruction preventing at least some of the ability) to contact non-fluidic tissue at least when structure 308 is positioned in a bodily cavity in the expanded configuration. In various embodiments, it is intended or designed to have no portion of each of at least one of the energy transmission surfaces 319 contact fluidic tissue when the at least one of the energy transmission surfaces 319 contacts a contiguous portion of a non-fluidic tissue surface (e.g., a tissue surface that defines a tissue wall).

In various embodiments, the respective shape of various electrically conductive surfaces (e.g., energy transmission surfaces 319) of various ones of the electrodes 315 vary among the electrodes 315. In various embodiments, one or more dimensions or sizes of various electrically conductive surfaces (e.g., energy transmission surfaces 319) of at least some of the electrodes 315 vary among the electrodes 315. The shape or size variances associated with various ones of the electrodes 315 may be motivated for various reasons. For example, in various embodiments, the shapes or sizes of various ones of the electrodes 315 may be controlled in response to various size or dimensional constraints imposed by structure 308.

It should be noted that the present invention is not limited to any particular PFA device transducer arrangement, and the devices 200A, 300A, 400A are provided for illustration purposes only. Nonetheless, PFA devices with many PFA transducers/electrodes, such as PFA devices 200A, 300A may particularly benefit in some contexts from the circuitry disclosed herein, e.g., at least with respect to FIG. 5A and thereafter. For one example, PFA devices with many PFA transducers/electrodes have more semiconductor switches to control the PFA transducers/electrodes, thereby amplifying the potentially negative effect of parasitic capacitances present in the semiconductor switches. However, at least some of various embodiments of the present invention provide circuitry including at least one or more output pulse generation configurations or capacitor configurations that limit the effects of these parasitic capacitances and provide others of various benefits described herein.

It should be noted that, while particular examples of circuit component configurations are illustrated in the figures and described herein, such circuit components can be redesigned with different components, different numbers of components, or different configurations to achieve the same function or functions of the particular examples of circuit component configurations illustrated in the figures and described herein. For example, a single illustrated capacitor may be equivalently replaced with multiple smaller capacitors to still achieve the same function of the single capacitor. Accordingly, it is to be understood that such redesigns are included within the scope of the present invention. Further, the present invention is not limited to all or any portion of any of the particular examples of circuit component configurations illustrated in the figures and described herein, and it should be noted that such particular examples are merely provided for illustration purposes only.

FIG. 5A is schematic representation of a circuit 500 employed by a PFA system which may be the same as, or similar to, at least part of system 100, 200, 300, or device 400A, according to various embodiments. In this regard, the circuit 500 (or any of the circuit or circuit portions illustrated in FIG. 5A, 5B, 5C, 5D, 5E, 7, 8, or 9) may be implemented, e.g., as part of the controller system 324, as part of the energy source device system 340, or as part of each of the controller system 324 and the energy source device system 340, according to some embodiments. Regardless of the considered logical location of the circuit 500 (or any of the circuit or circuit portions illustrated in FIG. 5A, 5B, 5C, 5D, 5E, 7, 8, or 9), it may merely be considered that a controller system, such as controller system 324, is communicatively connected to the circuit 500 (or any of the circuit or circuit portions illustrated in FIG. 5A, 5B, 5C, 5D, 5E, 7, 8, or 9), according to various embodiments.

According to various embodiments, circuit 500 includes a high voltage pulse generation circuit 500A, which may include a high voltage supply 504. According to various embodiments, circuit 500 includes an output pulse generation circuit 500B. According to some embodiments, the high voltage pulse generation circuit 500A is electrically connected to the output pulse generation circuit 500B. In some embodiments, the high voltage pulse generation circuit 500A is electrically connected to the output pulse generation circuit 500B, e.g., by way of a conducting path or via one or more electrical components. In some embodiments, the high voltage pulse generation circuit 500A is electrically connected to the output pulse generation circuit 500B by an electromagnetic coupling (e.g., a transformer). It is noted that “electrically connected” may include an electrical connection including one or more switching devices as electrical components, according to some embodiments. It is understood that although various electrical components such as switches may selectively interrupt current flow, the presence of such elements shall still be considered to provide an electrical connection, according to some embodiments. For example, even if two objects have an electrical path between them that includes one or more switching devices that can selectively interrupt the flow of electricity along the electrical path, it may still be considered, at least in some contexts, that the two objects are electrically connected, according to some embodiments. The same analysis applies for other forms of electrical components, such as, but not limited to, capacitors or transformers, that allow electrical connection between two objects even though, e.g., the entire electrical path between them may not be formed of an uninterrupted path of conductive material. It is noted that “electrically connected” may include an electromagnetic coupling, according to some embodiments.

According to some embodiments, with reference to at least FIG. 5A and block 1002 of method 1000 in FIG. 10, the high voltage pulse generation circuit 500A is configured to deliver a high voltage pulse set 514 from the high voltage pulse generation circuit 500A to the output pulse generation circuit 500B (for example, as described below). Although the high voltage pulse set 514 is illustrated in FIG. 5A as including positive and negative voltage pulses (with an initial positive voltage component), such high voltage pulse set 514 may be monophasic, positive or negative, or may include positive and negative voltage pulses with a leading negative voltage component, or otherwise, according to various embodiments. In this regard, the invention is not limited to any particular configuration of the high voltage pulse set 514. Further in this regard, the invention is not limited to any particular waveform illustrated in the figures (such as high voltage pulse set 514, output pulse set 516, first high voltage pulse 514A, second high voltage pulse 514B, or pulse 600, discussed in more detail below), which are provided merely for illustration purposes. According to various embodiments, and with reference to at least FIG. 5A and block 1004 of method 1000 of FIG. 10, the output pulse generation circuit 500B is configured to generate an output pulse set 516 at least in response to the high voltage pulse set 514. According to various embodiments, the output pulse set 516 is deliverable, e.g., via a plurality of output switch sets 510 of the output pulse generation circuit 500B in some embodiments, to a set of selectable electrodes (e.g., electrodes 315, 415, or electrodes of transducers 220). According to various embodiments, the output pulse set 516 is configured to cause PFA of tissue. According to various embodiments, each output pulse in the output pulse set 516 is a high voltage pulse. In some embodiments, each output pulse in the output pulse set 516 has an amplitude in a range of, e.g., 150 V to 2,300 V, although other embodiments have higher voltage amplitudes. In some embodiments, each output pulse in the output pulse set 516 has a magnitude in a range of, e.g., 150 V to 2,300 V, although other embodiments have higher voltage magnitudes. It is noted that other voltage ranges are possible, and that a particular output pulse voltage may be dependent on the configuration of the electrode that delivers it. For example, needle electrodes can cause PFA over relatively low voltages (even tens of volts) due to their extreme voltage gradients, but only over a very small area which may not be suitable for some applications (e.g., treating atrial fibrillation). On the upper end of the voltage scale, output pulses having pulse widths in the nanosecond range are typically associated with much higher voltages. PFA may be considered to be a function of the voltage gradient one can achieve in the tissue. The voltages needed to achieve a particular voltage gradient may be considered to be driven directly by the electrode geometry/design and indirectly by any associated biophysical constraints (e.g., a desire to reduce occurrences of, for example, muscle contractions, arcing, and the formation of microbubbles).

According to various embodiments, the PFA output pulses are delivered to tissue during particular time intervals. According to various embodiments, delivery of the PFA output pulses to tissue may be limited to particular time intervals. For example, in some applications, delivery of the PFA output pulses may be limited to the refractory period of each of various cardiac cycles. Limiting high voltage output pulse delivery to the refractory period may be employed to reduce occurrences of certain adverse or fatal cardiac arrhythmias that may arise in response to the delivery of the high voltage pulses.

Figure 6:
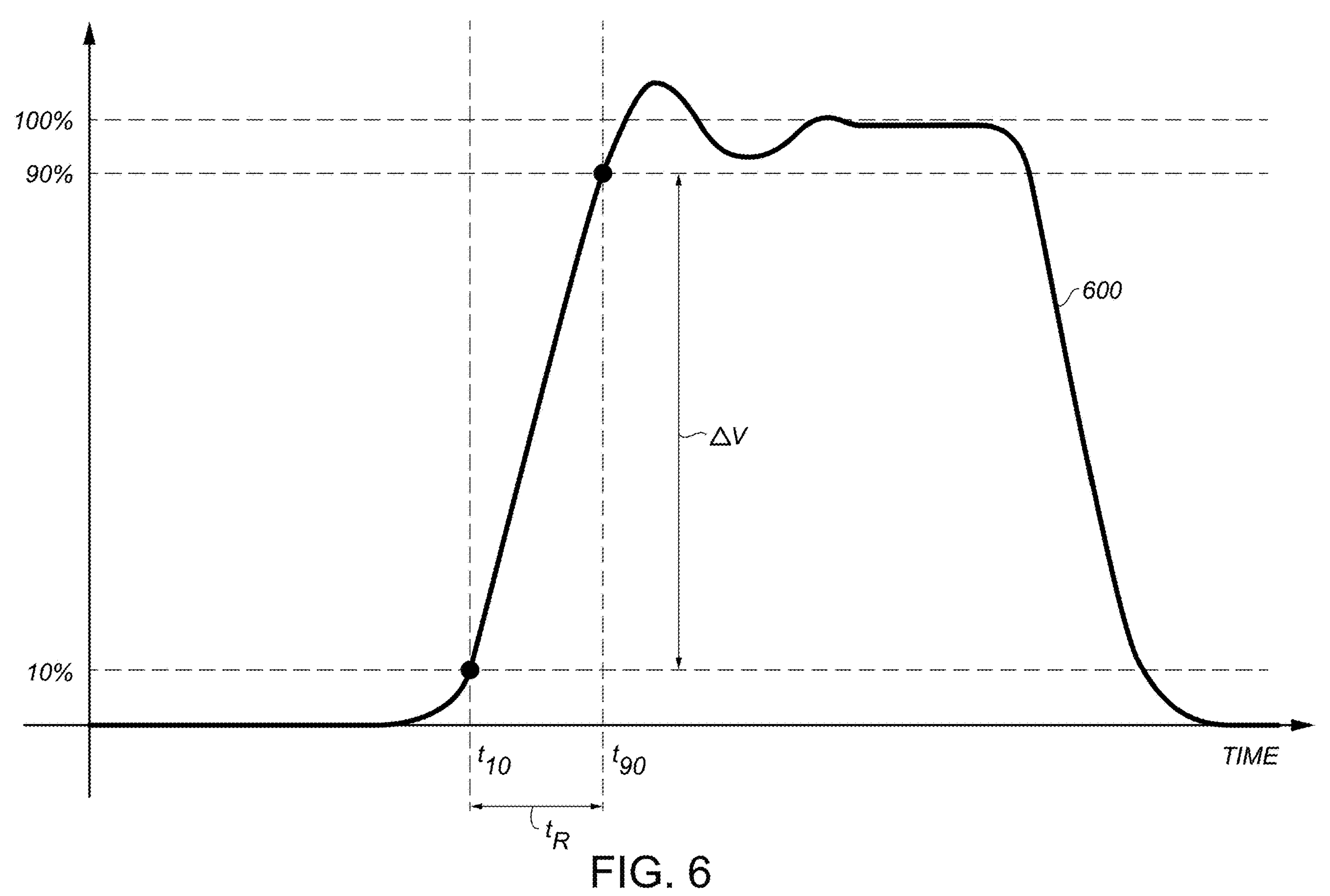
FIG. 6 includes a representation of an example voltage pulse to illustrate rise time and slew rate determinations, according to some embodiments.

According to some embodiments, each pulse in the output pulse set 516 has a rise time that is shorter than a rise time of at least one high voltage pulse in the high voltage pulse set 514. In some embodiments, rise time refers to the time it takes for the leading edge of a pulse (e.g., a voltage pulse or current pulse) to rise from a lower threshold value to an upper threshold value. Fall time is the time it takes for the pulse to move from the upper threshold value to the lower threshold value, according to some embodiments. In some embodiments, the upper threshold value is a maximum or peak value (maximum or peak voltage value or maximum or peak current value) of the pulse, and the lower threshold value is the minimum or lowest value (minimum or lowest voltage value or minimum or lowest current value) of the pulse. In some embodiments, the upper threshold value is a first percentage (e.g., in a range of 80% to 100%) of the maximum or peak value of the pulse, and the lower threshold value is a second percentage (e.g., in a range of 0% to 20%) of the maximum or peak value of the pulse, the second percentage lower than the first percentage. In some embodiments, the upper threshold value is a first percentage (e.g., in a range of 80% to 100%) of the maximum sustained value (e.g., a maximum sustained voltage) of the pulse, and the lower threshold value is a second percentage (e.g., in a range of 0% to 20%) of the maximum sustained value of the pulse, the second percentage lower than the first percentage. For example, FIG. 6 shows an example pulse 600 in which the rise time $t_R$ is determined as the time elapsed from the time $t_{10}$, at which a lower threshold of 10% of maximum sustained voltage is reached, to a time $t_{90}$, at which an upper threshold of 90% of maximum sustained voltage is reached. It is noted that a rise time may be defined for an electric current pulse in a similar manner.

Slew rate is defined as the change of voltage or current per unit of time. For example, the slew rate of the voltage pulse of FIG. 6, may be expressed as the ratio of the change in voltage $\Delta V$ (e.g., between the 90% threshold value and the 10% threshold value in this particular example) and the rise time. As described in further detail below, establishing a relatively larger rise time of the at least one high voltage pulse in the high voltage pulse set 514 can reduce, for a given voltage, its slew rate and alleviate or otherwise reduce undesired current driven through the patient via the parasitic capacitance of the nominally open output switches, when the output switch sets 510 are semiconductor switches or other switches having significant parasitic electrical circuit elements. In this regard, in some embodiments, the rise time of the at least one high voltage pulse in the high voltage pulse set 514 is controlled (e.g., relatively increased) to relatively reduce the pulse slew rate for a given voltage, such that each pulse in the output pulse set 516 is controlled to have a rise time that is shorter than a rise time of at least one high voltage pulse in the high voltage pulse set. Such an output pulse generation configuration, among other benefits, limits the effects of parasitic capacitances present in implicated semiconductor switches, such as semiconductor switches of output switch sets 510, which provide one or more output pulses in the output pulse set 516 to one or more electrodes (e.g., electrodes 315, 415 or electrodes of transducers 220), according to some embodiments.

According to various embodiments, the output pulse generation circuit 500B includes a first capacitor 502A (indicated as C1 in FIG. 5A) and a second capacitor 502B (indicated as C2 in FIG. 5A). According to some embodiments, a plurality of switches 506 electrically connect the first capacitor 502A and the second capacitor 502B to the high voltage supply 504. According to various embodiments, first capacitor 502A and second capacitor 502B are electrically connected between the output switch sets 510 of the output pulse generation circuit 500B and the high voltage supply 504 of the high voltage pulse generation circuit 500A.

According to various embodiments, output switch sets 510 are electrically connected to the first capacitor 502A and the second capacitor 502B to receive energy therefrom, and are electrically connected to the plurality of output switch sets 510, which, in turn, are electrically connected to the set of selectable electrodes (e.g., electrodes 315, 415 or electrodes of transducers 220). According to various embodiments, output switch sets 510 are controllable to allow the delivery of high voltage output pulses from selected electrodes (e.g., electrodes 315, 415 or electrodes of transducers 220), the output pulses configured to cause PFA in tissue, such high voltage output pulses generated at least in part in response to or from energy stored in the first capacitor 502A and the second capacitor 502B, as described in more detail below with respect to at least FIG. 5D.

According to various embodiments, the first and second capacitors 502A and 502B are preferably safety rated capacitors designed to not fail in a short circuit manner. In some embodiments, each of the first capacitor 502A and the second capacitor 502B is a Class-Y capacitor according to IEC 60384-14. Class-Y safety capacitors are designed to fail open. In some embodiments, each of the first capacitor 502A and the second capacitor 502B is either a Class-Y1 capacitor or a Class-Y2 capacitor. Class-Y1 application voltages range from 250 to 500 VAC (nominal), while Class-Y2 application voltages range from 250 to 300 VAC (nominal). It is noted that these Class-Y1 and Class-Y2 capacitor voltage ratings are typically applicable to AC voltages, and that these capacitors typically have higher DC voltage ratings. Such safety rated capacitors, among other benefits, reduce risk of directly exposing a patient to direct current, or pulsed current of an unacceptable duration, in a failure state.

According to some embodiments, a plurality of switches 506 electrically connect the first capacitor 502A and the second capacitor 502B to the high voltage supply 504. The implementation of first capacitor 502A and second capacitor 502B may be motivated for different reasons. According to some embodiments, capacitors 502A, 502B may be used to help ensure that that failures of at least some of the output switch sets 510 alone cannot result in electrical current from the high voltage supply 504 flowing through the patient. For example, in the state in which each of switch 506-1 (indicated as S1 in FIG. 5A) and switch 506-4 (indicated as S4 in FIG. 5A) is closed, failure of two or more output switch sets 510 would, in the absence of first capacitor 502A and second capacitor 502B, result in a direct connection of the high voltage supply 504 across patient tissue via the electrodes (e.g., electrodes 315, 415 or electrodes of transducers 220) associated with the failed output switch sets 510. Large electrical currents (e.g., DC currents of 10 amps in the case of 1 kV supply voltage/100 ohm estimated patient resistance) could flow, causing substantial electric shock, burns, or other adverse effects, and even comparatively small electrical currents (e.g., 50 μA) may still be harmful. However, with either first capacitor 502A or second capacitor 502B in the circuit 500, electrical current can only flow until the capacitance is charged, thus limiting the duration of the fault current and preventing or limiting the severity of any resulting electric shock or burn. Including both first capacitor 502A and second capacitor 502B ensures that this protection mechanism operates correctly even if one of the two capacitors fails short circuit. It is particularly noted that since the process of charging the first capacitor 502A and the second capacitor 502B is separate from the process of delivering an output pulse to an electrode set (e.g., electrodes 315, 415 or electrodes of transducers 220) via corresponding output switches of the output switch sets 510, the charging can be done with a much lower voltage slew rate, limiting the undesired current driven through the patient via the parasitic capacitance of the nominally open output switches when the output switches are semiconductor output switches.

In some embodiments, the high voltage pulse generation circuit 500A is electrically connected to the first capacitor 502A and the second capacitor 502B to deliver the high voltage pulse set 514 to the first capacitor 502A and the second capacitor 502B. In some embodiments, the PFA system (e.g., 100, 200, 300, or 400) includes a controller system (e.g., controller system 324) communicatively connected to circuit 500. According to various embodiments, the controller system 324 is configured (e.g., by a program including program instructions or by a circuit configuration) to execute actions associated with one or more of the blocks of method FIGS. 10-12. In this regard, in some embodiments, the controller system 324 is configured to cause the high voltage pulse generation circuit 500A to deliver a first subset of the high voltage pulse set 514 to the output pulse generation circuit 500B to charge the first capacitor 502A and the second capacitor 502B. According to some embodiments, the first subset of the high voltage pulse set is less (e.g., numbers fewer) than all of the high voltage pulse set. For example, in some embodiments, the high voltage pulse generation circuit 500A is electrically connected to the first capacitor 502A and the second capacitor 502B to deliver at least a first high voltage pulse 514A (FIG. 5B) in the high voltage pulse set 514 to the first capacitor 502A and the second capacitor 502B. According to various embodiments, the first high voltage pulse 514A may be delivered to the first capacitor 502A and the second capacitor 502B to charge the first capacitor 502A and the second capacitor 502B.

In some embodiments, the controller system 324 is configured to cause the high voltage pulse generation circuit 500A to deliver a second subset of the high voltage pulse set 514 to the output pulse generation circuit 500B to increase a voltage across a portion of the output pulse generation circuit 500B to a magnitude greater than a magnitude of the first subset of the high voltage pulse set. In this regard it is noted that the term "magnitude" as used herein, refers to the absolute value of the voltage, regardless of polarity. In various embodiments, "magnitude" may refer to a peak absolute value (e.g., an absolute value of a peak amplitude in some embodiments) or a sustained maximum absolute value (e.g., an absolute value of a sustained operating amplitude, such as in a sustained plateau region of a pulse, according to some embodiments). According to various embodiments, the second subset of the high voltage pulse set 514 is less (e.g., numbers fewer) than all of the high voltage pulse set 514. According to some embodiments, the second subset of the high voltage pulse set 514 is mutually exclusive with the first subset of the high voltage pulse set 514. For example, in some embodiments, the high voltage pulse set 514 delivered by the high voltage pulse generation circuit 500A includes at least the first high voltage pulse 514A and a second high voltage pulse 514B (e.g., FIG. 5C), such that the second high voltage pulse 514B is different than (e.g., mutually exclusive of) the first high voltage pulse 514A, according to some embodiments. In some embodiments, the first high voltage pulse 514A has a polarity that is opposite to a polarity of the second high voltage pulse 514B. According to various embodiments, the high voltage pulse generation circuit 500A is electrically connected to the first capacitor 502A and the second capacitor 502B to deliver the first high voltage pulse 514A, the second high voltage pulse 514B, or the first high voltage pulse 514A and the second high voltage pulse 514B to the first capacitor 502A and the second capacitor 502B (e.g., with the first high voltage pulse 514A and the second high voltage pulse 514B having opposite polarities, according to some embodiments). It is noted that each of the first high voltage pulse 514A and the second high voltage pulse 514B may, in some embodiments, have opposite polarities than those shown in respective ones of FIGS. 5B and 5C.

With reference to the example of FIG. 5A, high voltage supply 504 includes a first voltage supply 504A and a second voltage supply 504B although both supplies could be replaced by a single supply in some embodiments. The reason for using split supplies may be motivated for various reasons. For example, split supplies may help to reduce the magnitude of certain voltages appearing across certain isolation barriers (not shown, e.g., between the control (e.g., logic) circuitry and the high voltage circuitry), which in turn reduces the safety related requirements for those barriers (e.g., minimum spacings and test voltage requirements).

According to various embodiments, activation of various ones of the switches 506 (described in further detail below with respect to at least FIG. 5B and FIG. 5C) can be used to provide the first high voltage pulse 514A (e.g., +1,000 V nominal, by way of non-limiting example) and the second high voltage pulse 514B of opposite polarity (e.g., −1,000 V nominal by way of non-limiting example) to the first capacitor 502A and the second capacitor 502B.

According to various embodiments, controller system 324 may be configured to cause the high voltage pulse generation circuit 500A to deliver at least the first high voltage pulse 514A to the output pulse generation circuit 500B to charge the first capacitor 502A and the second capacitor 502B. According to various embodiments, a duration of the first high voltage pulse 514A is sufficient to at least charge the first capacitor 502A and the second capacitor 502B to desired levels. In some embodiments, delivery of the first high voltage pulse 514A is terminated after the first capacitor 502A and the second capacitor 502B have been charged to desired levels. In some embodiments, delivery of the second high voltage pulse 514B is initiated after delivery of the first high voltage pulse 514A has been terminated. According to some embodiments, delivery of the first high voltage pulse 514A is terminated prior to delivery of each output pulse of the output pulse set 516. According to some embodiments, delivery of the first high voltage pulse 514A is terminated prior to delivery of any output pulse of the output pulse set 516.

According to some embodiments, controller system 324 may be configured to cause, during at least part of the delivery of at least the second high voltage pulse 514B to the output pulse generation circuit 500B, a voltage across a portion of the output pulse generation circuit 500B to increase to a magnitude greater than a magnitude of the first high voltage pulse 514A. According to various embodiments, the portion of the output pulse generation circuit 500B, whose voltage is increased to a magnitude greater than a magnitude of the first high voltage pulse 514A, is an output bus 518 electrically connected to the set of selectable electrodes (e.g., a set of the electrodes 315, 415 or electrodes of transducers 220, according to some embodiments).

Reducing parasitic currents resulting from the parasitic capacitances of any of the open output switches of the output switch sets 510 is one of several benefits provided by at least some embodiments of the present invention. The implementation of first capacitor 502A and second capacitor 502B can provide other benefits. For example, in some embodiments, the first capacitor 502A and the second capacitor 502B can be connected to the high voltage supply 504 via switch 506-3 and switch 506-2 (described in further detail below) to receive a first high voltage pulse 514A (e.g., a +1,000 V pulse by way of non-limiting example) resulting in each of first capacitor 502A and second capacitor 502B being charged to approximately or nominally (e.g., disregarding component tolerances, in some embodiments) half the voltage of the high voltage supply 504 (for example, as measured between BRIDGE.VPP and BRIDGE.VNN in FIG. 5A). In various embodiments, each of first capacitor 502A and second capacitor 502B is charged to within a range of 5%, within a range of 10%, or within a range of 20% of half the voltage of the high voltage supply 504, although other embodiments have other percentages. The high voltage supply 504 may then be connected to the capacitors 502A, 502B via switches 506-4 and 506-1 (described in further detail below) to apply a second high voltage pulse 514B (e.g., −1000 V pulse by way of non-limiting example), resulting in approximately or nominally (e.g., disregarding component tolerances, in some embodiments) double the voltage of the high voltage supply 504 appearing across nodes LINK.VPP and LINK.VNN in FIG. 5A (e.g., across the output switches connected to electrodes 315, 415 or electrodes of transducers 220), potentially permitting the use of a high voltage supply 504 with a lower maximum output voltage than would otherwise be required for a given output voltage. Such a lower maximum output voltage of the high voltage supply 504 may provide enhanced safety benefits or reduced cost in some contexts. In various embodiments, the second high voltage pulse 514B is within a range of 5%, within a range of 10%, or within a range of 20% of double the voltage of the high voltage supply 504 appearing across nodes LINK.VPP and LINK.VNN in FIG. 5A.

In some embodiments, the controller system 324 is configured to cause the high voltage pulse generation circuit 500A to deliver the second high voltage pulse 514B to the first capacitor 502A and the second capacitor 502B after the first high voltage pulse 514A has been delivered to the first capacitor 502A and the second capacitor 502B. According to some embodiments, the controller system 324 is configured to cause the voltage across the portion of the output pulse generation circuit 500B (e.g., the output bus connected to the electrodes (e.g., electrodes 315, 415 or electrodes of transducers 220)) to increase to the magnitude greater than the magnitude of the first high voltage pulse 514A after causing each of the first capacitor 502A and the second capacitor 502B to be charged in response to the delivery of at least the first high voltage pulse 514A by the high voltage pulse generation circuit 500A to the output pulse generation circuit 500B. Advantageously, voltage of each output pulse of the output pulse set 516 produced by the output pulse generation circuit 500B may be increased beyond that of the high voltage supply 504.

According to some embodiments, each output pulse of the output pulse set 516 is an output voltage pulse, and the controller system 324 is configured to cause, during the delivery of at least part of the second high voltage pulse 514B, the output pulse generation circuit 500B to deliver each output voltage pulse of the output pulse set 516 with a magnitude (e.g., an amplitude in some embodiments) that is greater than a magnitude of the first high voltage pulse 514A. In some embodiments, each output pulse of the output pulse set 516 is an output voltage pulse, and the controller system 324 is configured to cause, after the voltage across the portion of the output pulse generation circuit 500B (e.g., an output bus connected to the electrodes (e.g., electrodes 315, 415 or electrodes of transducers 220)) is increased to the magnitude greater than the magnitude of the first high voltage pulse 514A, the output pulse generation circuit 500B to deliver each output voltage pulse of the output pulse set 516 with a magnitude (e.g., an amplitude in some embodiments) that is greater than the magnitude of the first high voltage pulse 514A. According to some embodiments, each output pulse of the output pulse set 516 is an output voltage pulse, and the controller system 324 is configured to cause the output pulse generation circuit 500B to deliver each output voltage pulse of the output pulse set 516 with a magnitude (e.g., an amplitude in some embodiments) that is greater than each of a magnitude (e.g., amplitude in some embodiments) of the first high voltage pulse 514A and a magnitude (e.g., amplitude in some embodiments) of the second high voltage pulse 514B. Such a configuration where each output voltage pulse of the output pulse set 516 (produced by the output pulse generation circuit 500B) may have an increased voltage as compared to either of the first high voltage pulse 514A and the second high voltage pulse 514B, according to some embodiments.

In some embodiments, the controller system 324 is configured to cause the output pulse generation circuit 500B to at least partially discharge the first capacitor 502A and the second capacitor 502B during at least part of the delivery of the second high voltage pulse 514B to the first capacitor 502A and the second capacitor 502B. For example, in some embodiments, delivery of at least some output pulses of the output pulse set 516 at least partially discharges the first capacitor 502A and the second capacitor 502B. In some embodiments, energy is stored in each of the first capacitor 502A and the second capacitor 502B in response to the delivery of the first high voltage pulse 514A to the first capacitor 502A and the second capacitor 502B, and each output pulse of the output pulse set 516 includes a portion of the energy stored in each of the first capacitor 502A and the second capacitor 502B. For example, the output pulse set 516 produced by the output pulse generation circuit 500B may utilize energy stored in the first capacitor 502A and the second capacitor 502B, according to some embodiments.

According to various embodiments, each pulse in the output pulse set 516 has a rise time that is shorter than the rise time of the at least one high voltage pulse in the high voltage pulse set 514. The at least one high voltage pulse in the high voltage pulse set 514 may include the second high voltage pulse 514B, such that each pulse in the output pulse set 516 has a rise time that is shorter than a rise time of at least the second high voltage pulse 514B in the high voltage pulse set 514. As described above, such an output pulse set 516 generation configuration, among other benefits, limits the effects of parasitic currents resulting from capacitances present in implicated switches, such as semiconductor switches of output switch sets 510, which provide one or more output pulses in the output pulse set 516 to one or more electrodes (e.g., electrodes 315, 415 or electrodes of transducers 220), according to some embodiments.

Figure 5B:
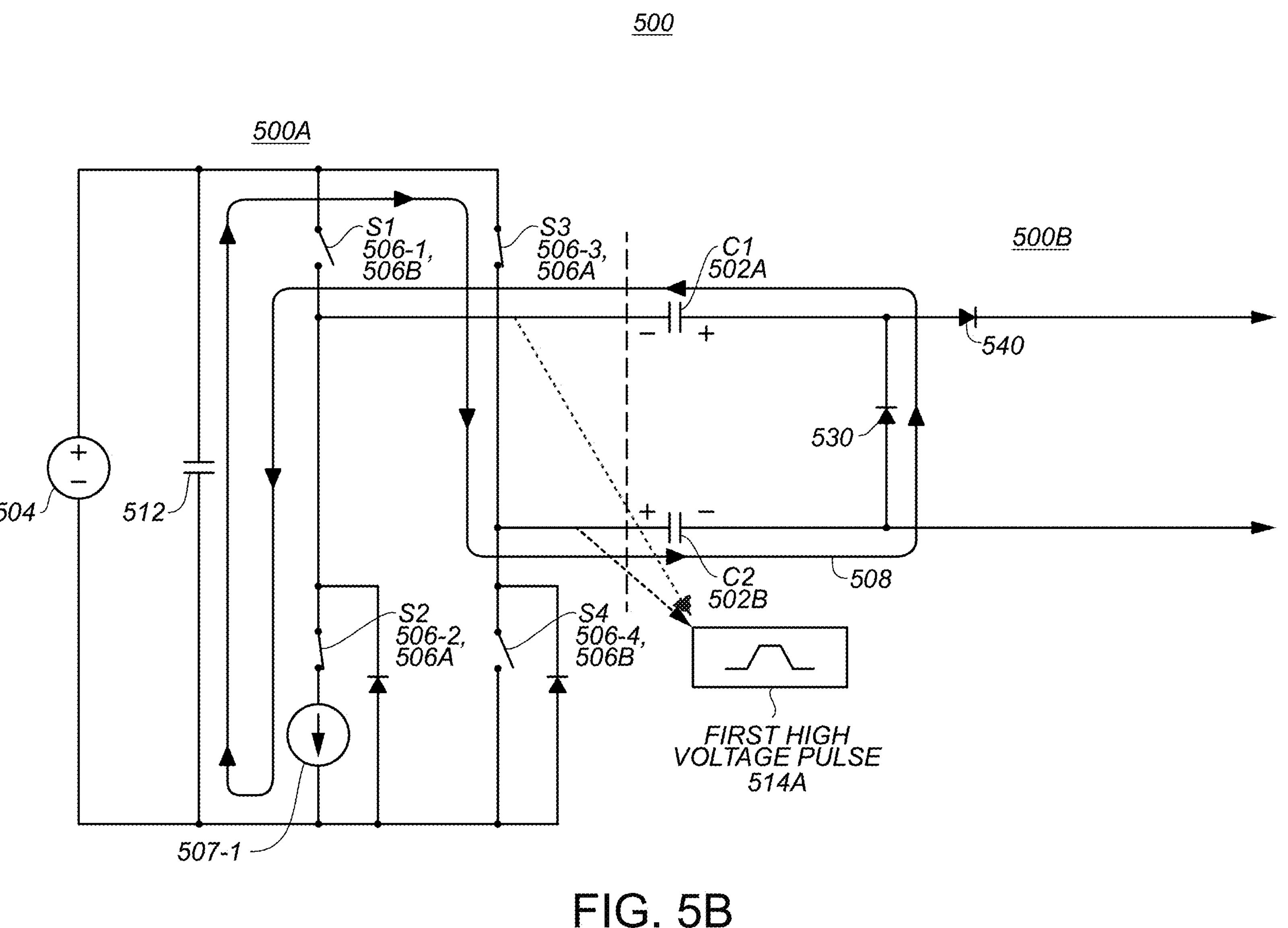
FIG. 5B includes a schematic representation of a portion of a circuit in a first charging switch state employed by a pulsed field ablation system, according to some embodiments, wherein such portion of a circuit may be a portion of the circuit of FIG. 5A, according to some embodiments.

With reference to at least FIGS. 5A-5D, a description will now be provided of methods or sequences of actions that may be employed or executed by circuit 500, according to some embodiments. According to various embodiments, the high voltage pulse generation circuit 500A includes a first group of switches 506A electrically connected to the first capacitor 502A and the second capacitor 502B, and a second group of switches 506B electrically connected to the first capacitor 502A and the second capacitor 502B. According to various embodiments, the first group of switches 506A includes switch 506-2 (e.g., indicated as S2 in FIGS. 5A, 5B, 5C and 5D) and switch 506-3 (e.g., indicated as S3 in FIGS. 5A, 5B, 5C and 5D). According to various embodiments, the second group of switches 506B includes switch 506-1 (e.g., indicated as S1 in FIGS. 5A, 5B, 5C and 5D) and switch 506-4 (e.g., indicated as S4 in FIGS. 5A, 5B, 5C and 5D). According to various embodiments, the controller system 324 is configured to cause (a) each switch in the first group of switches 506A to be in a respective NON-OPEN state with each switch in the second group of switches 506B in a respective OPEN state during a delivery of the above-discussed first high voltage pulse 514A to the output pulse generation circuit 500B. For example, according to some embodiments, FIG. 5B is a schematic representation of a portion of circuit 500 indicating a current flow path associated with the delivery of the first high voltage pulse 514A under the influence of the switch state (a) described above. In FIG. 5B, the first group of switches 506A includes switch 506-3 and switch 506-2, each of which is schematically shown in a respective NON-OPEN state, while the second group of switches 506B includes switch 506-1 and switch 506-4, each schematically shown in a respective OPEN state. In various embodiments associated with FIG. 5B, switch 506-2 and switch 506-3 are in series, and accordingly, the act of limiting the electric current flowing in switch 506-2 (e.g., under the influence of the NON-OPEN state) also serves to limit the current flowing in switch 506-3. In various embodiments associated with FIG. 5B, since the first and second capacitors 502A, 502B are also in series with switch 506-2, switch 506-2 also limits the current in these capacitors. In various embodiments associated at least with FIG. 5B, diode 530 is provided to complete current flow path 508. Upon completion of delivery of the first high voltage pulse 514A in the circuit configuration of FIG. 5B, each of the first capacitor 502A and the second capacitor 502B is ultimately charged to approximately one half of the supply voltage of high voltage supply 504, according to some embodiments, with the exact division of voltage depending on component tolerances and any parasitic effects.

Figure 5C:
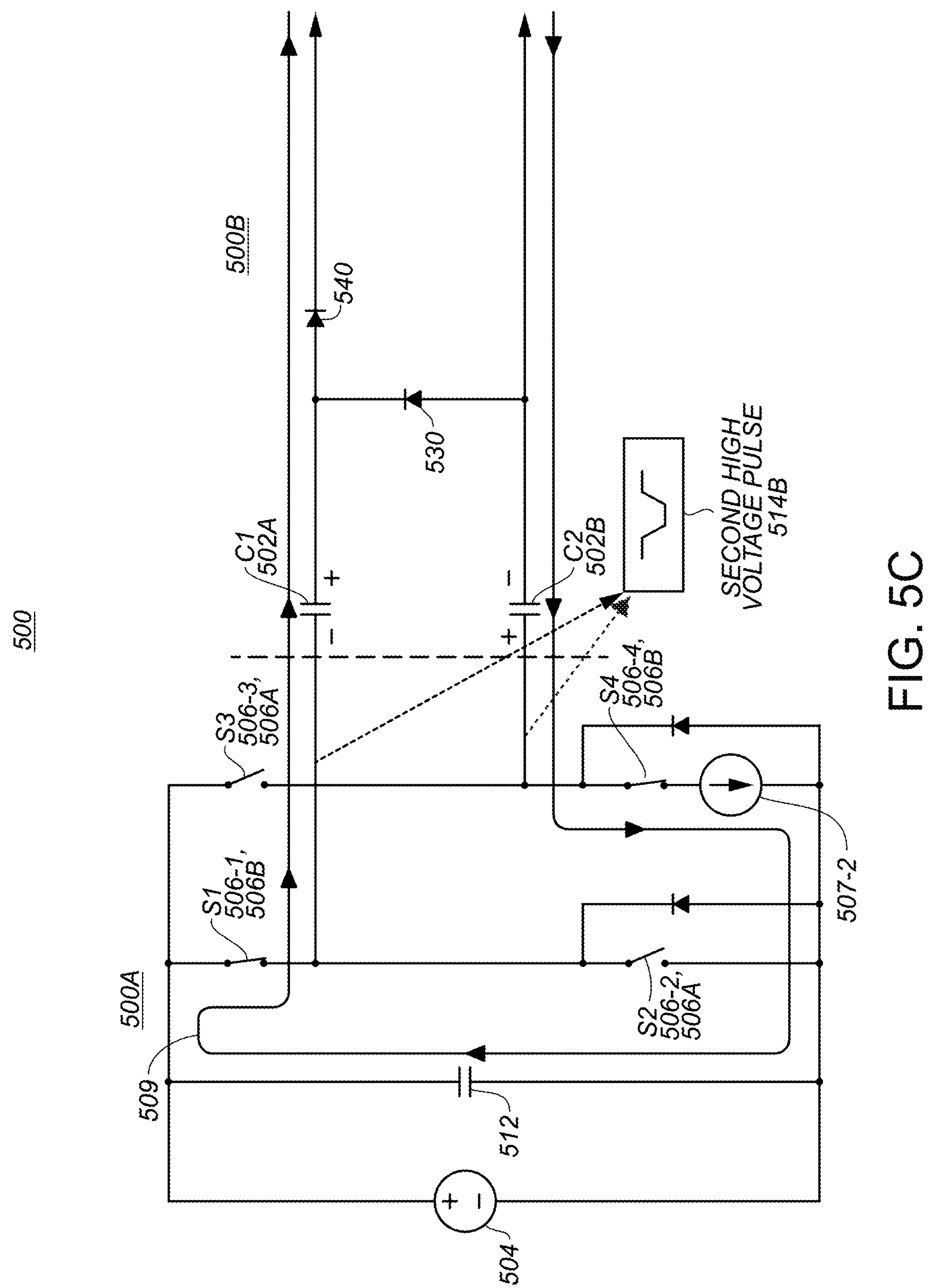
FIG. 5C includes a schematic representation of a portion of a circuit in a second charging switch state employed by a pulsed field ablation system, according to some embodiments, wherein such portion of a circuit may be a portion of the circuit of FIG. 5A.

According to various embodiments, the controller system 324 is configured to cause (b) each switch in the second group of switches 506B to be in a respective NON-OPEN state with each switch in the first group of switches 506A in a respective OPEN state during a delivery of the above-discussed second high voltage pulse 514B to the output pulse generation circuit 500B. For example, according to some embodiments, FIG. 5C is a schematic representation of a portion of circuit 500 indicating a current flow path associated with the delivery of the second high voltage pulse 514B under the influence of the switch state (b) described above. In FIG. 5C, the second group of switches 506B includes switch 506-1 and switch 506-4, each of which is schematically shown in a respective NON-OPEN state, while the first group of switches 506A includes switch 506-3 and switch 506-2, each schematically shown in a respective OPEN state. According to various embodiments, the first group of switches 506A is electrically connected in series, at least when the controller system 324 causes the above-discussed switch state (a) (e.g., FIG. 5B provides one example of such a switch state, according to some embodiments). According to various embodiments, the second group of switches 506B is electrically connected in series, at least when the controller system 324 causes the above-discussed switch state (b) (e.g., FIG. 5C provides one example of such a switch state, according to some embodiments). According to various embodiments, the first group of switches 506A and the second group of switches 506B are arranged in a full bridge configuration.

It is noted that, according to various embodiments, each respective OPEN state for each switch in the first group of switches 506A and for each switch in the second group of switches 506B is configured to prevent flow of electric current through the respective switch. It is noted that the prevention of the flow of electric current in this context need not require an absolute prevention of electric current through the respective switch, since at least semiconductor switches may have a small amount of leakage current even in an OPEN state. Accordingly, the OPEN states described herein that are configured to prevent flow of electric current are intended to refer to the natural OPEN state of the respective switch even if the respective switch has leakage current in that state, according to some embodiments.

According to various embodiments, each respective NON-OPEN state for each switch in the first group of switches 506A and for each switch in the second group of switches 506B is configured to allow a respective level of electric current to be deliverable through the respective switch. According to various embodiments, the respective level of electric current deliverable through the respective switch in the respective NON-OPEN state is greater than any electric current deliverable through the respective switch in the respective OPEN state. In some embodiments, the respective NON-OPEN state is a particular NON-OPEN state known as a CLOSED state in which the respective switch is controlled in a manner so as to allow the maximum amount of electric current (e.g., based on the rest of the components in an associated circuit) to flow through the respective switch. In some embodiments, the respective NON-OPEN state is configured to allow an amount of electric current flow through a particular switch to an amount greater than when the particular switch is in a respective OPEN state, but less than the amount of current that would flow though the respective switch if the respective switch were in its CLOSED state in an otherwise identical circuit configuration.

Figure 5D:
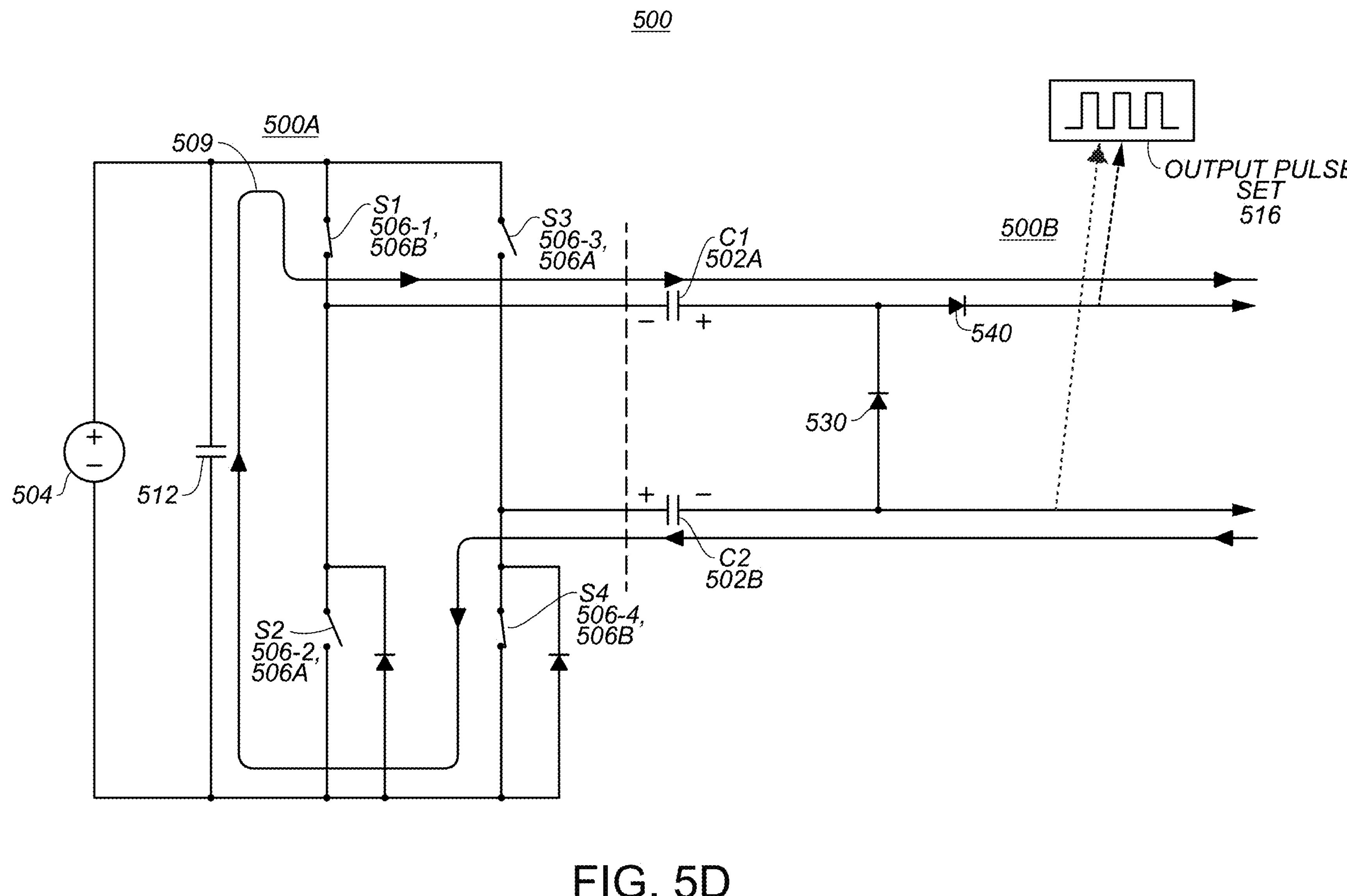
FIG. 5D includes a schematic representation of a portion of a circuit in an output pulse delivery state employed by a pulsed field ablation system, according to some embodiments, wherein such portion of a circuit may be a portion of the circuit of FIG. 5A.

In FIGS. 5B, 5C, and 5D, a particular switch is schematically indicated as being in a particular NON-OPEN state in various ways. For example, a particular switch is shown in FIGS. 5B, 5C, and 5D as being in a NON-OPEN state that is a CLOSED state with an associated switch symbol being shown in a "shut" or "closed" configuration, such as, e.g., the symbol for switch 506-3 in FIG. 5B. A particular switch is shown in FIGS. 5B, 5C, and 5D as being in a NON-OPEN state that is not a CLOSED state with an associated switch symbol being shown in a "shut" or "closed" configuration with the addition of an electrical schematic symbol for a current source, such as the illustration of switch 506-2 in FIG. 5B, with the current source symbol 507-1 in series with the switch 506-2. In other words, for example, in FIG. 5B, the current source symbol identified as 507-1 is shown in series with switch 506-2 (depicted in a shut configuration), thereby indicating that switch 506-2 is in a particular NON-OPEN state that allows for less current flow through the switch 506-2 than would be allowed in a CLOSED state. On the other hand, switch 506-3 in FIG. 5B (also depicted in a shut configuration) is not accompanied by any electric current source symbol, thereby indicating that switch 506-3 is in a particular NON-OPEN state that is a CLOSED state. In this regard, it should be noted that the current source symbols (e.g., 507-1 in FIG. 5B and 507-2 in FIG. 5C) do not represent a respective current source in the usual sense (i.e., they are not sources of energy), but they instead represent that the corresponding switch (e.g., switch 506-2 in FIG. 5B and switch 506-4 in FIG. 5C) is being controlled in a manner that limits the current through the corresponding switch. A particular switch is shown in FIGS. 5B, 5C and 5D as being in an OPEN state with an associated switch symbol being shown in an "open" configuration, such as, e.g., the symbol for switch 506-4 in FIG. 5B.

According to various embodiments, the controller system 324 may be configured to cause (c) each switch in the first group of switches 506A to switch between the respective OPEN state and the respective NON-OPEN state (which in some cases, may include a CLOSED state) with each switch in the second group of switches 506B in the respective OPEN state to generate the first high voltage pulse 514A (e.g., per the circuit configuration of FIG. 5B, according to some embodiments), and cause (d) each switch in the second group of switches 506B to switch between the respective OPEN state and the respective NON-OPEN state (which in some cases, may include a CLOSED state) with each switch in the first group of switches 506A in the respective OPEN state to generate the second high voltage pulse 514B (e.g., per the circuit configuration of FIG. 5C, according to some embodiments). According to various embodiments, the controller system 324 may be configured to generate the first high voltage pulse 514A or define characteristics of the first high voltage pulse 514A (e.g., pulse width, rise time, fall time, or combinations thereof, according to some embodiments) by causing, with each switch in the second group of switches 506B in the respective OPEN state, each switch in the first group of switches 506A to switch from the respective OPEN state to the respective NON-OPEN state (which in some cases, may include a CLOSED state) and then back to the respective OPEN state. According to various embodiments, the controller system 324 may be configured to generate the second high voltage pulse 514B or define characteristics of the second high voltage pulse 514B (e.g., pulse width, rise time, fall time, or combinations thereof, according to some embodiments) by causing, with each switch in the first group of switches 506A in the respective OPEN state, each switch in the second group of switches 506B to switch from the respective OPEN state to the respective NON-OPEN state (which in some cases, may include a CLOSED state) and then back to the respective OPEN state.

According to various embodiments, the respective NON-OPEN state for a first switch in the first group of switches 506A or the second group of switches 506B is a FIRST NON-OPEN state associated with the first switch. In some embodiments, the controller system 324 is configured to cause at least the first switch to switch between the respective OPEN state associated with the first switch and the FIRST NON-OPEN state associated with the first switch with each switch in the other of the first group of switches 506A and the second group of switches 506B to which the first switch does not belong in the OPEN state. According to some embodiments, the controller system 324 is configured to cause electric current deliverable through the first switch to be controlled, and the FIRST NON-OPEN state associated with the first switch is configured to control the electric current deliverable through the first switch to a first level to control the rise time of a particular high voltage pulse. For example, in some embodiments, the rise time of the first high voltage pulse 514A may be controlled in this manner. In some embodiments, the rise time of the second high voltage pulse 514B may be controlled in this manner. In some embodiments, the rise time of each of at least one high voltage pulse of the high voltage pulse set (e.g., the first high voltage pulse 514A, the second high voltage pulse 514B, or both, in some embodiments in which the high voltage pulse set 514 includes the first high voltage pulse 514A and the second high voltage pulse 514B) whose rise time is greater than the rise time of each output pulse of the output pulse set 516, as discussed above and otherwise herein, may be controlled in this manner.

Continuing with the preceding example of the first switch, according to various embodiments, the controller system 324 may be configured to cause, with each switch in the other of the first group of switches 506A and the second group of switches 506B to which the first switch does not belong in the respective OPEN state, at least a second switch in the first group of switches 506A or the second group of switches 506B to which the first switch belongs to switch between the respective OPEN state and a SECOND NON-OPEN state associated with the second switch, the SECOND NON-OPEN state associated with the second switch configured to control electric current deliverable though the second switch to a second level, the second level greater than the above-discussed first level. For example, in some embodiments associated with FIG. 5B, switch 506-2 may be considered to be a first switch in an associated FIRST NON-OPEN state, while the switch 506-3 may be considered to be a second switch in an associated SECOND NON-OPEN state. In some embodiments, the SECOND NON-OPEN state associated with the second switch is a CLOSED state that allows a greater level of current flow through the second switch than the FIRST NON-OPEN state associated with the first switch allows through the first switch. In a similar fashion, in some embodiments associated with FIG. 5C, switch 506-4 may be considered to be a first switch in an associated FIRST NON-OPEN state, while the switch 506-1 may be considered to be a second switch in an associated SECOND NON-OPEN state, the SECOND NON-OPEN state associated with the second switch being a CLOSED state that allows a greater level of current flow through the second switch than the FIRST NON-OPEN state associated with the first switch allows through the first switch.

In FIG. 5B, according to some embodiments, the rise time of the first high voltage pulse 514A is controlled by (e.g., by the controller system 324) controlling the current that is permitted to flow through switch 506-2, thereby controlling the rate of change of voltage on first capacitor 502A and second capacitor 502B. In FIG. 5C, according to some embodiments, the rise time of the second high voltage pulse 514B is controlled by (e.g., the controller system 324) controlling the current that is permitted to flow through switch 506-4, thereby controlling the rate of change of voltage on first capacitor 502A and second capacitor 502B. The following relationships may be used describe these effects:

$$Q = CV, \quad (A)$$

where Q=charge, C=capacitance, and V=voltage, $$I = Q/t, \quad (B)$$

where I=current, and t=time, $$I = C*(dV/dt) \quad (C)$$

where dV/dt is the change in voltage with time.

Relationship (C) is derived from relationships (A) and (B) and indicates that controlling the current controls the rate of change of voltage and can, as per some embodiments, control the rise time of one or more pulses in the high voltage pulse set 514 provided by the high voltage pulse generation circuit 500A (e.g., the first high voltage pulse 514A, the second high voltage pulse 514B, or both), according to some embodiments.

Various types of switches may be employed in each of the first group of switches 506A and the second group of switches 506B. In some embodiments, the above-discussed first switch is a semiconductor switch. In some embodiments, the semiconductor switch includes a transistor. By way of non-limiting example, the first switch may be a semiconductor switch that includes a transistor such as a bipolar junction transistor, an insulated-gate bipolar transistor (IGBT), a field effect transistor, or a MOSFET. It is noted that controlling the current flowing through a switch may be based on the type of switch that is employed. For example, when a semiconductor switch is employed, the terminology that is employed to describe the current control method as well as the actual physics of the control mechanism typically depend on the type of transistor that is employed (e.g., MOSFET vs IGBT).

Figure 7:
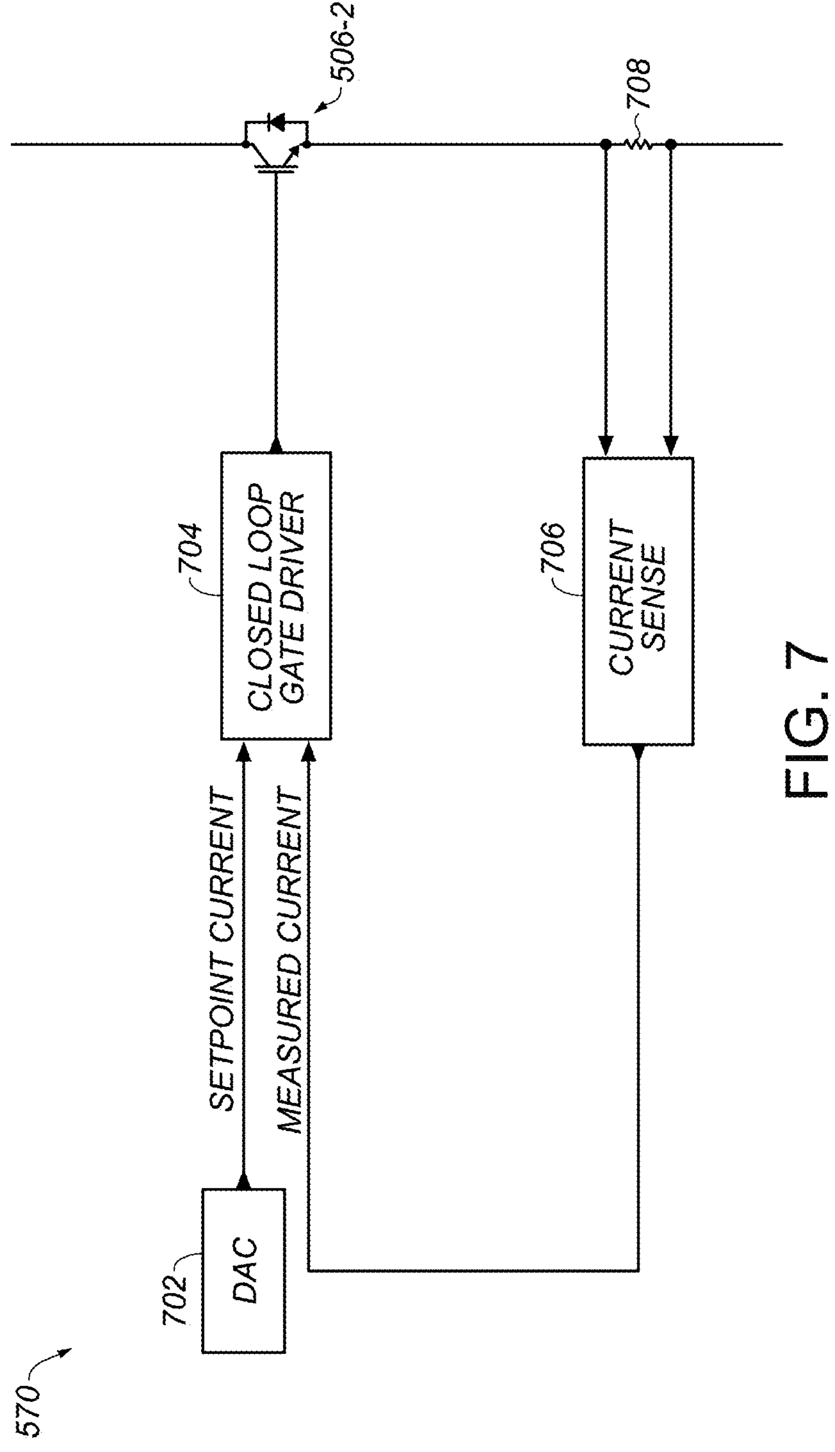
FIG. 7 includes a representation of a current control circuit that may be employed in a pulsed field ablation system, according to some embodiments.

According to various embodiments, a control circuit is electrically connected to at least one switch in a particular group of switches, such as the first group of switches 506A or the second group of switches 506B, to control electric current deliverable through the particular group of switches to control the rise time of a particular high voltage pulse, such as a high voltage pulse in the high voltage pulse set 514. For example, FIG. 7 shows a current control circuit 570 implemented, according to some embodiments, to control the current flow through the switch 506-2 (and consequently, switch 506-3, which is connected in series with switch 506-2) to control the rise time of the first high voltage pulse 514A. At least in this regard, the control circuit 570 may be referred to as an electric current control circuit in some embodiments, or a switch group electric current control circuit in some embodiments. It is noted that the terminology and physics associated with this current control may depend on the type of switch (e.g., MOSFET vs IGBT) that is employed. According to various embodiments, the current flowing in the switch is sensed, for example, by a current sense circuit 706 sensing the voltage drop across a small resistance (represented by resistor 708) in series with the respective switch (switch 506-2 in the example of FIG. 7). Other embodiments may use other methods of sensing current, such as a hall effect sensor or a current sense transformer, by way of non-limiting examples. The control circuit (e.g., the same as or similar to the control circuit 570) may then employ a closed loop gate driver circuit 704 to compare the measured current (represented in FIG. 7 as "MEASURED CURRENT") (or a voltage representing the measured current) to an input setpoint (or desired) current (represented in FIG. 7 as "SETPOINT CURRENT") (or a voltage representing the setpoint or desired current) provided by, for example, a digital-to-analog converter (DAC) 702 to adjust the control voltage or current applied to the control terminal (e.g., gate relative to emitter for an IGBT) of the corresponding switch (switch 506-2 in the example of FIG. 7) to change the impedance between the main current conducting terminals (e.g., collector and emitter for an IGBT) in order to bring the current to the desired level. According to various embodiments, the control circuit (e.g., the same as or similar to the control circuit 570) is a closed-loop electric current control circuit. According to various embodiments, a control circuit (e.g., the same as or similar to the control circuit 570) is electrically connected to at least one switch in the second group of switches 506B to control electric current deliverable through the second group of switches 506B to control the rise time of the second high voltage pulse 514B. According to various embodiments, the rise time of the second high voltage pulse 514B is controlled with a closed-loop electric current control circuit. It is noted that the term "switch" as used in this disclosure in the context of a semiconductor switch is not necessarily a single semiconductor component or relay. For example, in some embodiments, a plurality of semiconductor components may be connected in parallel to achieve a desired current rating, and as such the plurality of semiconductor components may collectively form a single switch.

Controlling the current through the first group of switches 506A, and consequently the rise time of the first high voltage pulse 514A, may be motivated for different reasons. For example, if one of switches 506-2 and 506-3 of the first group of switches 506A is not used to control the current, a very large current may result, and it is possible that components such as first capacitor 502A and second capacitor 502B may become damaged under the influence of this current.

According to some embodiments, the controller system 324 is configured to cause the above-discussed switch state "(b)" (e.g., FIG. 5C provides one example of such a switch state, according to some embodiments) after causing the above-discussed switch state "(a)" (e.g., FIG. 5B provides one example of such a switch state, according to some embodiments). For example, FIG. 5C shows an embodiment representing the particular states of the switches in the first group of switches 506A and the second group of switches 506B after the controller 324 has caused switch state (b). According to various embodiments, at least one high voltage pulse in the high voltage pulse set 514 includes the second high voltage pulse 514B, such that each pulse in the output pulse set 516 has a rise time that is shorter than a rise time of at least the second high voltage pulse 514B in the high voltage pulse set 514.

According to some embodiments, the controller system 324 is configured to cause the above-discussed switch state "(a)" (e.g., FIG. 5B provides one example of such a switch state, according to some embodiments) to increase voltage across the first capacitor and the second capacitor to a first magnitude, and the controller system 324 is configured to cause the above-discussed switch state "(b)" (e.g., FIG. 5C provides one example of such a switch state, according to some embodiments) to increase voltage across at least a first output switch set of the plurality of output switch sets 510 (e.g., FIG. 5A) to a second magnitude greater than the first magnitude. For instance, a comparison of FIGS. 5B and 5C indicates that the first capacitor 502A and the second capacitor 502B are connected in different series configurations in the two switch states, according to some embodiments. In particular, in FIG. 5C, the first capacitor 502A and the second capacitor 502B are connected in a series configuration in which their voltages approximately, or nominally, equal the supply voltage from high voltage supply 504, and sum with the supply voltage to produce approximately, or nominally, double the supply voltage across an output bus (e.g., output bus 518 in FIG. 5A, according to some embodiments) that connects to a plurality of output switch sets 510 (e.g., FIG. 5A), which are connected to a plurality of electrodes (e.g., electrodes 315, 415 or electrodes of transducers 220). It is noted that other nominal multiples of the supply voltage may be employed in other embodiments.

As shown in FIG. 5C, switch 506-4 is in a NON-OPEN state to limit the current through the capacitors 502A, 502B, according to some embodiments. According to various embodiments, limiting the current through the first capacitor 502A and the second capacitor 502B limits the rate of change of voltage across the output bus (e.g., output bus 518 in FIG. 5A, according to some embodiments), thereby advantageously limiting current that can flow through the parasitic capacitances of the output switch sets 510. In FIG. 5C, the current source symbol identified as 507-2 is shown in series with switch 506-4 (depicted in a shut configuration), thereby indicating that switch 506-4 is in a particular NON-OPEN state that allows for less current flow through the switch 506-4 than would be allowed in a CLOSED state. According to various embodiments, the at least one high voltage pulse in the high voltage pulse set 514 includes the second high voltage pulse 514B, such that each pulse in the output pulse set 516 has a rise time that is shorter than a rise time of at least the second high voltage pulse 514B in the high voltage pulse set 514.

FIG. 5D is a schematic representation of a portion of circuit 500 indicating a current flow path associated with the delivery of one or more output pulses of one or more output pulse sets, which may include output pulse set 516, according to some embodiments. According to various embodiments, switches 506-1 and 506-4 are in respective NON-OPEN states in the switch state of FIG. 5D, while switches 506-2 and switches 506-3 are in respective OPEN states. According to some embodiments, each of at least some of the switches 506, which have a particular NON-OPEN state in the switch state of FIG. 5C, maintain that particular NON-OPEN state when the controller system 324 causes delivery of the output pulses via the switch state of FIG. 5D. For example, once the output bus (e.g., output bus 518 in FIG. 5A, according to some embodiments) is charged to a final voltage sufficient to supply the output pulses in response to the switch state of FIG. 5C, switch 506-1 maintains a same NON-OPEN state as it employed in the switch state of FIG. 5C for the output-pulse delivery state of FIG. 5D, according to some embodiments.

According to some embodiments, each of at least some of the switches 506, which have a particular NON-OPEN state in the switch state of FIG. 5C, change that particular NON-OPEN state to a different particular NON-OPEN state when the controller system 324 causes delivery of the output pulses via the switch state of FIG. 5D. For example, in some embodiments, the NON-OPEN state for a first switch in the first group of switches 506A or the second group of switches 506B is a FIRST NON-OPEN state associated with the first switch. In some embodiments, the FIRST NON-OPEN state is configured to control electric current deliverable through the first switch to a first level. In some embodiments, the controller system 324 is configured to cause the first switch (e.g., switch 506-4 in one example) to switch between the FIRST NON-OPEN state (e.g., in the switch state of FIG. 5C) and a SECOND NON-OPEN state (e.g., in the switch state of FIG. 5D). In some embodiments, the SECOND NON-OPEN state associated with the first switch (e.g., switch 506-4 in one example) is configured to control electric current deliverable through the first switch to a second level greater than a first level (e.g., the switch 506-4 delivers more current in the NON-OPEN state of FIG. 5D than in the NON-OPEN state of FIG. 5C). In some embodiments, the controller system 324 is configured to cause the change of NON-OPEN switch states of the first switch, e.g., between the FIRST NON-OPEN state and the SECOND NON-OPEN state, after causing the above-discussed "(a)" and "(b)" switch states (e.g., FIG. 5B provides one example of switch state "(a)" and FIG. 5C provides one example of switch state "(b)", according to some embodiments).

According to some embodiments, the first switch is configurable to switch between a respective OPEN state associated with the first switch and the SECOND NON-OPEN state associated with the first switch. For example, switch 506-4 switches from the OPEN state in the switch state of FIG. 5B to the SECOND NON-OPEN state in the switch state of FIG. 5D, according to some embodiments.

While the above example with respect to switch 506-4 refers to a SECOND NON-OPEN state (e.g., in the switch state of FIG. 5D) that allows more current than a FIRST NON-OPEN state (e.g., in the switch state of FIG. 5C), the SECOND NON-OPEN state associated with the first switch may be a CLOSED state of the first switch, in some embodiments. The CLOSED state may be configured to allow maximum or substantially maximum electric current to be deliverable through the first switch, noting that the actual current that does flow is dependent on the other circuit components. In this context, in some embodiments, the controller system 324 is configured to cause the output pulse generation circuit 500B to discharge the first capacitor 502A and the second capacitor 502B with the first switch in the SECOND NON-OPEN state. In some embodiments, the controller system 324 is configured to cause the output pulse generation circuit 500B to generate the output pulse set 516 with the first switch in the SECOND NON-OPEN state. For example, in some embodiments in which switch 506-4 is considered the first switch, the switch 506-4 may be considered to be in a FIRST NON-OPEN state in FIG. 5C, and in a SECOND NON-OPEN state in FIG. 5D. In this regard, in some embodiments, once the output bus (e.g., output bus 518 in FIG. 5A, according to some embodiments) is charged to a final voltage upon conclusion of sufficient operation of the switch state of FIG. 5C, switch 506-4 is controlled by controller 324 to change from its FIRST NON-OPEN state in FIG. 5C to its SECOND NON-OPEN state in FIG. 5D. In this regard, in some embodiments, the SECOND NON-OPEN state of switch 506-4 in the switch state of FIG. 5D may be a CLOSED state configured to allow maximal current flow through the switch 506-4.

Such a configuration may be motivated for different reasons. For example, the FIRST NON-OPEN state (e.g., FIG. 5C in the present example) may limit current flow to reduce parasitic currents in the output switch sets 510, according to various embodiments. The SECOND NON-OPEN state (e.g., FIG. 5D in the present example) may allow for greater current flow during the subsequent generation of the output pulses (e.g., which may include output pulse set 516, according to some embodiments). According to various embodiments, the output pulses are generated by discharging energy from the first capacitor 502A and the second capacitor 502B. According to various embodiments, causing switch 506-4 to change from its FIRST NON-OPEN state to its SECOND NON-OPEN state allows for greater current flow between the output switch sets 510 and the first and second capacitors 502A, 502B, thereby providing less hinderance to the formation of the output pulses at a desired rate and amplitude. It is noted, according to some embodiments, that the controller system 324 may be configured to cause both the first capacitor 502A and the second capacitor 502B to concurrently at least partially discharge, and the controller system 324 may be configured to cause the switch states "(a)" (e.g., which may be the example switch state of FIG. 5B) and "(b)" (which may be the example switch state of FIG. 5C) prior to the concurrent discharge of both the first capacitor 502A and the second capacitor 502B (e.g., which may occur in the switch state of FIG. 5D), according to some embodiments.

According to various embodiments, the controller system 324 may be configured to cause the output pulse generation circuit 500B to generate the pulses in at least the output pulse set 516 by switching each output switch of at least one selected output switch of the output switch sets 510 between an OPEN state, associated with the output switch and configured to prevent flow of electric current therethrough, and a CLOSED state, associated with the output switch and configured to allow maximum or substantially maximum electric current to be deliverable therethrough. According to some embodiments, at least some of the switches in each output switch set of the plurality of output switch sets 510 are arranged in a half bridge configuration. According to various embodiments, at least one pair of switches in each output switch set of the plurality of output switch sets 510 is arranged in a half bridge configuration, for example, as shown in FIG. 5A by the arrangement of output switch sets 510. According to some embodiments, each half bridge has a high side switch (connected via a circuit path to the positive pole of the output, labeled "LINK.VPP" in the example of FIG. 5A) and a low side switch (connected via a circuit path to the negative pole of the output, labeled "LINK.VNN" in the example of FIG. 5A). According to various embodiments, each half bridge is associated with one electrode (e.g., electrodes 315, 415 or electrodes of transducers 220).

According to various embodiments, the controller system 324 may be configured to cause the output pulse generation circuit 500B to generate the pulses in at least the output pulse set 516 by switching one of the output switches in each of selected ones of the half bridge configurations between the respective OPEN and respective CLOSED states. For example, in some embodiments, a pulse is created by turning a high side output switch in a half bridge ON (e.g., the CLOSED switch state or a NON-OPEN switch state that is not a CLOSED switch state), while at the same time turning a low side output switch in a different half bridge ON (e.g., the CLOSED switch state or a NON-OPEN switch state that is not a CLOSED switch state).

According to various embodiments, a pulse is created at least in part by turning a high side output switch in a half bridge ON while concurrently maintaining the low side switch in the half bridge OFF (e.g., an OPEN switch state). According to various embodiments, a pulse is created at least in part by turning a low side output switch in a half bridge ON while concurrently maintaining the high side switch in the half bridge OFF. According to various embodiments, both the high side and low side output switch in a same half bridge are not concurrently turned ON, as this state may short circuit the output in some circuit configurations. According to various embodiments, a particular one of the output switches in each of the selected ones of the half bridge configurations is selected (e.g., by the controller 324) based on a desired polarity of the output pulse that is to be formed in response to switching the particular one of the output switches between the respective OPEN and respective CLOSED states. For example, in some embodiments, if it is desired to create a pulse between two electrodes E1 and E2 (not shown, but may be a pair of at least electrodes 315, 415 or electrodes of transducers 220, according to some embodiments) with a positive voltage (as defined by the voltage of E1 minus the voltage of E2 in this example), then a high side output switch in a half bridge associated with electrode E1 may be turned ON (e.g., the CLOSED switch state or a NON-OPEN switch state that is not a CLOSED switch state), while a low side output switch in a half bridge associated with electrode E2 may be turned ON (e.g., the CLOSED switch state or a NON-OPEN switch state that is not a CLOSED switch state). If it is desired to create a pulse with an opposite polarity (e.g., voltage of E2 is greater than that of E1), then a high side output switch in a half bridge associated with electrode E2 may be turned ON (e.g., the CLOSED switch state or a NON-OPEN switch state that is not a CLOSED switch state), while a low side output switch in a half bridge associated with electrode E1 may be turned ON (e.g., the CLOSED switch state or a NON-OPEN switch state that is not a CLOSED switch state), according to some embodiments.

According to some embodiments, each output switch of the plurality of output switch sets 510 is a semiconductor switch. In some embodiments, an output switch may include a plurality of semiconductor switches arranged in a parallel configuration. The output switch sets 510 can be switched from the OPEN state to the CLOSED state as quickly as desired, because limitation of the output pulse slew rate (e.g., of pulses in output pulse set 516), in some embodiments, is not necessary to provide the above-discussed reduction of negative effects of parasitic capacitances in semiconductor switches. On the other hand, the present inventors have determined, as discussed above, that controlling the slew rate of one or more of the high voltage pulses in the high voltage pulse set 514 does reduce negative effects of such parasitic capacitances. Accordingly, in some embodiments, the rise time of each pulse in each output pulse set 516 may beneficially have a rise time that is shorter than a rise time of at least one high voltage pulse in the high voltage pulse set 514 that is delivered to the output pulse generation circuit 500B, the rise time of the at least one high voltage pulse configured to limit parasitic currents in the output switch sets 510.

It is noted that, in various embodiments, delivery of the second high voltage pulse 514B may be terminated after a particular output pulse set 516 is delivered. In some embodiments, the controller system 324 may be configured to cause the above-discussed switch state "(a)" (e.g., FIG. 5B provides one example of such a switch state, according to some embodiments) after a particular output pulse set 516 is delivered. In some embodiments, the controller system 324 is configured to repeat switch state "(a)" and the above-discussed switch state "(b)" (e.g., FIG. 5C provides one example of such switch state "(b)", according to some embodiments) with each successive output pulse set (e.g., output pulse set 516) of a plurality of output pulse sets that is generated. In various embodiments, diode 540 may exist to essentially prevent (disregarding leakage) flow of current from the output bus 518 through either or both of capacitor C1 or capacitor C2 in the situation where the output bus voltage is greater than that on either of capacitor C1 or capacitor C2's terminals.

Figure 8:
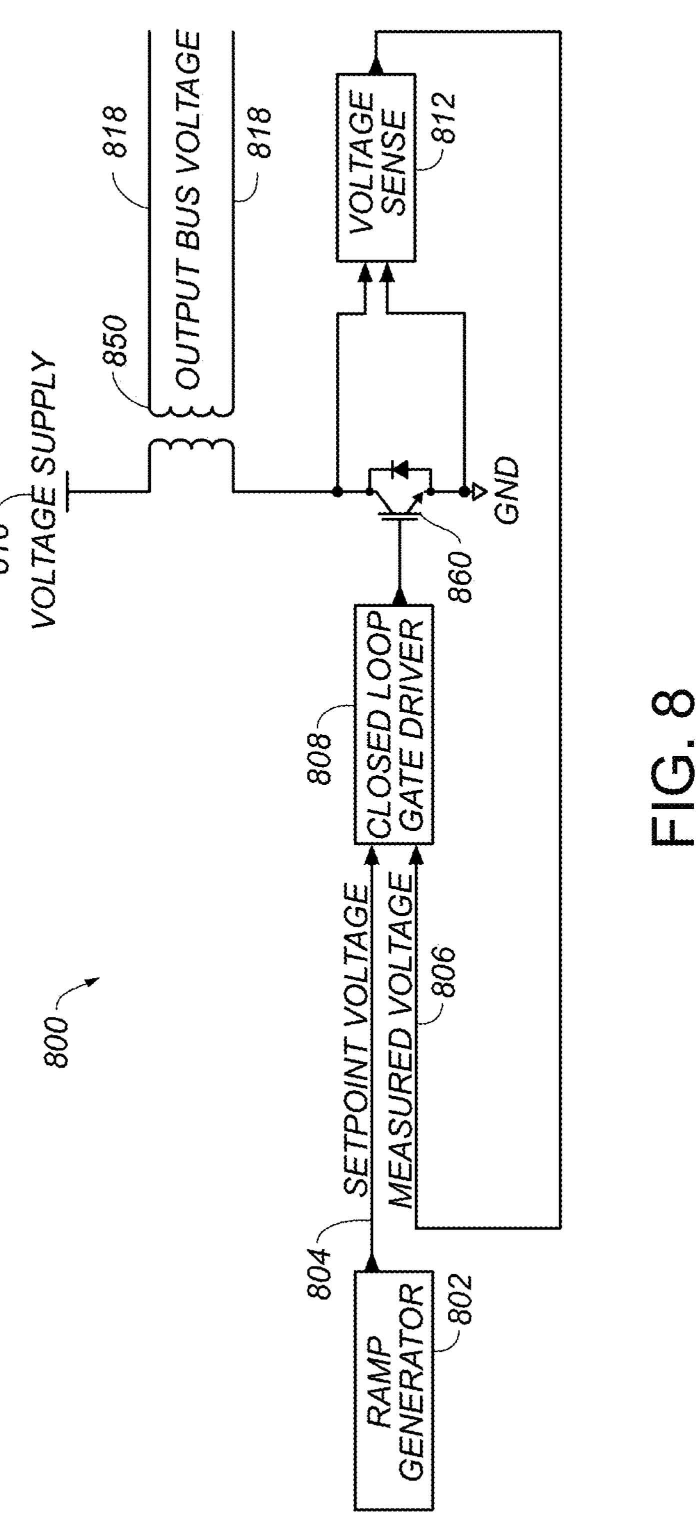
FIG. 8 includes a representation of a voltage control circuit including a transformer-based architecture that may be employed in a pulsed field ablation system, according to some embodiments.

In some embodiments described above, the output bus slew rate is controlled via controlling the slew rate of one or more pulses in the high voltage pulse set 514, which, in turn, limits negative effects of parasitic currents resulting from parasitic capacitances of semiconductor switches at least in output switch sets 510, among other benefits. It is noted, in some embodiments, that other circuit architectures may be employed to control the output bus slew rate in accordance with various embodiments of the present invention. According to some embodiments, control of the output bus voltage slew rate can also be implemented with a transformer-based architecture. FIG. 8 is a schematic diagram of a voltage control circuit 800 including a transformer-based architecture, according to some embodiments. According to some embodiments, the voltage control circuit 800 may represent an implementation of at least part of the high voltage pulse generation circuit 500A. In some embodiments, voltage control circuit 800 includes a transformer 850 and at least a first switch 860 electrically connected to the primary of the transformer 850. In some embodiments, the transformer 850 has a turn ratio of 1 to 4, although other embodiments utilize other turn ratios. In some embodiments, the first switch 860 is a semiconductor switch that includes a transistor. Various possible switches described above in relation to switches 506 may be employed as first switch 860, according to some embodiments. According to some embodiments, the output pulse generation circuit 500B is electrically connected to the secondary of the transformer 850. For example, according to some embodiments, the output bus 818 shown in FIG. 8 is connected to the secondary of the transformer 850, and, in some embodiments, the output bus 818 may be or be connected to the output pulse generation circuit 500B. Output switches sets (not shown in FIG. 8, but may be arranged in the same configuration shown in FIG. 5A, according to some embodiments) connect across the output bus 818, and it is the slew rate of the voltage across the output bus 818 that may preferably be controlled in accordance with some embodiments of the invention.

According to various embodiments, the slew rate of the output bus 818 is controlled by controlling the slew rate of the voltage applied to the primary of the transformer 850. According to some embodiments, this control may be achieved by connecting the transformer 850 and first switch 860 (shown as an IGBT in FIG. 8, with the understanding that other semiconductor switches may be employed in other embodiments) in series across a voltage supply 810. According to various embodiments, the first switch 860 may be operable to switch between (i) an OPEN state configured to provide a first voltage across the first switch 860, and (ii) a NON-OPEN state configured to provide a second voltage across the first switch 860, the second voltage across the first switch 860 in the NON-OPEN state less than the first voltage across the first switch 860 in the OPEN state. According to various embodiments, when the first switch 860 is in the OPEN state, the majority (e.g., all minus leakage in some embodiments) of the supply voltage 810 appears across the first switch 860 and the voltage across the transformer 850 is effectively zero.

Switching the first switch 860 between the OPEN state and a NON-OPEN state results in some fraction of the supply voltage appearing across the transformer 850. In some embodiments, the first switch 860 may be switched between the OPEN state and at least one NON-OPEN state in such a manner that the voltage across the transformer is ramped from effectively zero to effectively the full magnitude of the voltage supply. In some embodiments, a ramp generator circuit 802 (e.g., a circuit producing a linearly decreasing output voltage over time) may be used to provide an input setpoint voltage 804 to a closed loop gate driver circuit 808 controlling the first switch 860. In some embodiments, a voltage sense circuit 812 may be used to measure a voltage across the first switch 860 and to provide an input measured voltage 806 to the closed loop gate driver circuit 808. In some embodiments, the closed loop gate driver circuit 808 may use the difference (or error) between the input setpoint voltage 804 and the input measured voltage 806 in order to control the state (e.g., OPEN state or NON-OPEN states) of the first switch 860. According to some embodiments, the controller system 324, which may include at least some of the voltage control circuit 800 in some embodiments, may be configured to cause the first switch 860 to switch between the OPEN state and at least one NON-OPEN state to cause voltage across the first switch 860 to be controlled to a particular level to control the rise time of at least one high voltage pulse (e.g., of the high voltage pulse set 514) delivered via the transformer 850 to the output pulse generation circuit 500B (e.g., via output bus 818), which delivers an output pulse set 516 in response to the delivered at least one high voltage pulse, according to some embodiments. In some embodiments, each output pulse of the output pulse set 516 has a rise time that is shorter than a rise time of the at least one high voltage pulse. According to various embodiments, a control circuit (e.g., the same as or similar to at least part of the voltage control circuit 800) is electrically connected to the first switch 860 to control voltage across the first switch 860 to control the rise time of the at least one high voltage pulse (of the high voltage pulse set 514). At least in this regard, the control circuit (such as control circuit 800) may be referred to as a voltage control circuit in some embodiments (e.g., as compared to current control circuit 570 of FIG. 7). In some embodiments, the control circuit 800 is a closed-loop voltage control circuit.

Since the output voltage is equal to the transformer input voltage multiplied by the turn ratio (e.g., 1:4 in the example embodiment of FIG. 8), controlling the rate at which the transformer voltage changes also controls the slew rate of the output bus voltage. According to various embodiments, output pulses are generated by controlling the output switch sets 510 while the output bus voltage is present in the same manner as with the first capacitor 502A/second capacitor 502B based architecture described previously in this disclosure. The output switch sets 510 can be switched from the OPEN state to the CLOSED state as quickly as desired as the output pulse slew rate does not need to be limited, as discussed above, according to some embodiments.

According to some embodiments, other PFA systems may be associated with the circuit 500 of FIGS. 5A, 5B, 5C, and 5D described above. According to some embodiments, a PFA system includes a high voltage supply 504, a controller system 324 and a circuit communicatively connected to the controller system 324. With reference at least to block 1102 of method 1100 of FIG. 11 and block 1202 of method 1200 of FIG. 12, according to various embodiments, the circuit may be electrically connected to the high voltage supply 504 to receive input voltage therefrom. According to various embodiments, the circuit includes a first plurality of capacitors (e.g., first capacitor 502A and second capacitor 502B) electrically connected to the high voltage supply 504 via a plurality of switches 506, and at least a first output switch set of the output switch sets 510 electrically connecting or electrically coupling the first plurality of the capacitors 502A, 502B to a plurality of selectable PFA electrodes (e.g., electrodes 315, 415 or electrodes of transducers 220).

According to some embodiments, and with reference to at least block 1104 of method 1100 of FIG. 11 and block 1204 of method 1200 of FIG. 12, according to various embodiments, the controller system 324 may be configured to cause (i) switching of at least some of the plurality of switches 506 to produce a first switch configuration or state in which the first plurality of capacitors 502A, 502B is a first series circuit or circuit arrangement. In some embodiments, the first series circuit or circuit arrangement is configured to charge the first plurality of capacitors 502A, 502B. For example, according to some embodiments, FIG. 5B is a schematic representation of a portion of the circuit of FIG. 5A indicating an example of such first series circuit or circuit arrangement configured to charge the first plurality of capacitors 502A, 502B. FIG. 5B also shows a current flow path 508 associated with the first series circuit or circuit arrangement, according to some embodiments. In FIG. 5B, as discussed above, switch 506-3 and switch 506-2, are each schematically shown in respective NON-OPEN state, while switch 506-1 and switch 506-4 are each schematically shown in a respective OPEN state.

According to some embodiments, and with reference to at least block 1106 of method 1100 of FIG. 11 and block 1206 of method 1200 of FIG. 12, according to various embodiments, the controller system 324 may be configured to cause (ii) switching, subsequent (i), of at least some of the plurality of switches 506 to produce a second switch configuration or state in which the first plurality of capacitors 502A, 502B is in a second series circuit or circuit arrangement different than the first series circuit or circuit arrangement. According to various embodiments, such as some embodiments associated with at least block 1106 of method 1100 of FIG. 11, the second series circuit or circuit arrangement may be configured to apply an output voltage across at least a first output switch set of the output switch sets 510, the output voltage greater than the input voltage from the high voltage supply 504. For example, according to some embodiments, FIG. 5C is a schematic representation of a portion of the circuit of FIG. 5A indicating a second series circuit or circuit arrangement (different than the first series circuit or circuit arrangement of FIG. 5B) configured to apply an output voltage across at least a first output switch set of the output switch sets 510, the output voltage greater than the input voltage. FIG. 5C also shows a current flow path 509 associated with the second series circuit or circuit arrangement, according to some embodiments. In FIG. 5C, switch 506-1 and switch 506-4 are each schematically shown in a respective NON-OPEN state, while switch 506-3 and switch 506-2 are each schematically shown in a respective OPEN state. The respective OPEN states and the respective NON-OPEN states associated with the particular switch 506 configurations when the controller system 324 causes (i) and (ii), may be the same or similar to respective uses of OPEN and NON-OPEN used earlier in this disclosure. For example, according to some example embodiments, in the first switch configuration or state (e.g., FIG. 5B provides one example of such a switch state, according to some embodiments) each switch in a first switch set (e.g., switches 506-2, 506-3) of the plurality of switches 506 is in a respective NON-OPEN state configured to allow a respective level of electric current to be deliverable through the switch in the first switch set (e.g., switches 506-2, 506-3), and in the second switch configuration or state (e.g., FIG. 5C provides one example of such a switch state, according to some embodiments), each switch in the first switch set (e.g., switches 506-2, 506-3) is in a respective OPEN state configured to prevent flow of electric current through the switch in the first switch set (e.g., switches 506-2, 506-3), the respective level of electric current deliverable through the switch in the first switch set (e.g., switches 506-2, 506-3) in the respective NON-OPEN state greater than any electric current deliverable through the switch in the first switch set (e.g., switches 506-2, 506-3) in the respective OPEN state. According to some embodiments, in the first switch configuration or state (e.g., FIG. 5B provides one example of such a switch state, according to some embodiments), each switch in a second switch set (e.g., 506-1, 506-4) of the plurality of switches 506 is in a respective OPEN state configured to prevent flow of electric current through the switch in the second switch set (e.g., 506-1, 506-4), and, in the second switch configuration or state (e.g., FIG. 5C provides one example of such a switch state, according to some embodiments), each switch in the second switch set (e.g., 506-1, 506-4) is in a respective NON-OPEN state configured to allow a respective level of electric current to be deliverable through the switch in the second switch set (e.g., 506-1, 506-4). In some embodiments, the respective level of electric current deliverable through the respective switch in the second switch set (e.g., 506-1, 506-4) in the respective NON-OPEN state is greater than any electric current deliverable through the respective switch in the second switch set (e.g., 506-1, 506-4) in the respective OPEN state.

According to some embodiments, and with reference to at least block 1108 of method 1100 of FIG. 11 and block 1208 of method 1200 of FIG. 12, according to various embodiments, the controller system 324 is configured to cause (iii) switching of at least one of the output switches of at least the first output switch set of the output switch sets 510 to generate a plurality of output pulse sets (which may include, e.g., output pulse set 516, according to some embodiments) at least from energy stored at least in the first plurality of capacitors 502A, 502B, each output pulse set in the plurality of output pulse sets configured to cause PFA.

According to various embodiments, such as some embodiments associated with at least block 1206 of method 1200 of FIG. 12, electric current through the first plurality of capacitors 502A, 502B in the second series circuit or circuit arrangement is in an opposite direction to electric current through the first plurality of capacitors in the first series circuit or circuit arrangement, for example, as shown in FIGS. 5B and 5C by respective current flow paths 508, 509.

According to various embodiments, at least a first switch in the first switch set (e.g., 506-2, 506-3) is a semiconductor switch, and the PFA system includes an electric current control circuit electrically connected to the first switch and configured to control electric current through the first switch. FIG. 7 shows an electric current control circuit that may be employed, according to some embodiments. According to some embodiments, at least a first switch in the first switch set (e.g., 506-2, 506-3) is a semiconductor switch including a transistor. In some embodiments, the transistor is a bipolar junction transistor. In some embodiments, the transistor is an insulated-gate bipolar transistor (IGBT). In some embodiments, the transistor is a field effect transistor. In some embodiments, the transistor is a MOSFET. According to some embodiments, the plurality of switches 506 is arranged in a full bridge configuration (for example, as shown in FIGS. 5A, 5B and 5C).

According to some embodiments, at least some of which pertain to the circuit 500 of FIG. 5A, such circuit 500 may include one or more second capacitors, where the plurality of switches 506 electrically connect the one or more second capacitors to the first plurality of capacitors 502A, 502B to charge the first plurality of capacitors 502A, 502B with charge stored in the one or more second capacitors 512 (one shown in each of FIGS. 5B, 5C, and 5D, but more than one may be present, e.g., in series or other configurations, according to various embodiments). According to some embodiments, one or more second capacitors 512 may form the output capacitance of the high voltage supply 504.

PFA may require the delivery of a relatively large number of output pulses in rapid succession (e.g., 300 pulses in 30 ms). According to some embodiments associated with FIG. 5A, each output pulse (e.g., in output pulse set 516) consumes some energy stored in the output capacitance (e.g., of one or more second capacitors 512) of the voltage supply 504, as well as some of the energy stored in the first plurality of capacitors 502A, 502B. In some cases, the high voltage supply 504 may not have sufficient output power to significantly recharge its output capacitance (e.g., of one or more of the second capacitors 512) between various output pulses, especially in multi-electrode PFA systems in which greater numbers of output pulses are required from increased numbers of electrodes that may be concurrently activated. For example, in the case in which the system is used in a voltage multiplying configuration (for example, a voltage multiplier as described above in this disclosure), the initial output pulse (e.g., in output pulse set 516) occurs at maximum voltage ($V_O=2V_S$, where $V_S$ is the supply voltage, $V_O$ is the output voltage derived in accordance with a voltage multiple equal to “two”). In cases in which the high voltage supply 504 cannot significantly recharge its output capacitance (e.g., of one or more second capacitors 512) in the time available before the next output pulse, the next output pulse will be delivered at a lower voltage, and the voltage for subsequent pulses continues to droop lower. According to various embodiments, to limit the droop over the entire output pulse delivery period to an acceptable value (e.g., 10%, 5%, 1%, or less) the charging voltages can be adjusted to initially charge the high voltage supply's output capacitance (e.g., one or more second capacitors 512) to greater than half of the desired output voltage, and the first plurality of capacitors 502A, 502B to the remainder of the desired output voltage.

According to various embodiments, after delivery of the first output pulse set (which may, in some embodiments, be a first pulse in the output pulse set 516), the charging process described above in this disclosure (e.g., with respect to FIGS. 5B and 5C) is repeated and charge is transferred from the one or more second capacitors 512 to the first plurality of capacitors 502A, 502B in such a manner that the voltage across the one or more second capacitors 512 decreases, the voltage across the first plurality of capacitors 502A, 502B increases, and the sum of the voltage across the one or more second capacitors 512 plus the voltage across the first plurality of capacitors 502A, 502B remains equal to the desired output voltage. For example, in some embodiments, voltage across each capacitor of the first plurality of capacitors 502A, 502B increases, and concurrently, voltage across each capacitor of the one or more second capacitors decreases in response to the controller system causing (i) (e.g., switch state “(a)”, which may be provided by the example switch state of FIG. 5B, in some embodiments). In some embodiments, the controller system 324 is configured to repeat (i) and (ii) (e.g., switch state “(b)”, which may be provided by the example switch state of FIG. 5C, in some embodiments) with each successive output pulse set of the plurality of output pulse sets (which may include output pulse set 516, according to some embodiments) that is generated. In some embodiments, voltage across each capacitor of the first plurality of capacitors 502A, 502B increases, and concurrently, voltage across each capacitor of the one or more second capacitors 512 decreases in response to each occurrence of the controller system 324 causing (a). According to some embodiments, a voltage across the first plurality of capacitors 502A, 502B incrementally increases, and concurrently, voltage across the one or more second capacitors 512 incrementally decreases with each successive output pulse set of the plurality of output pulse sets that is generated. In some embodiments, a sum of (iv) the voltage across each capacitor of the first plurality of capacitors 502A, 502B and (v) the voltage across each capacitor of the one or more second capacitors 512 remains constant or substantially constant (e.g., avoiding droop in some embodiments) with each successive output pulse set of the plurality of output pulse sets that is generated. According to various embodiments, this output pulse/re-charging process may continue for subsequent output pulse sets. According to various embodiments, this output pulse/re-charging process may continue for subsequent output pulse sets until such time that the voltage across the first plurality of capacitors 502A, 502B is substantially equal to the voltage across the one or more second capacitors 512, allowing for the delivery of many output pulses or output pulse sets within a determined or predetermined time interval (e.g., during a refractory period within a cardiac cycle) with essentially zero droop in voltage between output pulse sets.

Notwithstanding that, in some embodiments, the circuit 500 may preferably make use of safety rated capacitors (e.g., Class-Y1 capacitors or Class-Y2 capacitors) that are designed not to fail short circuit, such failures may still occur, either due to failure of the capacitors themselves or due to debris shorting them externally. According to various embodiments, additional circuit features may be included to check for these and other failures and consequently allow for a reduction in the risk of harm. In some embodiments, at a specified interval (e.g., upon system power on, prior to starting PFA, or prior to each refractory period in which output pulses are to be delivered), the system (e.g., the system 200, the system 300, or each of the system 200 and the system 300 or the controller 324 or circuit 500 thereof in some embodiments) can charge at least the first plurality of capacitors 502A, 502B via techniques described above by way of example, and then deliver an output pulse to a load having a known resistance. The voltage and current associated with the output pulse can be measured by high-speed (e.g., 10 MSPS (MegaSamples (106 samples) Per Second))

voltage and current sensing circuits. According to various embodiments, the value of the capacitance can be computed based on the voltage and current information and the known resistance of the load. If the value of the computed capacitance differs from an expected value by more than a specified amount, the system may be rendered safe by disconnecting the link from the output bus. For example, in FIG. 5A, circuit 500 may disconnect the link from the output switches via the switch identified as S6 and allow crowbar circuits to activate via the switches identified as S5 and S7, thereby eliminating any voltage across the output switches.

In some embodiments, the system may include individual discharge circuits (e.g., discharge circuits 520A, 520B in FIG. 5E, according to some embodiments) for each capacitor of the first plurality of capacitors (e.g., for each of capacitor 502A (C1) and capacitor 502B (C2)). According to some embodiments, during a test process, the discharge circuits may be activated to short each of capacitor 502A and capacitor 502B in turn with a test pulse delivered in each case. This configuration allows the voltage values of capacitors 502A and 502B to be determined individually by respective voltage sense circuits 520C, 520D, thus confirming that both capacitor 502A and capacitor 502B are intact. This confirmation may be important, because each of capacitor 502A and capacitor 502B may in fact be formed by many individual components (e.g., each of capacitor 502A (C1) and capacitor 502B (C2) may be composed of multiple capacitors (e.g., four 1 μF capacitors in some embodiments) in parallel, in which case a complete short circuit of capacitor 502A combined with open circuit failure of half of the components used to create capacitor 502B would not be detected by only verifying the combined voltage value of capacitor 502A and capacitor 502B, thus leaving only one capacitor intact. Checking each capacitor of the first plurality of capacitors 502A, 502B individually may ensure that two separate failures are required before the high voltage supply 504 is DC connected to the patient (while likely is an unsafe and undesired condition in some embodiments). According to some embodiments, this test may be performed at a high frequency (e.g., before each refractory period in which pulses are to be delivered in some embodiments) thereby making the probability of two failures occurring between successive tests vanishingly small. It is noted in various embodiments, that the discharge circuits that allow deliberate short circuiting of capacitor 502A and capacitor 502B may be constructed of safety rated components in order to not unacceptably increase the likelihood of a failure short circuiting capacitor 502A or capacitor 502B.

According to some embodiments, it may be desired to continually monitor the state of the capacitors 502A and 502B (for example, to potentially allow the use of non-safety rated components), and the system (e.g., the system 200, the system 300, or each of the system 200 and the system 300 or the controller 324 or circuit 500 thereof in some embodiments) may include a respective voltage monitoring circuit, such as voltage sense circuits 520C, 520D, for each capacitor. When charging of capacitors 502A and 502B begins, if the voltage across each of capacitors 502A and 502B does not reach the expected value (e.g., due to a short circuit), this condition is detected (e.g., by way of voltage sense circuits 520C, 520D), and the link is disconnected from the output bus via S6, helping to ensure that the system does not produce a high voltage across the output switches unless capacitors 502A and 502B are intact. The expected value of the voltage can be determined from the relationships Q=CV (where Q=charge, C=capacitance, and V=voltage). Charge can be determined by integrating current over time.

In some embodiments, the system includes at least one current measuring circuit, such as current sense circuit 522, that measures the current flowing through the series circuit or circuit arrangement of capacitors 502A and 502B and the load (e.g., R1, R2 in FIG. 5E) (whether the load is a known test load or an actual patient load). The current sense circuit 522 shown in FIG. 5E may be connected to each of the first capacitor 502A (C1) and the second capacitor 502B (C2) to monitor current through such capacitors. Current sense circuit 522 may also be included in the circuit 500A, as shown in FIG. 5A, according to some embodiments.

In some embodiments, redundant circuits for each of capacitors 502A and 502B may be implemented to ensure that a failure of a single sensing or measuring circuit does not lead to failure to detect a short circuit. In some embodiments, resistors implemented in the respective sensing circuit may be configured to have certain features (e.g., high impedance, long creepage distances, high power rating, high voltage rating, etc.) to ensure that they are unlikely to fail short circuit and that their presence does not defeat the purpose of capacitors 502A and 502B by allowing excessive low frequency current to bypass capacitor 502A or capacitor 502B. For example, FIG. 9 may represent an implementation of each of voltage monitoring circuits 520A, 520B, according to some embodiments. In this regard, FIG. 9 illustrates two series connections of redundant resistors R1-R5 and R6-R10, and such chains of resistors may have certain features discussed in more detail below that ensure that they are unlikely to fail short circuit and that their presence does not defeat the purpose of capacitors 502A and 502B by allowing excessive low frequency current to bypass capacitor 502A or capacitor 502B.

Figure 5E:
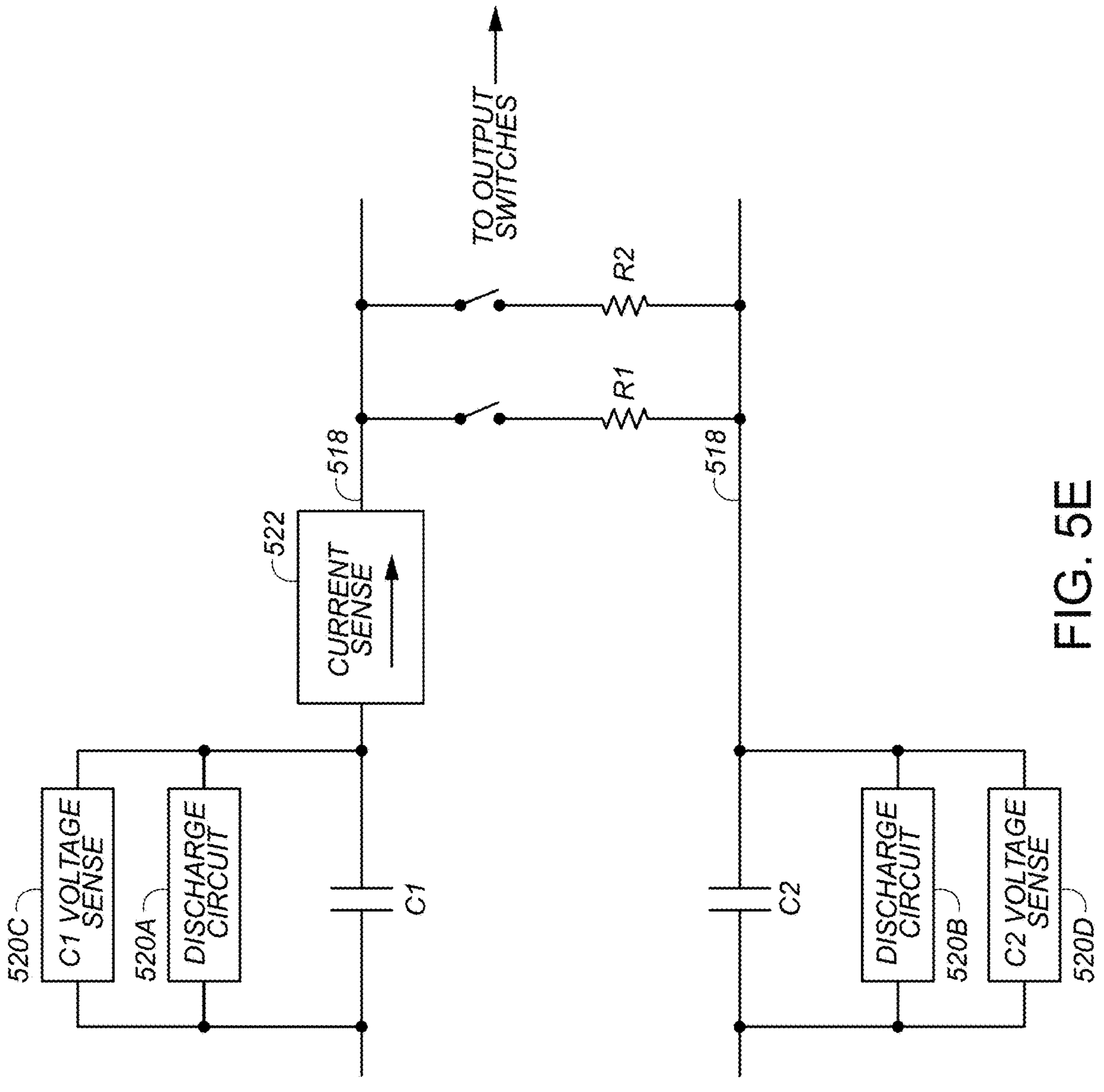
FIG. 5E includes a schematic representation of a portion of a circuit employed by a pulsed field ablation system, where such circuit may be included as part of the circuit of FIG. 5A, according to some embodiments.

According to various embodiments, the circuit 500 includes a plurality of sensing circuits (such as those described above), each sensing circuit of the plurality of sensing circuits electrically connected to a respective capacitor of the first plurality of capacitors 502A, 502B. According to some embodiments, the controller system 324 is configured to individually determine the capacitance of each respective capacitor of the first plurality of capacitors 502A, 502B, each capacitance determined based at least on a signal set provided by the respective sensing circuit of the plurality of sensing circuits. According to various embodiments, the controller system 324 is configured to determine, based at least on a signal set provided by a particular sensing circuit of the plurality of sensing circuits, a capacitance of the respective capacitor of the first plurality of capacitors 502A, 502B. In the example of FIG. 5E, the voltage sense circuits 520C, 520D may be configured to determine the capacitance of their respective capacitors 502A (C1), 502B (C2).

Figure 9:
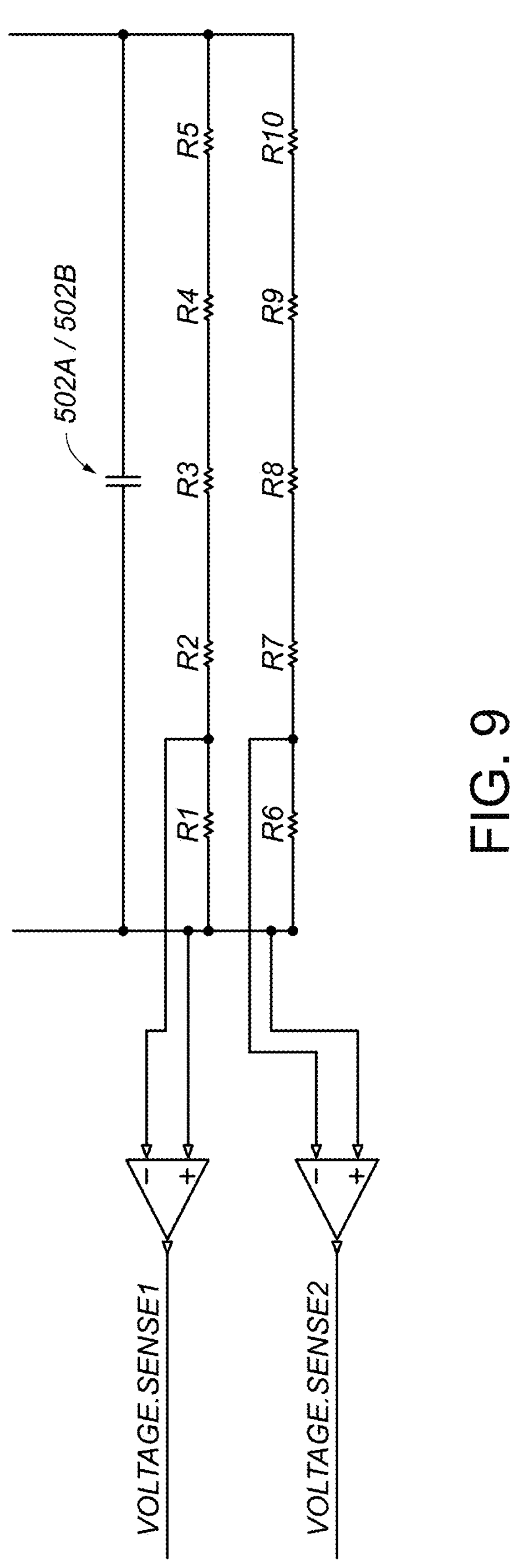
FIG. 9 includes a representation of a capacitor sensing circuit, according to some embodiments, wherein the capacitor sensing circuit may be configured to sense a state of a capacitor in an output pulse generation circuit of a pulsed field ablation system, according to some embodiments.

FIG. 9 shows an example embodiment of a particular sensing circuit of the plurality of sensing circuits, according to some embodiments. For instance, FIG. 9 may represent an implementation of each of voltage monitoring circuits 520A, 520B, according to some embodiments. According to various embodiments, the capacitor sensed is one of the first plurality of capacitors (e.g., capacitor 502A or capacitor 502B). According to various embodiments, the signal set provided by the particular sensing circuit of the plurality of sensing circuits includes a signal provided by a voltage sensing portion of the particular sensing circuit (e.g., voltage signals are provided by the circuit of FIG. 9).

According to some embodiments, the circuit (e.g., circuit 500 in some embodiments) includes an electric current sensing circuit (e.g., current sense circuit 522 shown in FIGS. 5A and 5E) configured to sense electric current through each capacitor of the first plurality of capacitors.

According to some embodiments, the controller system 324 is configured to determine, based at least on a signal set provided by the electric current sensing circuit, the capacitance of each respective capacitor of the first plurality of capacitors. According to various embodiments, the particular sensing circuit includes a plurality of redundant sensing circuits. According to various embodiments, the controller system 324 is configured to determine multiple capacitance values for each respective capacitor of the first plurality of capacitors, each capacitance value of the multiple capacitance values determined based at least on a signal set provided by a respective one of the redundant sensing circuits of the particular sensing circuit. For example, FIG. 9 shows a redundancy of voltage sense circuits (e.g., VOLTAGE.SENSE1, VOLTAGE.SENSE2), according to some embodiments. In FIG. 9, the capacitor 502A/502B is bridged by two chains of resistors. In some embodiments, the total resistance of the chains is made very high to ensure that any current flowing through the resistor chains to the patient remains within accepted safety limits. According to various embodiments, voltage is sensed across a portion of the chain that is less than the entirety of the chain to sense a scaled down version of the actual capacitor voltage.

While some of the embodiments disclosed above are described with examples of cardiac mapping, ablation, or both, the same or similar embodiments may be used for mapping, ablating, or both, other bodily organs, for example with respect to the intestines, the bladder, or any bodily organ to which the devices of the present invention may be introduced.

Subsets or combinations of various embodiments described above can provide further embodiments.

These and other changes can be made to the invention in light of the above-detailed description. In general, in the following claims, the terms used should not be construed to limit the invention to the specific embodiments disclosed in the specification and the claims, but should be construed to include other transducer-based device systems including all medical treatment device systems and all medical diagnostic device systems in accordance with the claims. Accordingly, the invention is not limited by the disclosure, but instead its scope is to be determined entirely by the following claims.

What is claimed is:

1. A pulsed field ablation system comprising:

a high voltage supply;

a controller system; and a circuit communicatively connected to the controller system, the circuit electrically connected to the high voltage supply to receive input voltage therefrom, the circuit comprising:

a first plurality of capacitors electrically connected to the high voltage supply via a plurality of switches, and at least a first output switch set electrically connecting the first plurality of the capacitors to a plurality of selectable pulsed field ablation electrodes, wherein the controller system is configured to cause:

(i) switching of at least some of the plurality of switches to produce a first switch configuration in which the first plurality of capacitors is in a first series circuit configured to charge the first plurality of capacitors, (ii) switching, subsequent (i), of at least some of the plurality of switches to produce a second switch configuration in which the first plurality of capacitors is in a second series circuit configured to apply an output voltage across at least the first output switch set, the output voltage greater than the input voltage, the second series circuit different than the first series circuit, and (iii) switching of at least one output switch of the output switches of at least the first output switch set to generate a plurality of output pulse sets at least from energy stored at least in the first plurality of capacitors, each output pulse set in the plurality of output pulse sets configured to cause pulsed field ablation.

2. The pulsed field ablation system of claim 1, wherein electric current through the first plurality of capacitors in the second series circuit is in an opposite direction to electric current through the first plurality of capacitors in the first series circuit.

3. The pulsed field ablation system of claim 1, wherein, in the first switch configuration, each switch in a first switch set of the plurality of switches is in a respective NON-OPEN state configured to allow a respective level of electric current to be deliverable through the switch in the first switch set, and wherein, in the second switch configuration, each switch in the first switch set is in a respective OPEN state configured to prevent flow of electric current through the switch in the first switch set, the respective level of electric current deliverable through the switch in the first switch set in the respective NON-OPEN state greater than any electric current deliverable through the switch in the first switch set in the respective OPEN state.

4. The pulsed field ablation system of claim 3, wherein at least a first switch in the first switch set is a semiconductor switch, and wherein the pulsed field ablation system comprises an electric current control circuit electrically connected to the first switch and configured to control electric current through the first switch.

5. The pulsed field ablation system of claim 3, wherein, in the first switch configuration, each switch in a second switch set of the plurality of switches is in a respective OPEN state configured to prevent flow of electric current through the switch in the second switch set, and wherein, in the second switch configuration, each switch in the second switch set is in a respective NON-OPEN state configured to allow a respective level of electric current to be deliverable through the switch in the second switch set, the respective level of electric current deliverable through the switch in the second switch set in the respective NON-OPEN state greater than any electric current deliverable through the switch in the second switch set in the respective OPEN state.

6. The pulsed field ablation system of claim 5, wherein at least a first switch in the first switch set is a semiconductor switch comprising a transistor.

7. The pulsed field ablation system of claim 6, wherein the transistor is a bipolar junction transistor.

8. The pulsed field ablation system of claim 6, wherein the transistor is an insulated-gate bipolar transistor.

9. The pulsed field ablation system of claim 6, wherein the transistor is a field effect transistor.

10. The pulsed field ablation system of claim 6, wherein the transistor is a MOSFET.

11. The pulsed field ablation system of claim 1, wherein the plurality of switches is arranged in a full bridge configuration.

12. The pulsed field ablation system of claim 1, wherein the controller system is configured to repeat (i) and (ii) with each successive output pulse set of the plurality of output pulse sets that is generated.

13. The pulsed field ablation system of claim 12, wherein voltage across each capacitor of the first plurality of capacitors increases, and concurrently, voltage across each capacitor of the one or more second capacitors decreases in response to each occurrence of the controller system causing (i).

14. The pulsed field ablation system of claim 1, wherein the circuit comprises one or more second capacitors, the plurality of switches electrically connecting the one or more second capacitors to the first plurality of capacitors to charge the first plurality of capacitors with charge stored in the one or more second capacitors.

15. The pulsed field ablation system of claim 14, wherein voltage across each capacitor of the first plurality of capacitors increases, and concurrently, voltage across each capacitor of the one or more second capacitors decreases in response to the controller system causing (i).

16. The pulsed field ablation system of claim 14, wherein voltage across the first plurality of capacitors incrementally increases, and concurrently, voltage across the one or more second capacitors incrementally decreases with each successive output pulse set of the plurality of output pulse sets that is generated.

17. The pulsed field ablation system of claim 14, wherein a sum of (iv) the voltage across each capacitor of the first plurality of capacitors and (v) the voltage across each capacitor of the one or more second capacitors remains constant with each successive output pulse set of the plurality of output pulse sets that is generated.

18. The pulsed field ablation system of claim 1, wherein the circuit comprises a plurality of sensing circuits, each sensing circuit of the plurality of sensing circuits electrically connected to a respective capacitor of the first plurality of capacitors, and wherein the controller system is configured to determine, based at least on a signal set provided by a particular sensing circuit of the plurality of sensing circuits, a capacitance of the respective capacitor of the first plurality of capacitors.

19. The pulsed field ablation system of claim 18, wherein the signal set provided by the particular sensing circuit of the plurality of sensing circuits includes a signal provided by a voltage sensing portion of the particular sensing circuit.

20. The pulsed field ablation system of claim 19, wherein the circuit comprises an electric current sensing circuit configured to sense electric current through each capacitor of the first plurality of capacitors, and wherein the controller system is configured to determine, based at least on a signal set provided by the electric current sensing circuit, the capacitance of each respective capacitor of the first plurality of capacitors.

21. The pulsed field ablation system of claim 18, wherein the particular sensing circuit comprises a plurality of redundant sensing circuits, and wherein the controller system is configured to determine multiple capacitance values for each respective capacitor of the first plurality of capacitors, each capacitance value of the multiple capacitance values determined based at least on a signal set provided by a respective one of the redundant sensing circuits of the particular sensing circuit.

22. The pulsed field ablation system of claim 18, wherein the controller system is configured to individually determine the capacitance of each respective capacitor of the first plurality of capacitors, each capacitance determined based at least on a signal set provided by the respective sensing circuit of the plurality of sensing circuits.

* * * * *